United States Patent
Sattell et al.

(10) Patent No.: US 11,633,578 B2
(45) Date of Patent: Apr. 25, 2023

(54) APPARATUS AND METHODS FOR LOADING AN ENDOVASCULAR IMPLANT INTO A DELIVERY CATHETER

(71) Applicant: CEREVASC, INC., Auburndale, MA (US)

(72) Inventors: Jack B. Sattell, Boston, MA (US); David A. Rezac, Hopkinton, MA (US); Alexander Bonin, Franklin, MA (US)

(73) Assignee: CereVasc, Inc., Auburndale, MA (US)

( * ) Notice: Subject to any disclaimer, the term of this patent is extended or adjusted under 35 U.S.C. 154(b) by 292 days.

(21) Appl. No.: 17/156,559

(22) Filed: Jan. 23, 2021

(65) Prior Publication Data
US 2021/0228846 A1 Jul. 29, 2021

Related U.S. Application Data

(60) Provisional application No. 62/965,105, filed on Jan. 23, 2020.

(51) Int. Cl.
*A61F 2/95* (2013.01)
*A61M 27/00* (2006.01)

(52) U.S. Cl.
CPC ......... *A61M 27/006* (2013.01); *A61F 2/9522* (2020.05); *A61M 2205/04* (2013.01); *A61M 2210/0693* (2013.01)

(58) Field of Classification Search
CPC .... A61F 2/04; A61F 2/844; A61F 2/95; A61F 2/9522; A61F 2/9524; A61F 2/9525; A61F 2/9526; A61M 25/01; A61M 2207/00; A61M 27/002; A61M 27/006; A61M 27/008; B25B 27/14
See application file for complete search history.

(56) References Cited

U.S. PATENT DOCUMENTS

| | | | |
|---|---|---|---|
| 5,992,000 A * | 11/1999 | Humphrey | A61F 2/958 29/516 |
| 9,364,325 B2 * | 6/2016 | Alon | A61F 2/2436 |
| 9,387,311 B1 | 7/2016 | Heilman et al. | |
| 2008/0109069 A1 * | 5/2008 | Coleman | A61F 2/064 623/1.36 |
| 2009/0099530 A1 * | 4/2009 | Adams | A61F 2/9525 623/1.11 |
| 2010/0292779 A1 * | 11/2010 | Straubinger | A61F 2/9525 623/1.23 |
| 2018/0207412 A1 | 7/2018 | Malek et al. | |

FOREIGN PATENT DOCUMENTS

WO    WO 2018/071600    4/2018

* cited by examiner

*Primary Examiner* — Sarah W Aleman
(74) *Attorney, Agent, or Firm* — Vista IP Law Group, LLP

(57) ABSTRACT

An apparatus for loading an endovascular shunt into a delivery catheter includes a base, a boss rod connected to, and extending longitudinally across, the base, and a plurality of guide bosses slidably coupled to the boss rod. The guide bosses include a delivery catheter guide boss coupled to the delivery catheter, a malecot holding tube guide boss, wherein a malecot holding tube is connected to a first lateral side of the malecot guide boss extending towards the delivery catheter guide boss, a claw assembly guide boss, where a claw assembly is attached to a first lateral side of the claw guide boss extending towards the malecot holding tube guide boss, and a chase pin guide boss, wherein a chase pin is connected to a first lateral side of the chase pin guide boss extending towards the claw assembly guide boss.

14 Claims, 62 Drawing Sheets

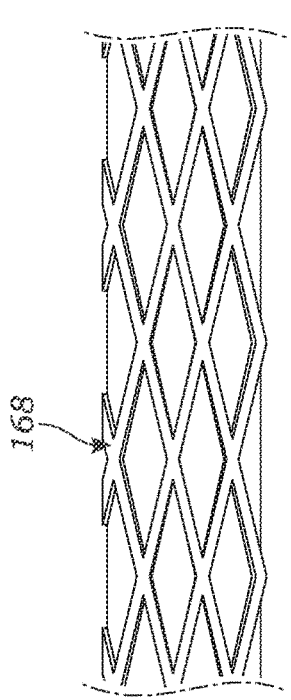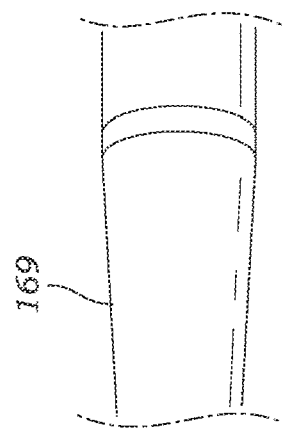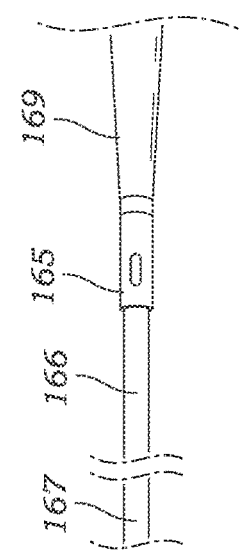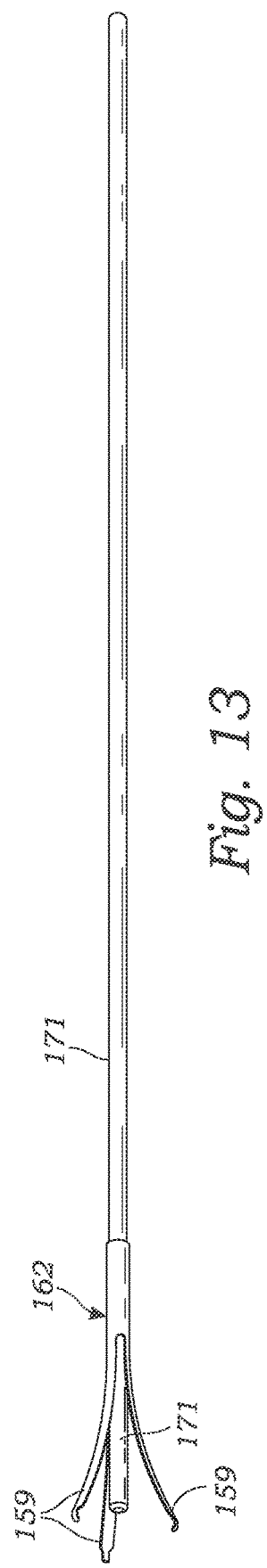

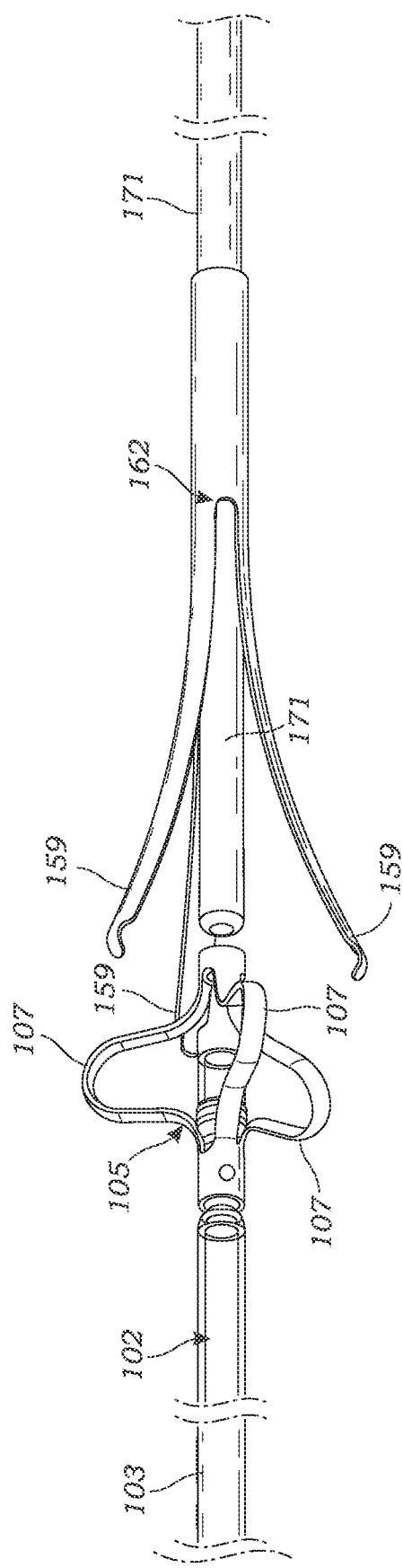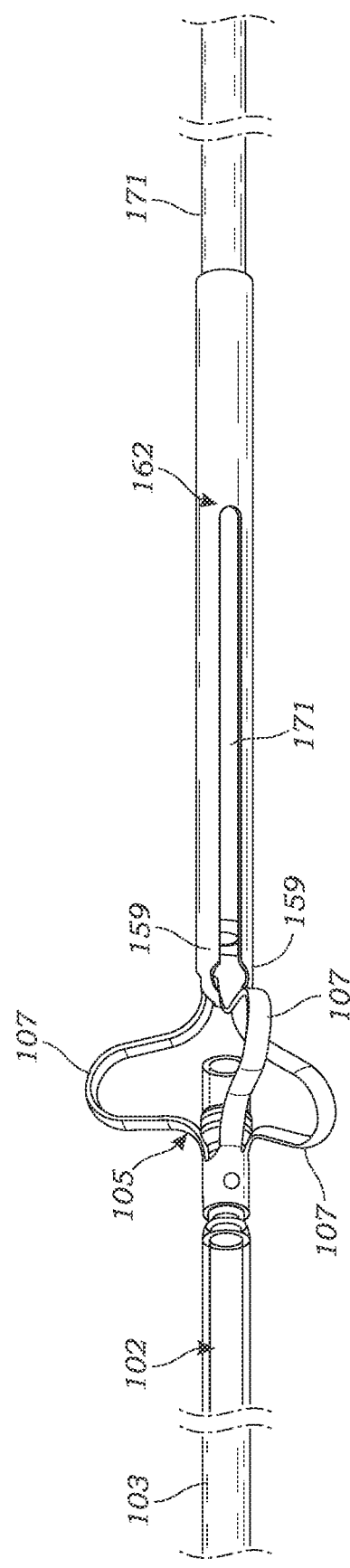

Fig. 2.1

Direction of Motion
| Left to Right + |
| Right to Left − |

Component/Guide Boss Movement, mm

| Step | Description | Shroud | Transfer Tube/First Guide Boss | Malecot Holding Tube Cover/Second Guide Boss | Malecot Holding Tube/Third Guide Boss | Claw Assy/Fourth Guide Boss |
|---|---|---|---|---|---|---|
| 1 | Capture Malecot | 0 | 0 | 0 | 0 | 6 |
| 2 | Bottom out shunt base in shroud | 0 | 0 | -16 | -16 | -16 |
| 3 | Capture/retain end of shunt | 0 | +15 | 0 | 0 | 0 |
| 4 | Stretch Shunt Tube | 0 | +12.5 | 0 | +12.5 | +12.5 |
| 5 | Remove malecot tube from inside of shroud | 0 | +7.5 | 0 | +7.5 | 0 |
| 6 | Capture remaining shunt tube | 0 | +14 | 0 | 0 | 0 |
| 7 | Capture part of malecot | 0 | +5.5 | +5.5 | +5.5 | 0 |
| 8 | Release claw | 0 | 0 | +10 | +10 | 0 |
| 9 | Capture remaining malecot | 0 | +8 | +8 | +8 | +8 |

*Fig. 27*

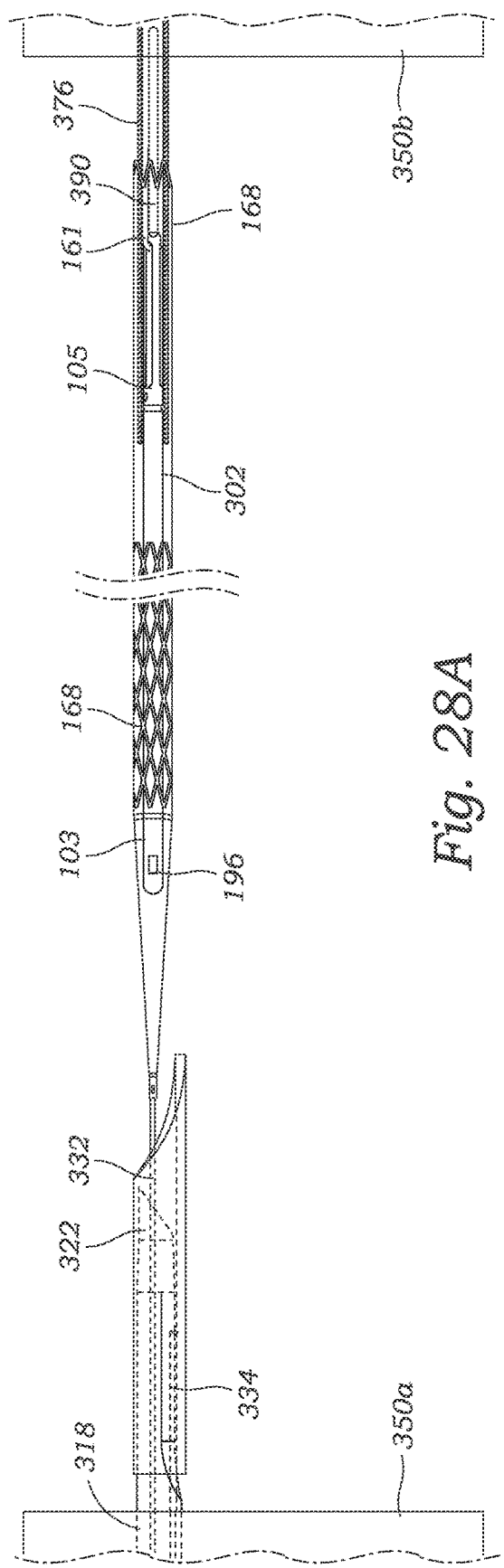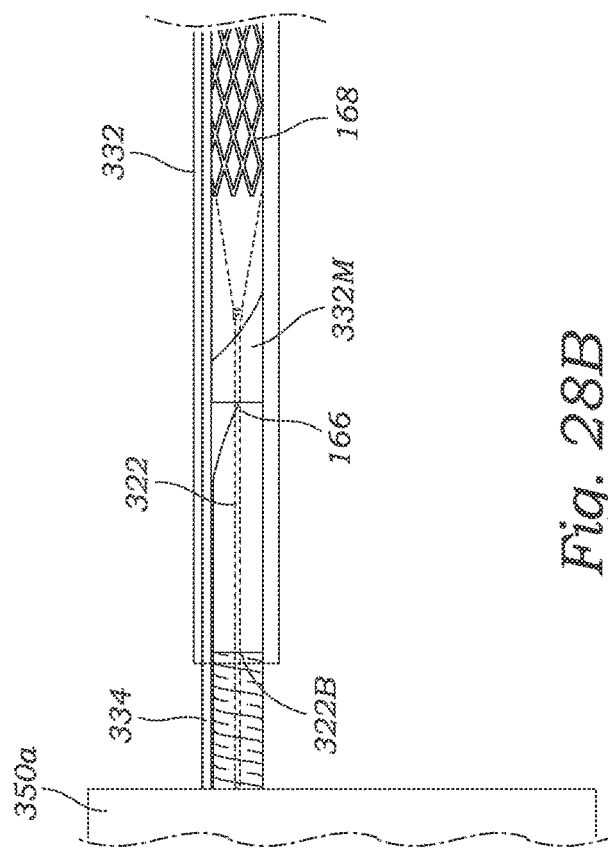

| Step | Description | (All Movement Distal) Guide Boss Movement, inches | | | |
|---|---|---|---|---|---|
| | | Delivery Catheter Guide Boss | Malecot Holding Tube Guide Boss | Claw Guide Boss | Chase Pin Guide Boss |
| 1 | Capture/retain proximal end of Shunt | 0.887 | 0 | 0 | 0 |
| 2 | Stretch Shunt body | 0 | 0.622 | 0.622 | 0.622 |
| 3 | Capture remainder of Shunt body | 1.288 | 0 | 0 | 0 |
| 4 | Claw releases Malecot, capture Malecot in Shroud | 0.25 | 0.25 | 0 | 0 |
| 5 | Capture remainder of Malecot | 0.5 | 0.5 | 0.5 | 0 |

Fig. 49

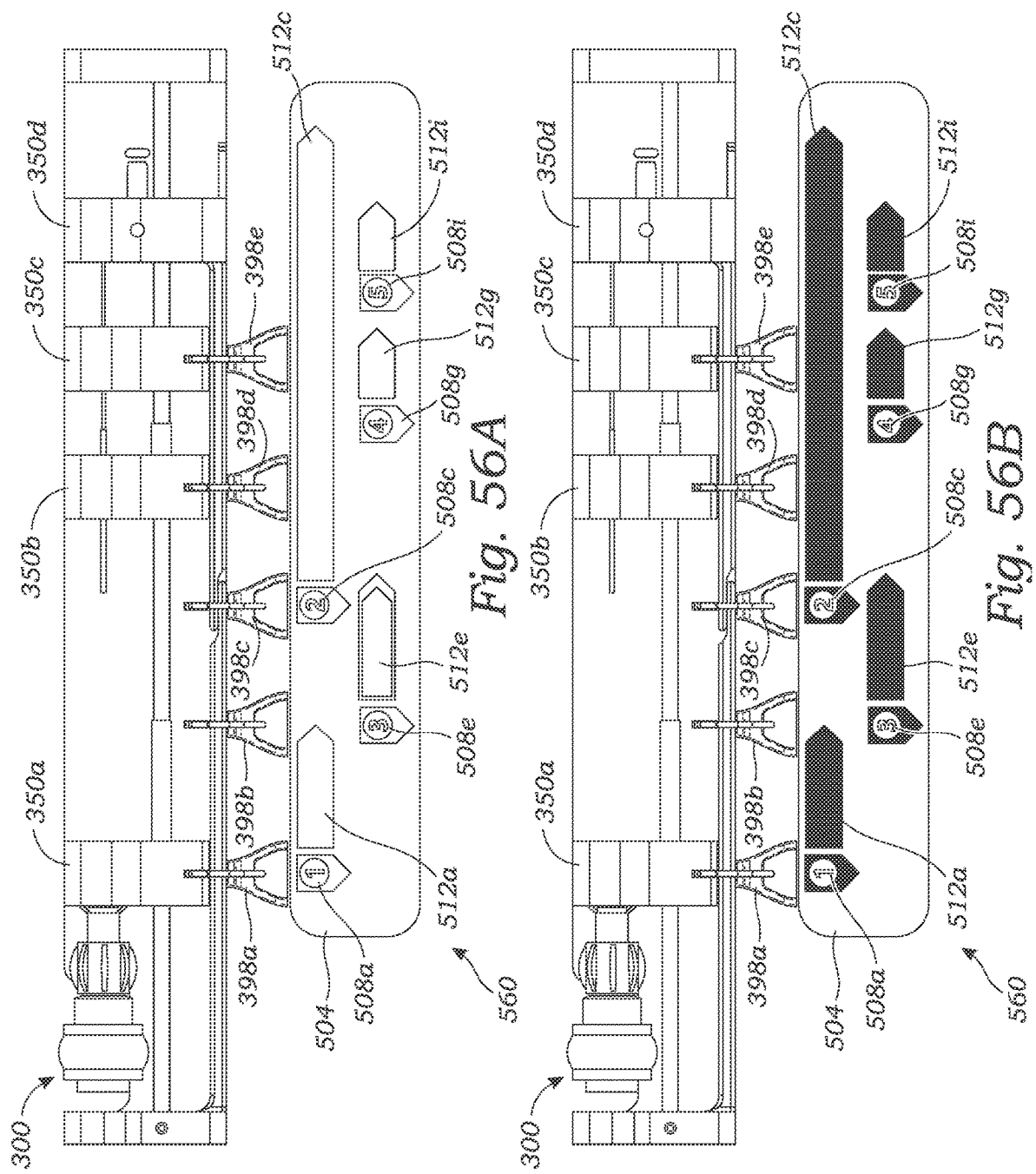

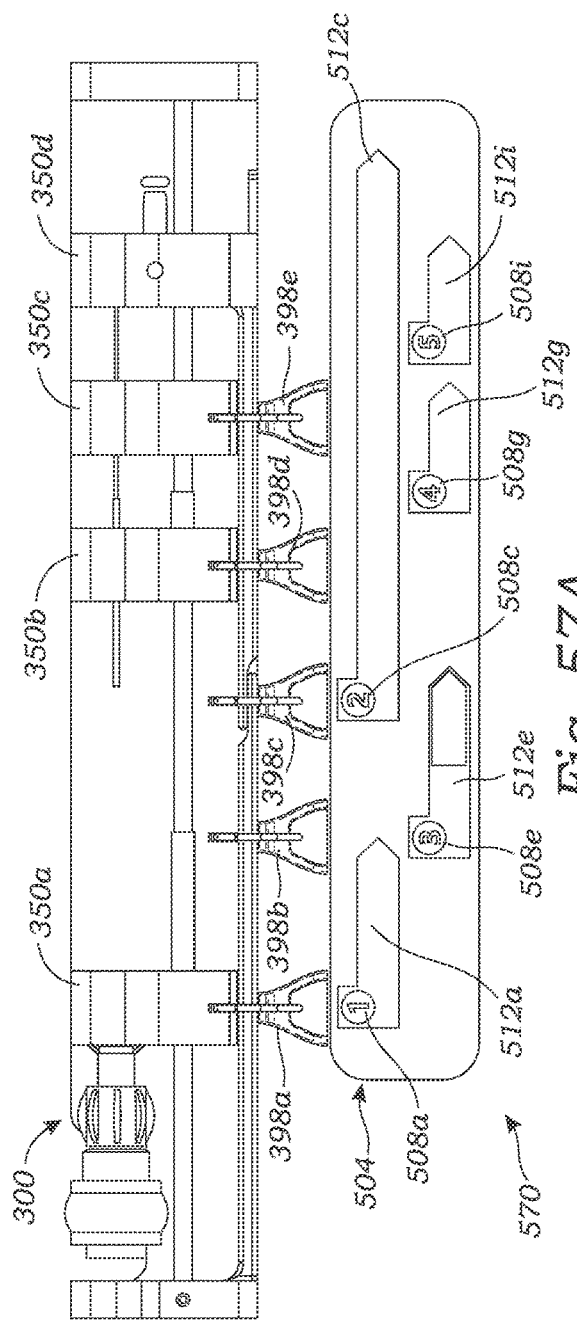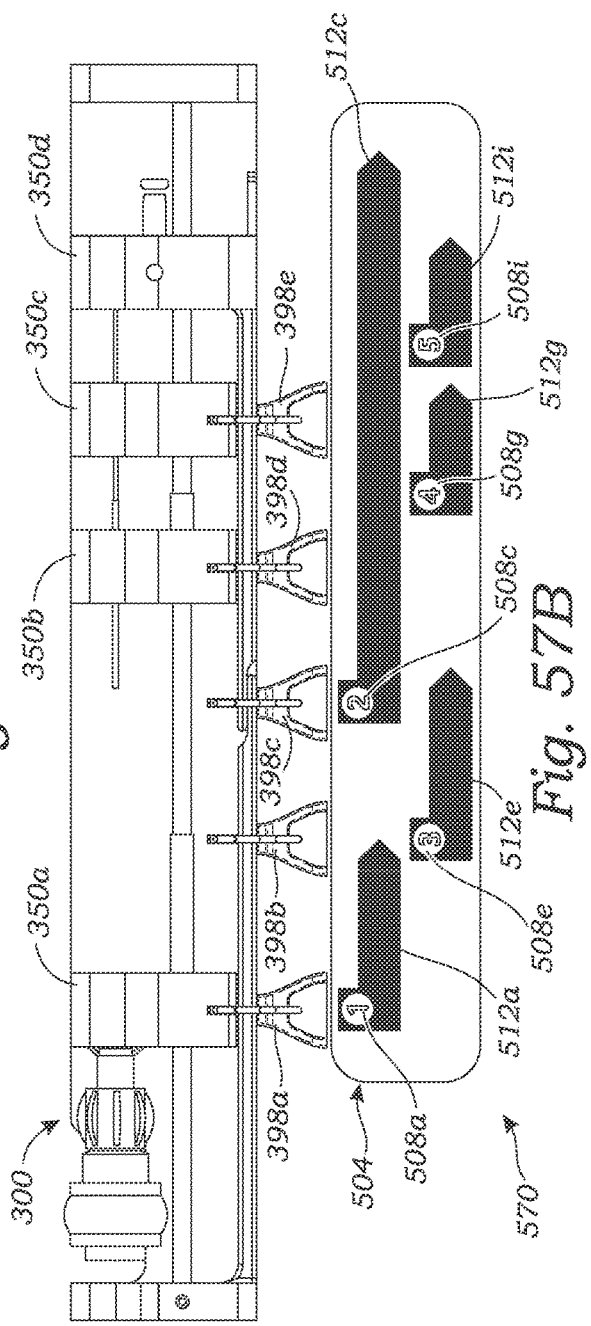

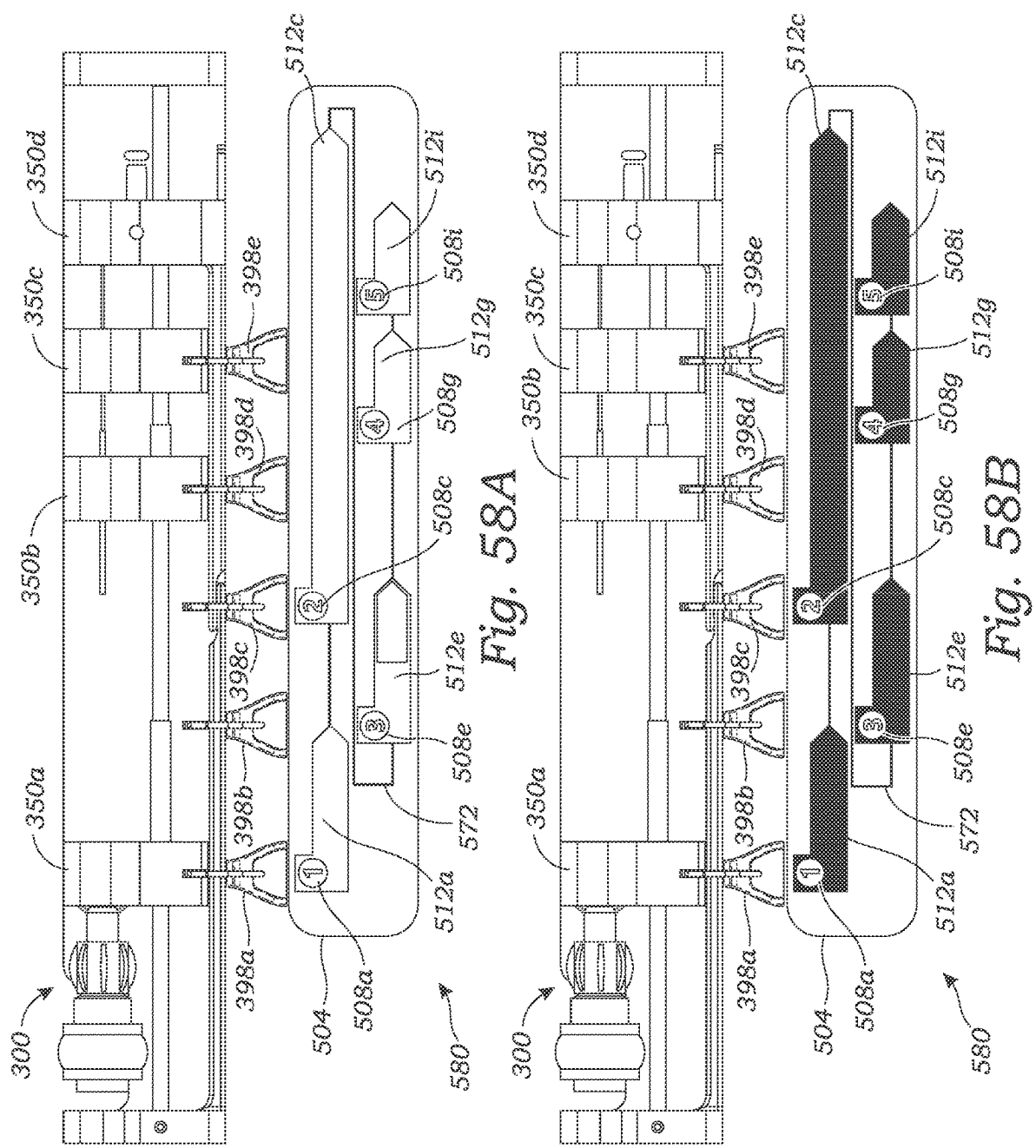

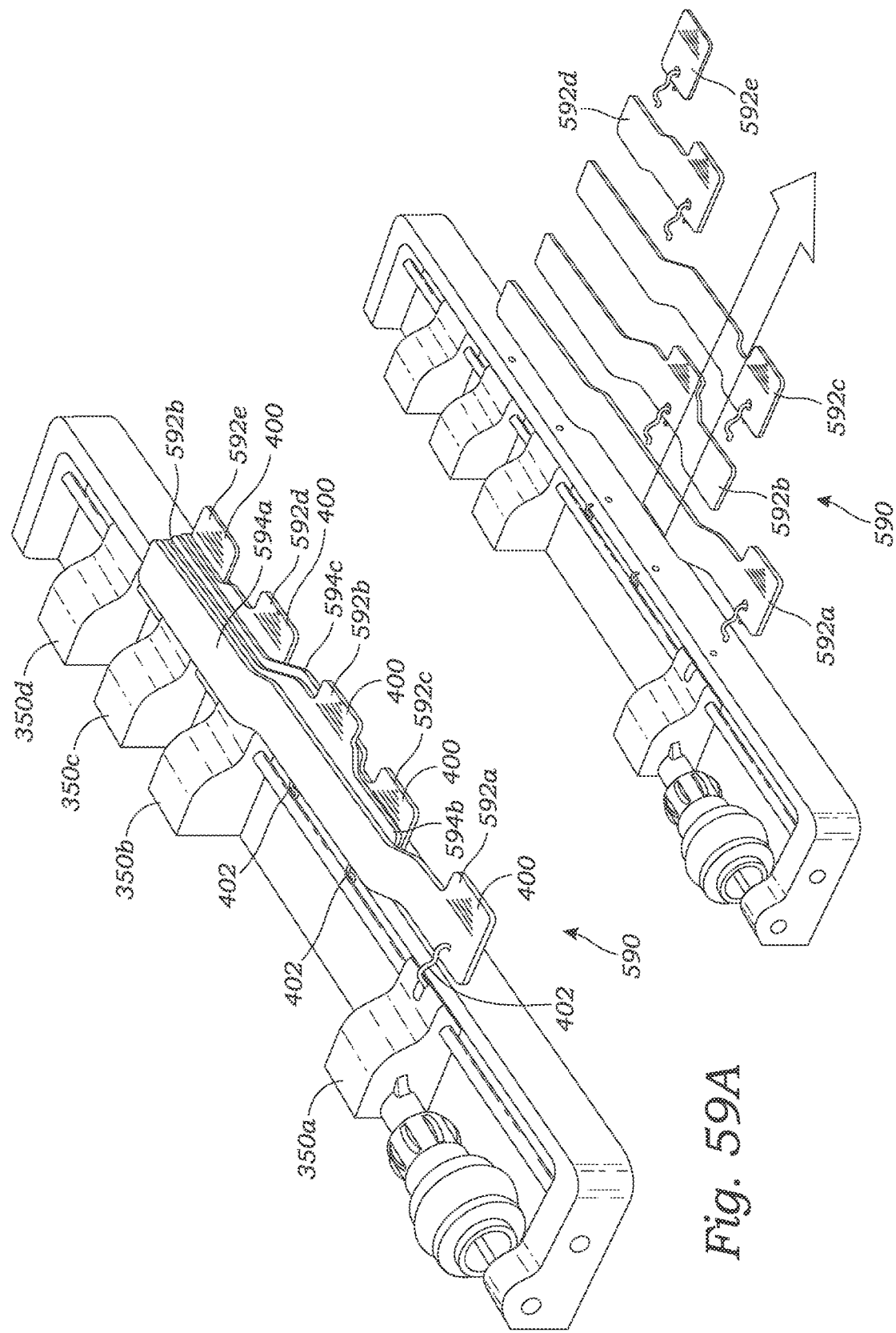

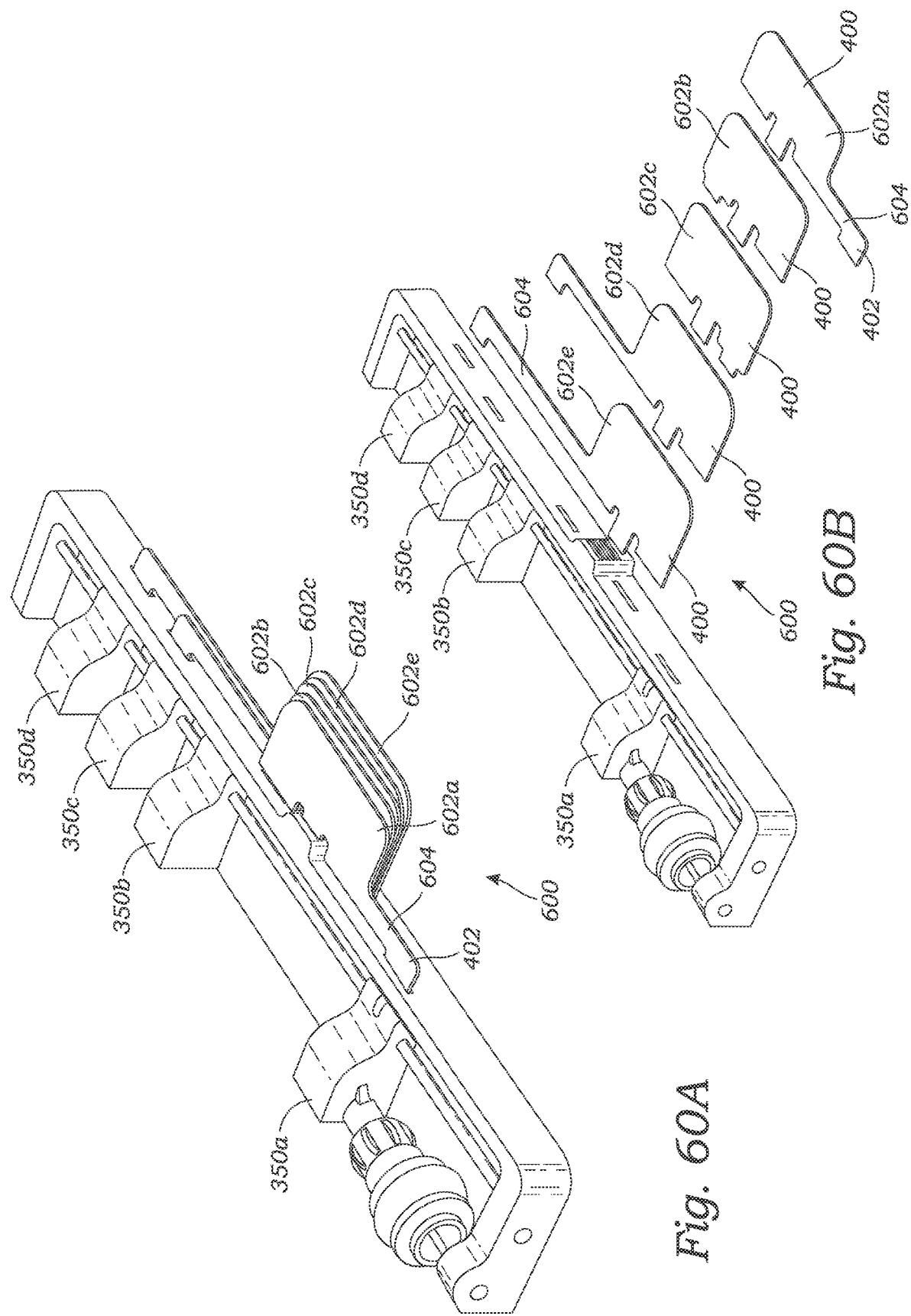

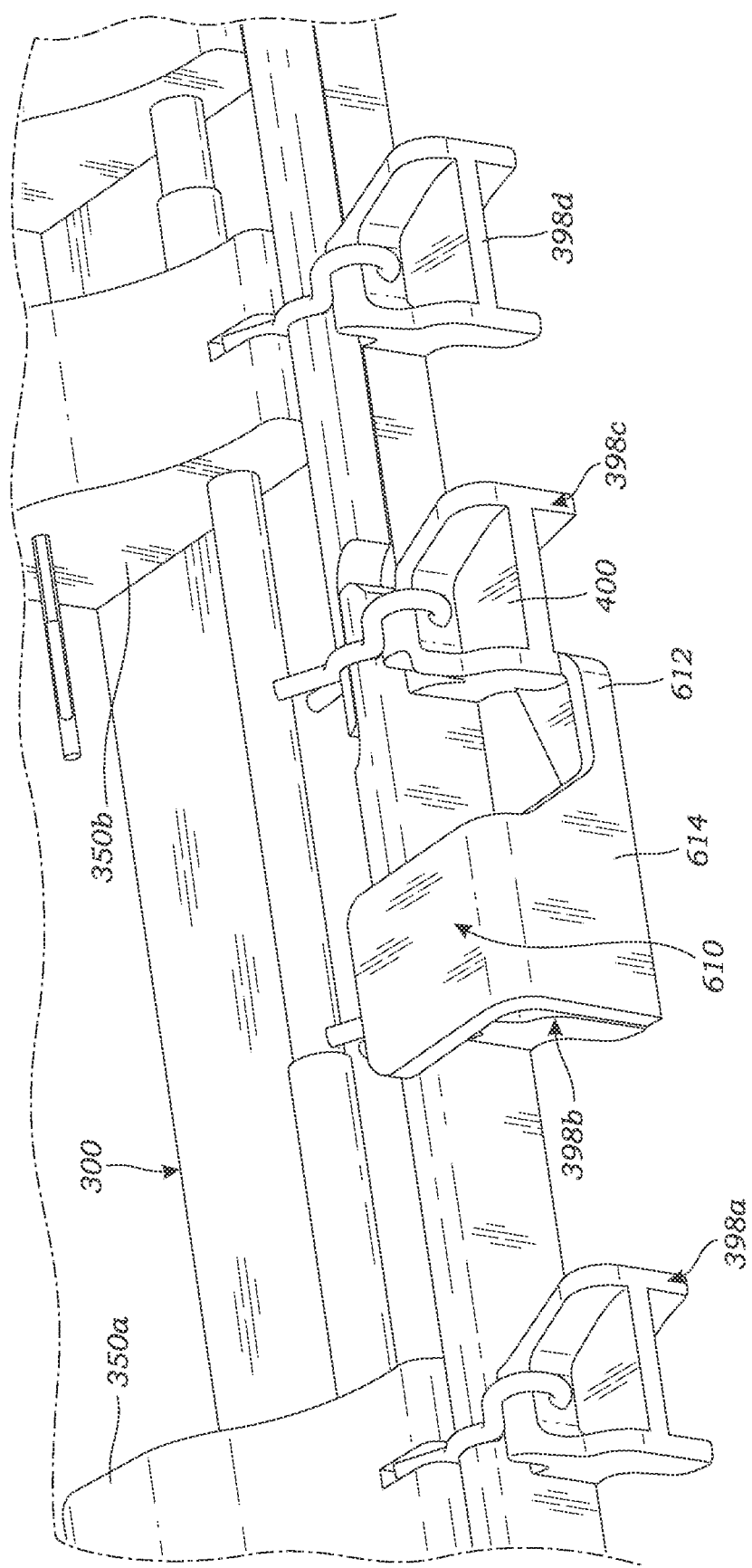

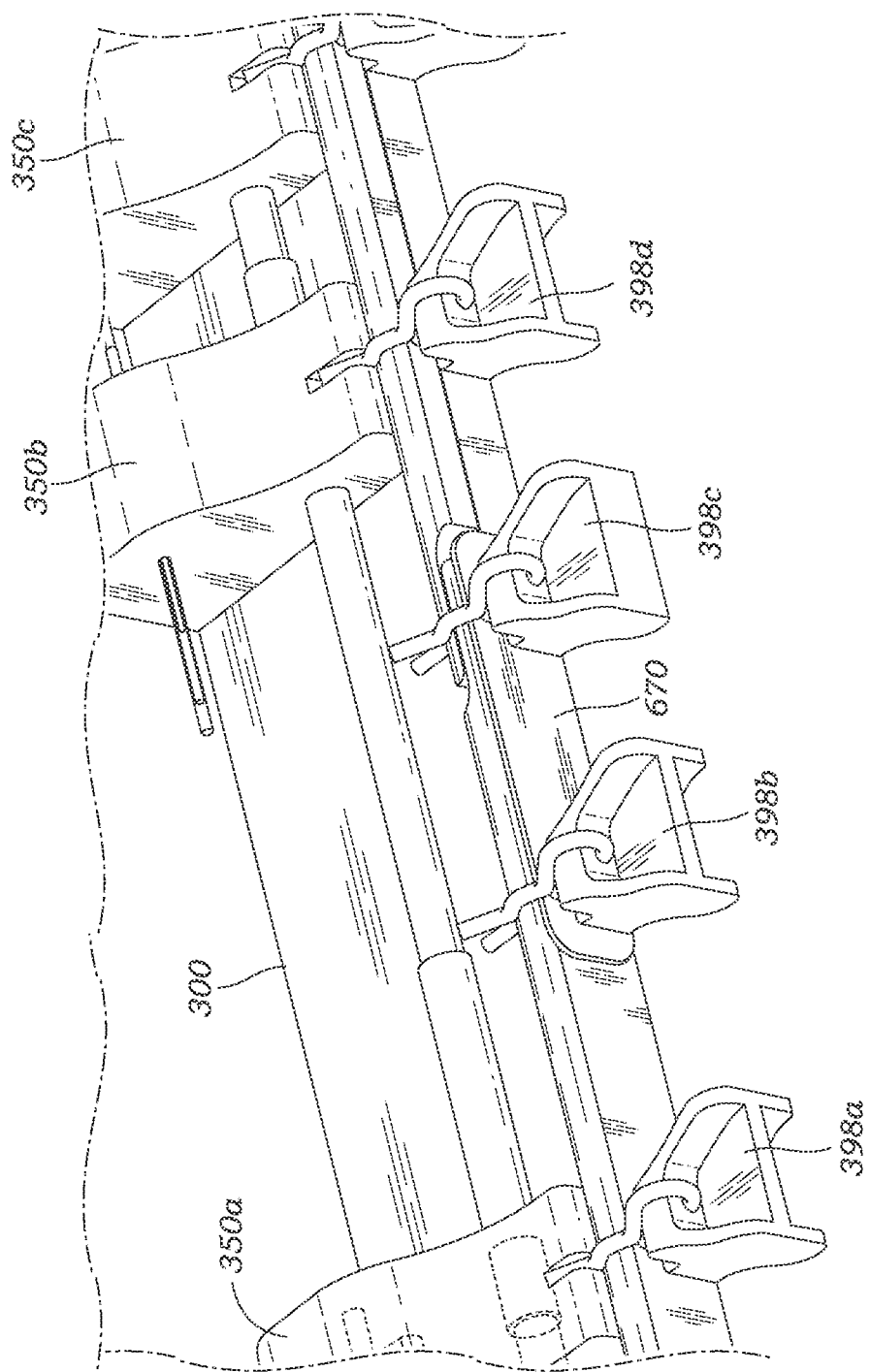

APPARATUS AND METHODS FOR LOADING AN ENDOVASCULAR IMPLANT INTO A DELIVERY CATHETER

RELATED APPLICATION DATA

The present application claims the benefit or priority under 35 U.S.C. § 119 to Provisional Application Ser. No. 62/965,105, filed on Jan. 23, 2020.

FIELD OF THE INVENTION

The present disclosure pertains to apparatus and methods for transferring or loading an endovascular implant, such as a cerebrospinal fluid (CSF) shunt, from its packaging into a delivery catheter that accesses a patient's venous system.

BACKGROUND

Hydrocephalus is one of the most common and important neurosurgical conditions affecting both, children and adults. Hydrocephalus, meaning "water on the brain," refers to the abnormal CSF accumulation in the brain. The excessive intracranial pressure resulting from hydrocephalus can lead to a number of significant symptoms ranging from headache to neurological dysfunction, coma, and death. Cerebrospinal fluid is a clear, physiologic fluid that bathes the entire nervous system, including the brain and spinal cord. In normal patients, arachnoid granulations straddle the surface of the intracranial venous drainage system of the brain and reabsorb CSF present in the subarachnoid space into the venous system. Approximately 450 mL to 500 mL of CSF is produced and reabsorbed each day, enabling a steady state volume and pressure in the intracranial compartment of approximately 8-16 cm $H_2O$. This reabsorption pathway has been dubbed the "third circulation," because of its importance to the homeostasis of the central nervous system. Hydrocephalus occurs most commonly from the impaired reabsorption of CSF, and in rare cases, from its overproduction. The condition of impaired reabsorption is referred to as communicating hydrocephalus. Hydrocephalus can also occur as a result of partial or complete occlusion of one of the CSF pathways, such as the cerebral aqueduct of Sylvius, which leads to a condition called obstructive hydrocephalus. A positive pressure gradient between the intracranial pressure of the subarachnoid space and the blood pressure of the venous system may contribute to the natural absorption of CSF through arachnoid granulations.

Prior art techniques for treating communicating hydrocephalus (and in some cases, pseudotumor cerebri and intracranial hypertension) rely on ventriculoperitoneal shunts ("VPS" or "VP shunt" placement), a medical device design introduced more than 60 years ago. VPS placement involves an invasive surgical procedure performed under general anesthesia, typically resulting in hospitalization ranging from two to four days. The surgical procedure typically involves placement of a silicone catheter in the frontal horn of the lateral ventricle of the brain through a burr hole in the skull. The distal portion of the catheter leading from the lateral ventricle is then connected to a pressure or flow-regulated valve, which is placed under the scalp. A separate incision is then made through the abdomen, into the peritoneal cavity, into which the proximal portion of a tubing catheter is placed. The catheter/valve assembly is then connected to the tubing catheter, which is tunneled subcutaneously from the neck to the abdomen.

VPS placement is a very common neurosurgical procedure, with estimates of 55,000-60,000 VPS placements occurring in the U.S. each year. While the placement of a VP shunt is typically well-tolerated by patients and technically straightforward for surgeons, VP shunts are subject to a high rate of failure in treated patients. Complications from VP shunt placement are common with a one-year failure rate of approximately 40% and a two-year shunt failure rate reported as high as 50%. Common complications include catheter obstruction, infection, over-drainage of CSF, and intra-ventricular hemorrhage.

There has been little change in the design of basic VPS hardware since its introduction in 1952. However, this status quo is finally and dramatically changing with the introduction by the present applicant, CereVasc, LLC, located in Auburndale, Mass., of a cerebrospinal fluid shunt configured for deployment through a venous system of the patient, the shunt including a proximal portion, a distal portion having a distal anchoring mechanism, and a shunt lumen in fluid communication with one or more distal openings in the distal portion and one or more proximal openings in the proximal portion. A delivery (i.e., shunt implantation) system is also provided and configured for creating an anastomosis between an inferior petrosal sinus and a CSF-filled subarachnoid space of the patient, and for deploying the shunt in the anastomosis with the distal portion of the shunt positioned in the subarachnoid space, such that, when the shunt is deployed in the anastomosis, CSF flows from the subarachnoid space through the one or more distal openings, lumen, and one or more proximal openings of the shunt, respectively, into the venous system of the patient (e.g., near the jugular bulb).

Various embodiments of the CereVasc endovascular shunt and delivery/implantation system are disclosed and described in each of U.S. Pat. No. 9,387,311, U.S. Patent Application Publication No. 20180207412, and PCT Application Publication No. WO 2018/071600, which are all hereby incorporated by reference into the present application for all that they teach and disclose.

SUMMARY

Disclosed and described herein are embodiments of an innovative tool for preparing and loading an endovascular shunt assembly, into a delivery catheter for introducing the endovascular shunt assembly into a patient's venous system. Although the disclosed tool is specifically arranged for loading a CSF fluid shunt, it should be understood that the disclosed tool and methods of using same may be modified and used to load any suitable endovascular medical device, and is not limited to CSF shunts.

BRIEF DESCRIPTION OF THE DRAWINGS

The foregoing and other aspects of embodiments are described in further detail with reference to the accompanying drawings, wherein like reference numerals refer to like elements and the description for like elements shall be applicable for all described embodiments wherever relevant:

FIG. 12A is an enlarged, perspective view of the shroud of FIG. 12, according to one embodiment of the disclosed inventions;

FIG. 13 is a side, perspective view of a claw assembly for loading a shunt assembly using the shunt loader of FIG. 1, according to one embodiment of the disclosed inventions;

FIG. 14 is a side, perspective view of the shunt assembly of FIG. 11 and the claw assembly of FIG. 13 for use with the shunt loader of FIG. 1, wherein the claw is in an open position, according to one embodiment of the disclosed inventions;

FIG. 15 is a side, perspective view of the shunt assembly of FIG. 11 and the claw assembly for use with the shunt loader of FIG. 1, wherein the claw is in a closed position, according to one embodiment of the disclosed inventions;

FIG. 27 is a table showing the magnitude and direction of movement of each of the guide bosses and components for each of the steps 1-9 of a method of using the shunt loader, according to one embodiment of the disclosed inventions;

FIG. 28A is an enlarged, side view of the shunt assembly of FIG. 28, perspective view of a portion of the shunt loader and shunt assembly of FIG. 1, according to one embodiment of the disclosed inventions;

FIG. 28B is alternate enlarged, side view of the portion of the shunt loader and shunt assembly shown FIG. 28A, with the delivery catheter rotated 180° from the view shown in FIG. 28A, better depicting the needle guard, delivery catheter, and delivery catheter carriage, respectively;

FIG. 49 is a table showing the magnitude of movement of each of the guide bosses and components for each of the steps 1-5 of a method of using the shunt loading system of FIG. 28, according to one embodiment of the disclosed inventions.

FIGS. 56A and 56B are a plan views of another instructional graphic adjacent a schematic view of the shunt loading system of FIG. 28, according to one embodiment of the disclosed inventions;

FIGS. 57A and 57B are plan views of another instructional graphic adjacent a schematic view of the shunt loading system of FIG. 28, according to one embodiment of the disclosed inventions;

FIGS. 58A and 58B are plan views of another instructional graphic adjacent a schematic view of the shunt loading system of FIG. 28, according to one embodiment of the disclosed inventions;

FIGS. 59A and 59B are perspective views of an alternative design for pull-tabs for shown on a schematic view of the shunt loading system of FIG. 28, according to one embodiment of the disclosed inventions;

FIGS. 60A and 60B are perspective views of another alternative design for pull-tabs for shown on a schematic view of the shunt loading system of FIG. 28, according to one embodiment of the disclosed inventions;

FIG. 61 is a partial perspective view of the shunt loading system of FIG. 28 having a retainer blocking device for preventing incorrect removal of a retainer, according to one embodiment of the disclosed inventions;

FIG. 67 is a partial perspective view of the shunt loading system of FIG. 28 having an alternative design for a retainer blocking device for preventing incorrect removal of a retainer, according to one embodiment of the disclosed inventions.

DETAILED DESCRIPTION OF THE ILLUSTRATED EMBODIMENTS

FIGS. 1-10 illustrate an endovascular shunt loader 100 for preparing an endovascular shunt assembly 102 for loading into a delivery catheter (not shown). The delivery catheter may then be used to insert the shunt assembly 102 into the vascular system of a patient, advance the shunt assembly 102 through the vascular system to a desired implantation location, and implant the shunt assembly 102 in the patient.

Figure 11:
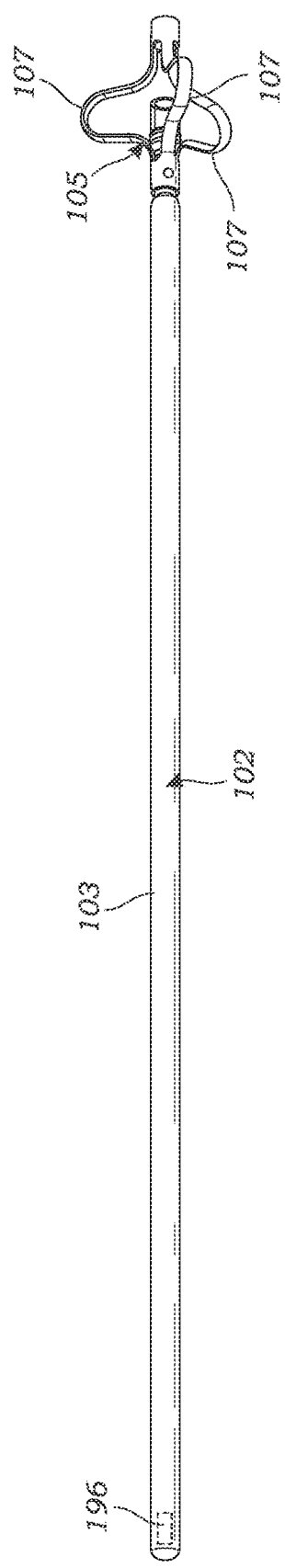
FIG. 11 is a side, perspective view of a shunt assembly which can be loaded using the shunt loader of FIG. 1, according to one embodiment of the disclosed inventions.

Referring to FIGS. 1A, 11, 12 and 16, in the exemplary embodiment described herein, the shunt assembly 102 includes a shunt body 103, a malecot 105 attached to the distal end of the shunt body 103, and a tubular shroud 168 into which the shunt body 103 is disposed. Referring to FIG. 11, the shunt body 103 is a tube formed of an elastic material, such as a polymer material. The malecot 105 is an expandable device having a plurality of radially compressible and expandable fingers 107. The fingers 107 of the malecot 105 are biased to a radially expanded state in their relaxed (unconstrained) condition. The fingers 107 of the malecot 105 can be compressed to a radially compressed state in a constrained delivery profile and self-expands to the expanded state when released from the constraint.

Figure 12:
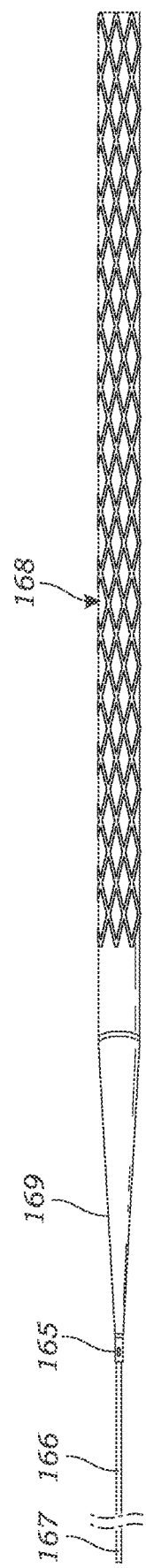
FIG. 12 is a side, perspective view of a shroud for loading a shunt assembly using the shunt loader of FIG. 1, according to one embodiment of the disclosed inventions.

Turning to FIGS. 12 and 12A, the tubular shroud 168 has a tapered portion 169 at its proximal end. A shroud tether 166 having a proximal end 167 and a distal end 165 is attached to the shroud 168. As used herein, the terms "proximal," "distal" and their other forms, are relative terms in which in the orientation of the figures, to the left is "proximal" and to the right is "distal." In other words, a first element which is to the left of a second element is "proximal" to the second element, and the second element is "distal" to the first element. Similarly, if a first element extends to the left as shown in the figures, the first element extends "proximally." The distal end 165 of the shroud tether 166 is attached to the proximal end of the shroud 168.

It is understood that the shunt loader 100 and method of using the shunt loader 100 is not limited to loading a shunt assembly 102 as described herein, but may be used to load any suitable endovascular device, such as a shunt, stent, or other implantable medical device.

As explained above, in some cases, an endovascular shunt may have a design which requires it to be prepared for use just prior to use. For example, the shunt assembly 102 may have components which are better or more easily sterilized, shipped and/or stored in a preparatory configuration and then prepared for use just prior to being used. As some non-limiting examples, the shunt assembly 102 may include components made of shape memory materials, elastic materials or the like which are placed in a stressed, compressed, stretched, or otherwise non-relaxed condition when prepared for insertion into a patient. Such components may be damaged or degrade if retained in this condition during shipping and/or storage. Furthermore, it may be useful to manipulate the device just prior to use in order to flush air from the shunt assembly 102 in preparation for insertion into a patient.

Accordingly, the disclosed inventions are directed to a shunt loader 100 which manipulates the shunt assembly 102 to prepare the shunt assembly 102 for installation into a delivery catheter which inserts and implants the shunt assembly 102 in a patient. The shunt loader 100 comprises a drive carriage 104 slidably mounted to a guide base 106 such that the drive carriage 104 and guide base 106 are movable relative to one another along a longitudinal axis 101 of the loader 100. In the embodiment of FIGS. 1-10, the drive carriage 104 moves linearly relative to the guide base 106. However, it is understood that the guide base 106 may be moved linearly relative to the drive carriage 104 to achieve the same result.

Figure 1:
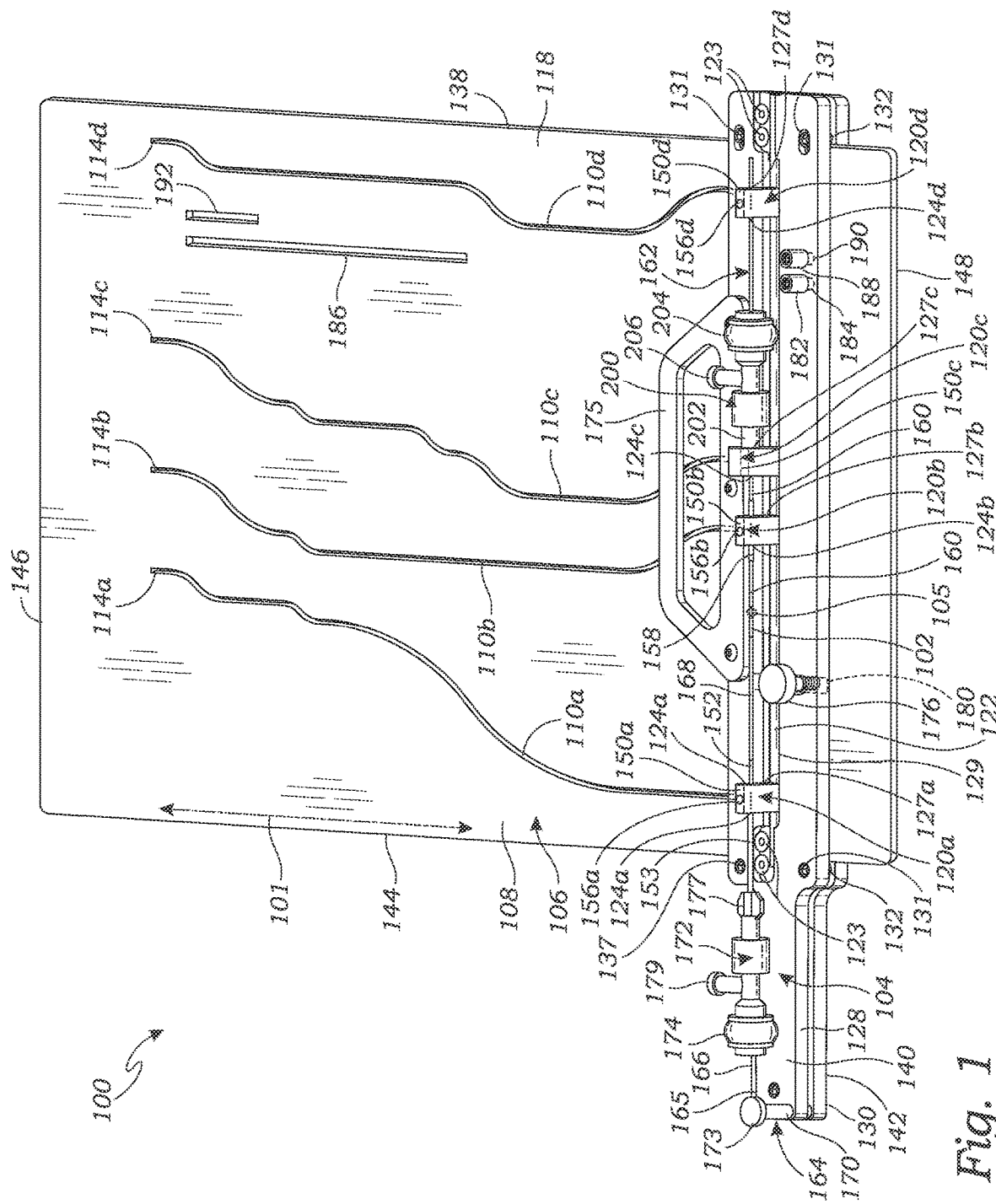
FIG. 1 is a front perspective view of a shunt loader and shunt assembly installed thereon in an initial configuration, according to one embodiment of the disclosed inventions.
Figure 1A:
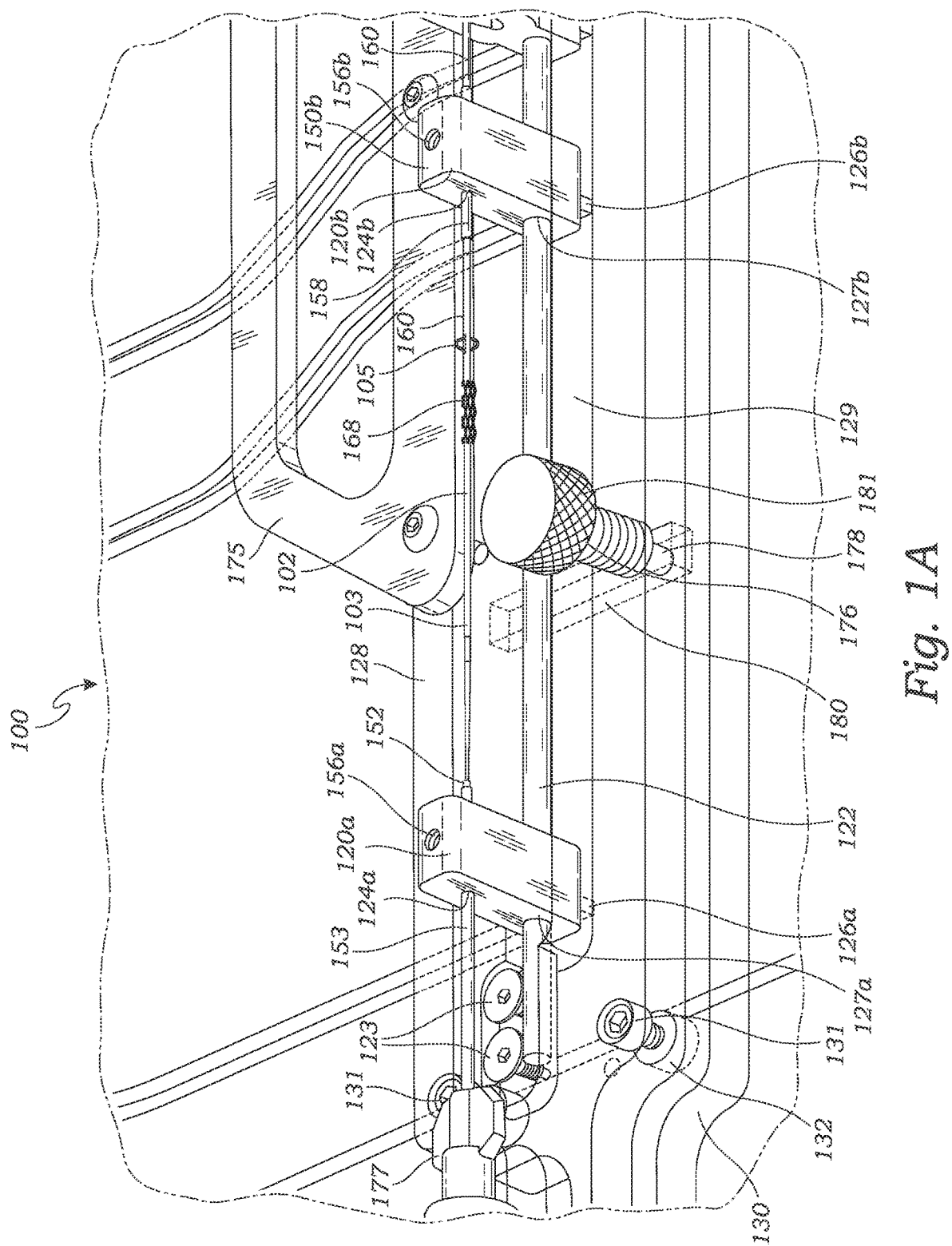
FIG. 1A is an enlarged, perspective view of a portion of the shunt loader and shunt assembly of FIG. 1.

Referring to FIGS. 1 and 1A, the guide base 106 comprises a flat plate 108 having a top surface 118 and a bottom surface (not shown), a right side 138 and a left side 144, and a top side 146 and a bottom side 148. The guide base 106 has plurality of guide slots 110a, 110b, 110c, and 110d. Each of the guide slots 110 extends from a bottom end 112a, 112b, 112c, and 112d (see FIG. 3) near the bottom side 148 of the plate 108 to a top end 114a, 114b, 114c, and 114d, respectively. Each of the guide slots 110a, 110b, 110c and 110d follows a respective predetermined path configured to guide the lateral movement of a respective guide boss 120a, 120b, 120c, and 120d of the drive carriage 104.

The drive carriage 104 is slidably mounted to the guide base 106 and extends laterally across the guide base 106. The drive carriage 104 includes a top plate 128 which rests on the top surface 118 of the guide base 106 and a bottom plate 130 opposing the top plate 128 such that the guide base 106 is sandwiched between the top plate 128 and bottom plate 130. The top plate 128 is attached to the bottom plate 130 by eight bolts 131 extending through the top plate 128 and the bottom plate 130 on opposing sides of the plate 108. Each of the bolts 131 screws into a respective spacer/plate retainer 132 between the top plate 128 and bottom plate 130. The spacer/plate retainers 132 have a height which spaces the top plate 128 and bottom plate 130 slightly greater than the thickness of the plate 108. The eight bolts 131 and spacer/plate retainers 132 are laterally spaced just wider than the plate 108 such that the sides 138 and 144 of the plate 108 are retained between the four spacer/plate retainers 132. Two of the attachment holes in the top plate 128 and bottom plate 130 are elongated laterally to allow for adjustability of the distance between the spacer/plate retainers 132 and the sides 138 and 144 of the plate 108. The two attachment holes on the right side of the guide base 106 are elongated laterally in the embodiment shown in FIGS. 1-10.

Each of the top plate 128 and bottom plate 130 have the same or substantially similar perimeter shape. Each of the top plate 128 and bottom plate 130 extend laterally across the guide base 106. The right end 134 of the top plate 128 and the right end 136 of the bottom plate extend slightly beyond the right side 138 of the guide base 106. The left side of each of the top plate 128 and bottom plate 130 have a respective extension 140, 142 which extends beyond the left side 144 of the guide base 106.

Figure 1B:
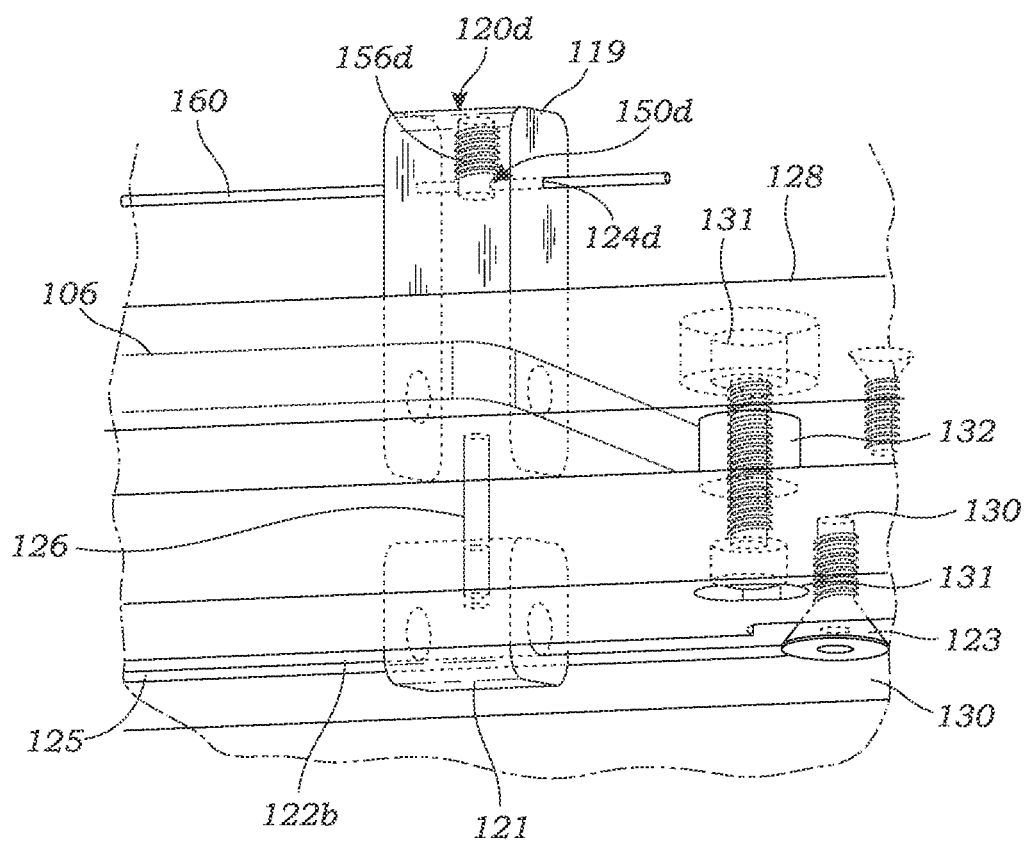
FIG. 1B is an enlarged, side, perspective view of a portion of the shunt loader and shunt assembly of FIG. 1.

The drive carriage 104 has a plurality of guide bosses 120 (a first guide boss 120a, a second guide boss 120b, a third guide boss 120c, and a fourth guide boss 120d). As shown in the enlarged view of FIG. 1B showing one of the guide bosses 120d, each guide boss 120 has an upper component 119 and a lower component 121 connected by a respective guide pin 126. Each guide pin 126a, 126b, 126c, 126d extends between respective upper and lower components 119 and 121 and through the respective guide slot 110.

The upper and lower components 119 and 121 are slidably mounted on a respective boss rod 122a and 122b. Each of the upper components 119 of the guide bosses 120 has an aperture 127 which slidably receives the boss rod 122a, and each of the lower components 121 has an aperture which slidably receives the boss rod 122b, allowing each guide boss 120 to slide along the boss rods 122a and 122b to move laterally back and forth across the drive carriage 104 and the guide base 106. The guide bosses 120a, 120b, 120c and 120d are spaced apart laterally on the boss rods 122a and 122b. The top plate 128 has a recess 129 extending laterally relative to the longitudinal axis 101 across the top plate 128. The boss rod 122a is disposed in the recess 129 and also extends laterally across the top plate 128. The boss rod 122a is mounted to the top plate 128 using four fasteners 123 (e.g., screws). The bottom plate 130 has a recess 125 extending laterally relative to the longitudinal axis 101 across the bottom plate 130. The boss rod 122b is disposed in the recess 125 and also extends laterally across the bottom plate 130. The boss rod 122b is mounted to the bottom plate 130 using four fasteners 123 (e.g., screws).

Each of the guide bosses 120a, 120b, 120c and 120d has a respective retainer 150a, 150b, 150c, and 150d. Each retainer 150 is configured to receive and retain a shunt loader component. The shunt loader components include the components of the shunt assembly 102, and loading components used to manipulate the components of the shunt assembly 102 during the loading process. The guide boss 120a holds and moves a transfer tube 152 over the shunt assembly 102 during use of the shunt loader 100.

Figure 1C:
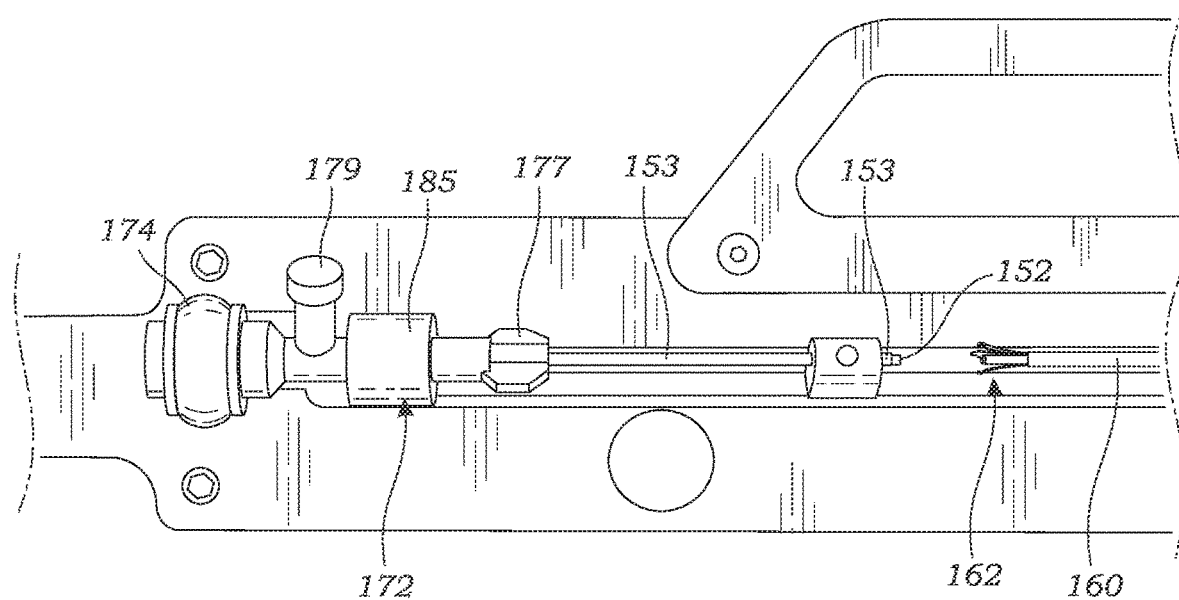
FIG. 1C is an enlarged, perspective view of the assembled transfer tube and transfer support tube of the of the shunt loader and shunt assembly of FIG. 1.
Figure 1D:
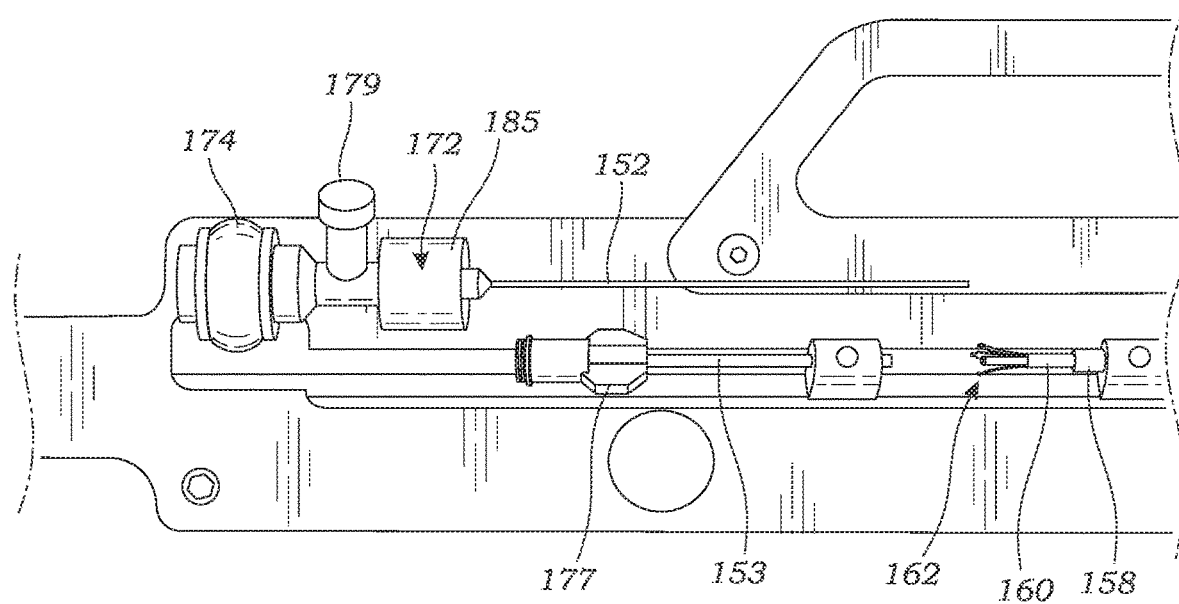
FIG. 1D is an enlarged, perspective view of the disassembled transfer tube and transfer support tube of the of the shunt loader and shunt assembly of FIG. 1.

As shown in FIGS. 1A, 1C and 1D, the transfer tube 152 is inserted through, and connected to, a transfer support tube 153 (see FIGS. 1A and 1B). The transfer tube is connected to the transfer support tube using a second fitting 177 (Luer fitting 177), or other suitable connection means. Thus, the retainer 150a is configured to retain the transfer support tube 153, and in turn the transfer tube 152 which is connected to the transfer support tube 153. The retainer 150a has a retainer hole 124a through which the transfer support tube 152 is inserted and a set screw 156a which can be tightened to securely hold the transfer support tube 152 to the retainer 150a.

The guide boss 120b holds and moves a malecot holding tube cover 158. The malecot holding tube cover 158 is one of the loading components. The guide boss 120b has a retainer 150b which is configured to retain the malecot holding tube cover 158. The retainer 150b has a retainer hole 124b through which the malecot holding tube cover 158 is inserted and a set screw 156b which can be tightened to securely hold the malecot holding tube cover 158.

The guide boss 120c holds and moves a malecot holding tube 160, which is also one of the loading components. The retainer 150c is configured to retain the malecot holding tube 160. The retainer 150c has a retainer hole 124c through which the malecot holding tube 160 is inserted. The malecot holding tube 160 may be bonded into the retainer hole 124c with adhesive or it may be secured to the retainer 150c using a set screw (not shown) which can be tightened to securely hold the malecot holding tube cover 158 to the retainer 150c.

The guide boss 120d holds and moves a claw assembly 162. The guide boss 120d has a retainer 150d which is configured to retain the claw assembly 162. The retainer 150d has a retainer hole 124d through which the claw assembly 162 is inserted and a set screw 156d which can be tightened to securely hold the claw-shaft 162 to the retainer 150d.

Referring to FIG. 13, the claw assembly 162 includes a claw 161 attached to the proximal end of a shaft 171. The claw 161 has a plurality of prongs 159 (in this case 3 prongs) and is biased to an open position as shown in FIGS. 13 and 14. In other words, the claw 161 expands to the open position when the prongs 159 are not forced to the collapsed position as shown in FIG. 15. In the use of the shunt loader 100, the claw 161 is closed when it is inserted into the malecot holding tube 160 such that the malecot holding tube 160 collapses the claw 161. Then, the claw 161 self-expands to the open position when it is removed from the malecot holding tube 160. As shown in FIGS. 14 and 15, the claw 161 is configured such that the prongs 159 of the claw 161 fit into slots between the fingers 107 of the malecot 105 when the claw 161 is closed onto the distal end of the malecot 105, as shown in FIG. 15. Thus, when the claw assembly 162 is inserted into the malecot holding tube 160 with the prongs 159 properly aligned with the malecot 105, the claw 161 grasps the malecot 105. The proximal end of the shaft 171 is configured to bear against the distal end of the malecot 105 such that the claw assembly 162 can push the malecot 105 and shunt body 103 proximally when the claw assembly 162 is moved proximally.

The drive carriage 104 also has a shroud tether retainer 164 disposed on the left end of the extension 140 of the top plate 128 which is configured to retain the shroud tether 166. The shroud tether retainer 164 has a slot 170, through which the shroud tether 166 is inserted, and a thumb screw 173 which can be tightened and loosened to close and open the slot 170 to retain and release the shroud tether 166.

The drive carriage 104 has a handle 175 attached to the upper side of the top plate 128. The handle 175 can be used to pull the drive carriage 104 to move the drive carriage 104 longitudinally relative to the guide base 106 during the shunt loading procedure.

The drive carriage 104 has a flush stop 176 which is mounted to the top plate 128. The flush stop 176 has a spring-loaded plunger 178 which extends through the top plate 128 and into a flush stop slot 180 in the guide base 106, when the drive carriage 104 is in the "Step 1" position (as shown in FIG. 1), as described in more detail herein. The spring-loaded plunger 178 has a spring which biases the plunger 178 downward into the flush stop slot 180. The flush stop slot 180 extends longitudinally from a starting position of the drive carriage (see FIG. 1) to the flushing position of the drive carriage (see FIG. 2). The flush stop 176 has a finger knob 181 attached to the plunger 178 for pulling the plunger 178 upward out of the flush stop slot 180 to allow the drive carriage 104 to be moved longitudinally upward past the flush stop slot 180.

The drive carriage 104 has a first anti-reversal stop 182 laterally aligned with a first anti-reversal slot 186 in the guide base 106. The first anti-reversal stop 182 has a spring-loaded plunger 184 which extends into the first anti-reversal slot 186 when the drive carriage 104 is near the end of "Step 4" as described in more detail herein. The plunger 184 has a spring which biases the plunger 184 downward into the first anti-reversal slot 186. Prior to the drive carriage 104 reaching the position of the first anti-reversal slot 186, the plunger 184 slides on the top surface of the guide base 106. When the drive carriage 104 reaches the position of the first anti-reversal slot 186, the plunger 184 extends downward into the first anti-reversal slot 186 thereby preventing the drive carriage 104 from being moved backward, but still allowing the drive carriage 104 to continue to move upward (forward) with the plunger 184 moving upward in the first anti-reversal slot 186.

The drive carriage 104 has a second anti-reversal stop 188 laterally aligned with a second anti-reversal slot 192 in the guide base 106. The second anti-reversal stop 188 has a spring-loaded plunger 190 which extends into the second anti-reversal slot 192 when the drive carriage 104 is in the position of "Step 8" as described in more detail herein. The plunger 190 has a spring which biases the plunger 190 downward into the second anti-reversal slot 192. Prior to the drive carriage 104 reaching the position of the second anti-reversal slot 192, the plunger 190 slides on the top surface of the guide base 106. When the drive carriage 104 reaches the position of the second anti-reversal slot 192, the plunger 190 extends downward into the second anti-reversal slot 192 thereby preventing the drive carriage 104 from being moved backward, but still allowing the drive carriage 104 to continue to move forward with the plunger 190 moving forward in the second anti-reversal slot 186.

Turning to FIGS. 1-10, 16-25 and 26-27, a method of using the shunt loader 100 to prepare a shunt assembly 102 for loading into a delivery catheter and insertion into a patient will now be described. FIGS. 16-25 illustrate the relative position of the shunt assembly 102 and loading components at each step of the loading method, without showing the shunt loader 100. It should be understood that FIGS. 16-25 show the components as they are positioned on the shunt loader 100 at each respective step of the shunt loading method.

As shown in FIG. 1, the drive carriage 104 is initially positioned at the bottom side 148 of the guide base 106 such that each of the guide bosses 120 are located at the bottom end 112 (i.e., the starting point) of the respective guide slots 110. Also, the shunt assembly 102, and loading components including the transfer support tube 153 and transfer tube 152, malecot holding tube cover 158, malecot holding tube 160 and claw assembly 162, are installed on the shunt loader 100 in the initial set-up of the shunt loader 100.

The transfer support tube 153 and transfer tube 152 are installed on the shunt loader 100 by inserting the transfer support tube 153, through the retainer hole 124a of the first guide boss 120a. The transfer support tube 153 is fastened to the first guide boss 120a by tightening the set screw 156a. The transfer tube 152 is threaded through the transfer support tube 153 from proximal to distal and connected to the transfer support tube 153 with the Luer fitting 177. Hence, the transfer tube 152 can be moved laterally by movement of the first guide boss 120a.

The distal end 165 of the shroud tether 166 is connected to the proximal end of the shroud 168. The shroud tether 166 is fastened to the shroud tether retainer 164 by threading the proximal end of the shroud tether 166 through the slot 170 with the thumb screw 173 loosened to open the slot 170 and then tightening the thumb screw 173 to close the slot 170 onto the shroud tether 166.

Figure 16:
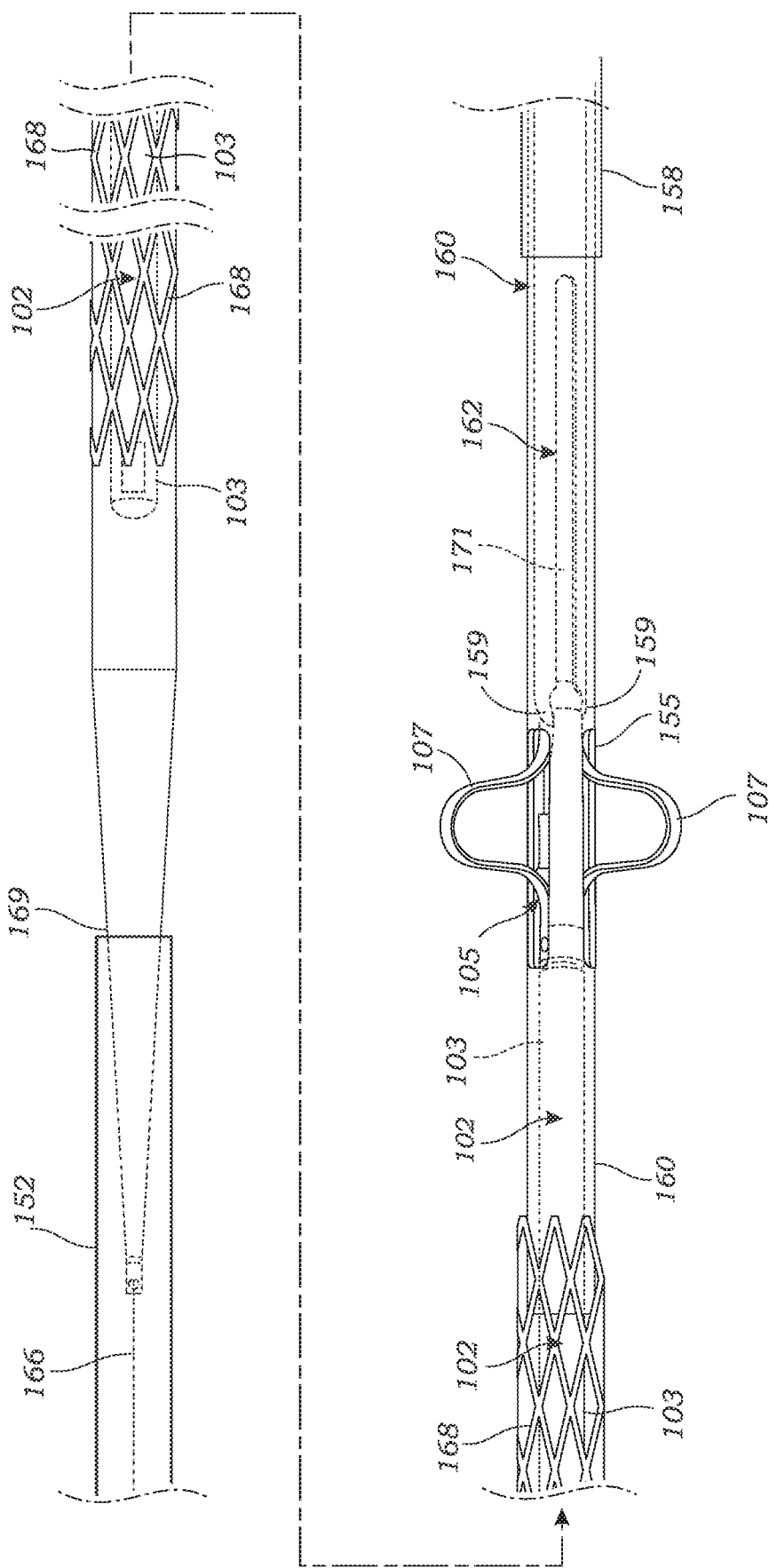
FIGS. 16-25 are side views depicting the shunt assembly and loading components at each of the Steps 1-9 of a method of using the shunt loader of FIG. 1, according to one embodiment of the disclosed inventions.

As shown in FIG. 16, in the initial set-up, the shroud 168 extends distally out of the distal end of the transfer tube 152 and extends over the shunt body 103 proximate to the malecot 105. The shroud 168 also extends over the proximal end of the malecot holding tube 160. The malecot 105 is disposed in the malecot holding tube 160. The malecot holding tube 160 is an elongated tube having a plurality of slots 155 on the proximal end of the malecot holding tube 160 configured to allow the fingers 107 of the malecot 105 to extend out through the slots 155 in their unconstrained, extended position (see FIG. 16). The malecot 105 is positioned with the malecot 105 aligned with the slots 155 such that the fingers 107 of the malecot 105 to extend out through the slots 155 in their unconstrained, extended position.

The malecot holding tube 160 has a distal portion which extends distally of the slots 155 and extends through the entire length of the malecot holding tube cover 158. The distal portion of the malecot holding tube 160 extends through the retainer hole 124c of the third guide boss 120c and is retained by the retainer 150c of the third guide boss 120c. Thus, the malecot holding tube 160 can be moved laterally by movement of the third guide boss 120c.

In the initial set-up of the shunt loader 100, the claw 161 of the claw assembly 162 is closed onto the malecot 105 such that the claw 161 grasps the malecot 105, as shown in FIG. 16.

Thus, in order to prepare the shunt loader 100 in its initial set-up with the claw 161 grasping the malecot 105, the claw assembly 162 is inserted through the malecot holding tube 160 so that the claw 161 extends past the proximal end of the malecot holding tube 160 such that the claw 161 expands to the open position. The malecot 105 and claw 161 are moved into close proximity, and the malecot holding tube 160 is moved proximally relative to the malecot 105 thereby closing the claw 161 such that the claw 161 grasps the malecot 105. The malecot holding tube 160 is moved proximally further relative to the malecot 105 and oriented such that the fingers 107 of the malecot 105 extend out through the slots 155, as described above.

In the initial set-up, the distal end of the shaft 171 of the claw assembly 162 and extend distally out of the distal end of the malecot holding tube cover 158. The distal end of the shaft 171 of the claw assembly 162 is inserted into the retainer hole 124d of the fourth guide boss 120d and the claw assembly 162 is fastened to the fourth guide boss 120d by tightening the set screw 156d. Thus, the claw assembly 162 can be moved laterally by lateral movement of the fourth guide boss 120d.

In the initial set-up, a first flushing adapter 172 is disposed on the transfer tube 152 The first flushing adapter 172 has a first fitting 174 (e.g., a Luer-lock fitting, compression fitting or other sealing fitting) on a proximal end of the adapter 172, a connector 185 on a distal end of the adapter 172 for connecting to the second fitting 177 and a first flush port 179 between, and in fluid communication with, the first fitting 174 and the connector 185. (See FIGS. 1C and 1D). The first flushing adapter 172 has fluid flow paths allowing flushing fluid to be injected into the first flush port 179 and to flow into the transfer tube 152 and flush air from the transfer tube 152.

Also, in the initial set-up, a second flushing adapter 200 is disposed on the malelcot holding tube 160. The second flushing adapter 200 has a first fitting 202 (e.g., a Luer-lock fitting, compression fitting or other sealing fitting) on a proximal end of the adapter 200, a second fitting 204 (e.g., a Luer-lock fitting, compression fitting or other sealing fitting) on a distal end of the adapter 200 and a second flush port 206 between, and in fluid communication with, the first fitting 202 and second fitting 204. The second flushing adapter 200 has fluid flow paths allowing flushing fluid to be injected into the second flush port 200 and to flow into the shunt assembly 102 and flush air from the shunt assembly 102.

In this initial set-up configuration of the shunt loader 100 with the shunt assembly 102 and shunt loading components installed on the shunt loader 100, the shunt body 103 is in a relaxed condition (i.e., it is not stretched or stressed), and the malecot 105 is open in its relaxed condition. However, in the loading and delivery configuration of the shunt assembly 102 (the configuration for loading into a delivery catheter and delivering the shunt assembly 102), the malecot 105 is in the closed position (compressed in the transfer tube 152) and the shunt body 103 is stretched to neck down the diameter of the shunt body 103. The delivery configuration reduces the diameter of shunt assembly 103 for advancing the shunt assembly 103 into a delivery catheter and/or through a patient's vascular system, and to insert the malecot 105 through an opening in the anatomy sized such that the malecot 105 in the open condition will not fit back through the opening thereby retaining the malecot 105 and shunt body 103 in the implanted position. The shunt loader 100 manipulates the shunt assembly 102 from the initial set-up configuration into the delivery configuration. In the delivery configuration, the stressing of the elastic material of the shunt body 103 and the memory material of the malecot 105 can degrade these components if left in the stressed condition for long periods of time, such as during storage and shipping. Therefore, the initial set-up configuration of the shunt assembly 102 is preferred over the loading configuration for shipping, storing, and/or sterilizing the shunt assembly 102 because the shunt body 103 and malecot 105 are in a relaxed condition, whereas in the loading configuration the shunt body 103 is stretched and the malecot 105 is compressed.

The shunt loader 100 may be used in at least two different manners. In one manner, the shunt loader 100 may be shipped and stored in the initial set-up configuration with the shunt assembly 102 and shunt loading components installed on the shunt loader 100. Then, just prior to use, the shunt loading procedure using the shunt loader 102 described herein may be performed to prepare the shunt assembly 102 for use. Alternatively, the shunt assembly 102 may be shipped without being installed on the shunt loader 100, and then, just prior to use of the shunt assembly 102, the shunt assembly 102 may be installed on the shunt loader 100 to the point of the initial set-up configuration. Then, the same shunt loading procedure using the shunt loader is performed to prepare the shunt assembly 102 for use.

Figure 26:
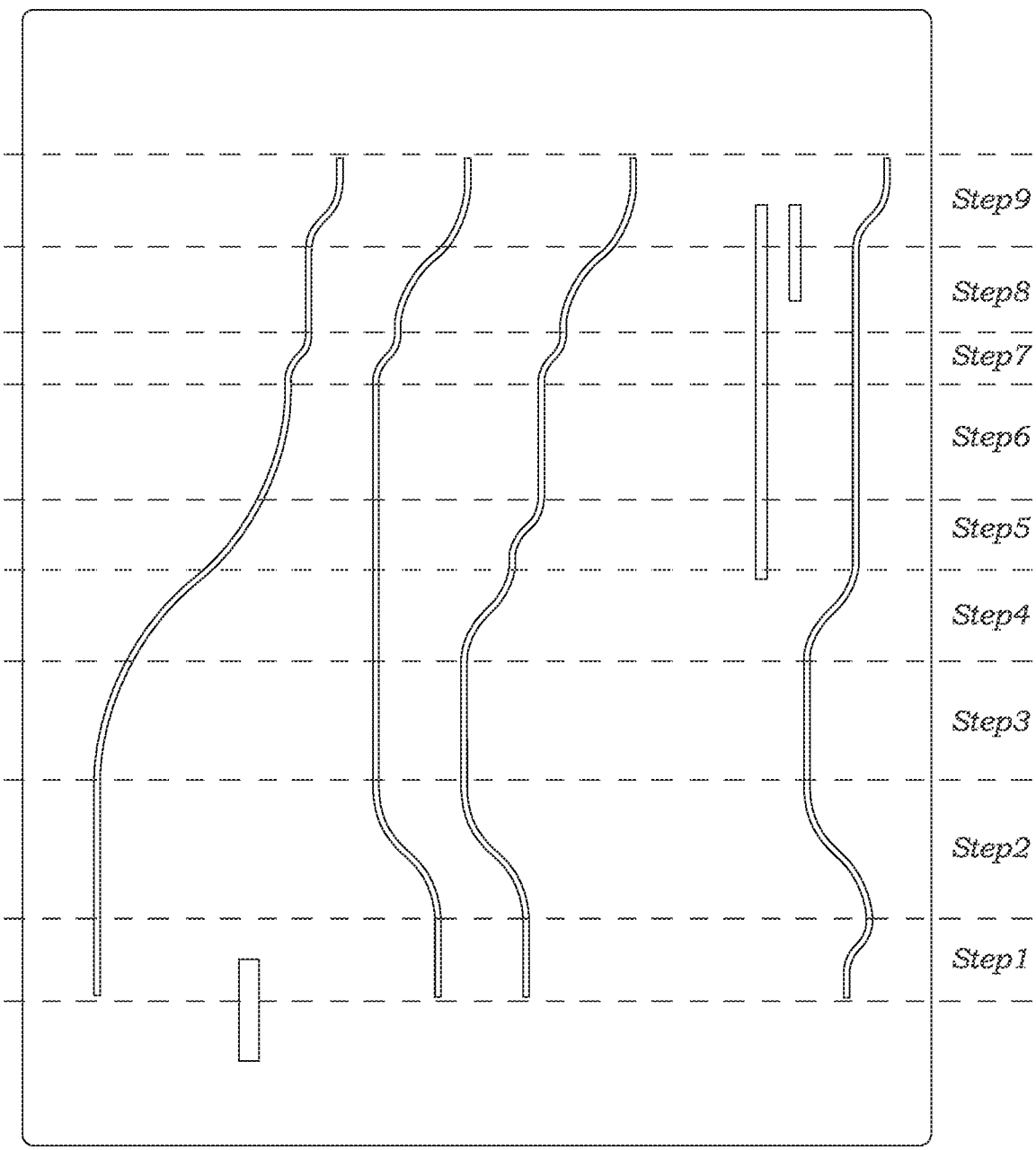
FIG. 26 is a top view of the guide base of the shunt loader of FIG. 1 showing the segments of each of the steps 1-9 of a method of using the shunt loader, according to one embodiment of the disclosed inventions.

The steps of the method for using the shunt loader 100 to prepare the shunt assembly 102 for loading into a delivery catheter will now be described. As shown in FIGS. 1 and 16, and as described above, the shunt loader 100 starts in the initial set-up configuration with the shunt assembly 102 and shunt loading components installed on the shunt loader 100. The drive carriage 104 is located at the bottom end of the guide base 106 with each of the guide pins 126a, 126b, 126c, 126d located at the bottom end 112a, 112b, 112c, 112d of the guide slots 110a, 110b, 110c, 110d, respectively. In Step 1 of the method, the drive carriage 104 is moved longitudinally upward relative to the guide base 106, as shown in FIG. 26. This may be accomplished by pulling on the handle 175. It is understood that the longitudinal movement of the drive carriage 104 relative to the guide base 106 may be accomplished by moving the drive carriage 104, the guide base 106 or a combination of both. Therefore, as used herein, description of moving the drive carriage 104 relative to the guide base 106 includes moving the drive carriage 104, the guide base 106 or both, unless it is explicitly stated otherwise, or implied by the particular context.

Referring to FIG. 26, the Step 1 portion of guide slot 110d curves laterally to the right. As shown in the table of FIG. 27, the Step 1 portion of guide slot 110d curves laterally to the right by 6 mm. The table of FIG. 27 shows the magnitude and direction of the movement of each of the guide bosses 120 in millimeters (mm) and the components retained by each respective guide boss 120 during each of the Steps 1-9 of the method for using the shunt loader 100 to prepare the shunt assembly 102 for use. In FIG. 27, a positive magnitude indicates movement of the respective guide boss 120 and attached component to the right and a negative magnitude indicates movement to the left. The specific magnitude of the movement of the guide bosses 120 in each of the steps of the method are exemplary for the preparation of a particular configuration and size of shunt assembly 102, and may vary depending on the design and size of the intravascular device being prepared using the shunt loader 100 and the method of using the shunt loader 100 for the particular shunt assembly.

As shown in FIGS. 26 and 27, in Step 1, the guide slots 110a, 110b, and 110c extend straight (i.e., parallel to the longitudinal axis 101), i.e., they have zero laterally movement. Hence, as the drive carriage 104 is moved upward in Step 1, the first guide boss 120a, second guide boss 120b, and third guide boss 120c do not move laterally relative the drive carriage 104 and guide base 106. Accordingly, in Step 1, the transfer tube 152, malecot holding tube cover 158, and malecot holding tube 160 are not moved laterally.

Figure 17:
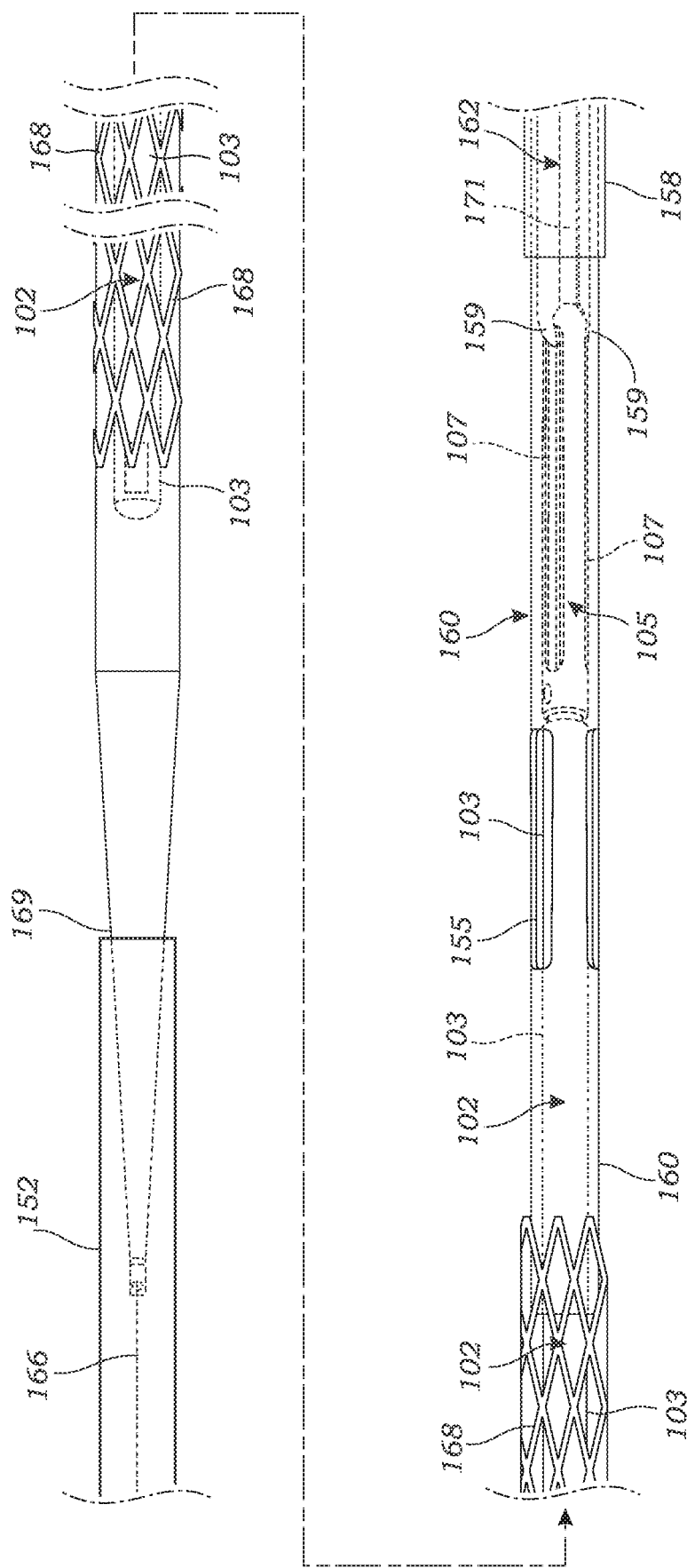

As the drive carriage 104 is moved upward in Step 1 from the bottom end of the guide base 106, the fourth guide boss 120d follows the guide slot 110d thereby moving the fourth guide boss 120d to the right (distally). The claw-shaft 162 is retained by the fourth guide boss 120d and therefore, the claw-shaft 162 is moved to the right by 6 mm. The claw-shaft 162 is attached to the shunt assembly 104, and therefore, the shunt assembly 102 is also moved to the right in Step 1 by 6 mm. The movement of the shunt assembly 102 to the right during Step 1 causes the malecot 105 to be moved into the malecot holding tube 160 which moves the malecot 105 from the slots 155 of the malecot holding tube 160 to the unslotted tubular portion of the malecot holding tube 160 thereby compressing the malecot 105 to its radially compressed state within the malecot holding tube 160, as shown in FIG. 17.

Figure 2:
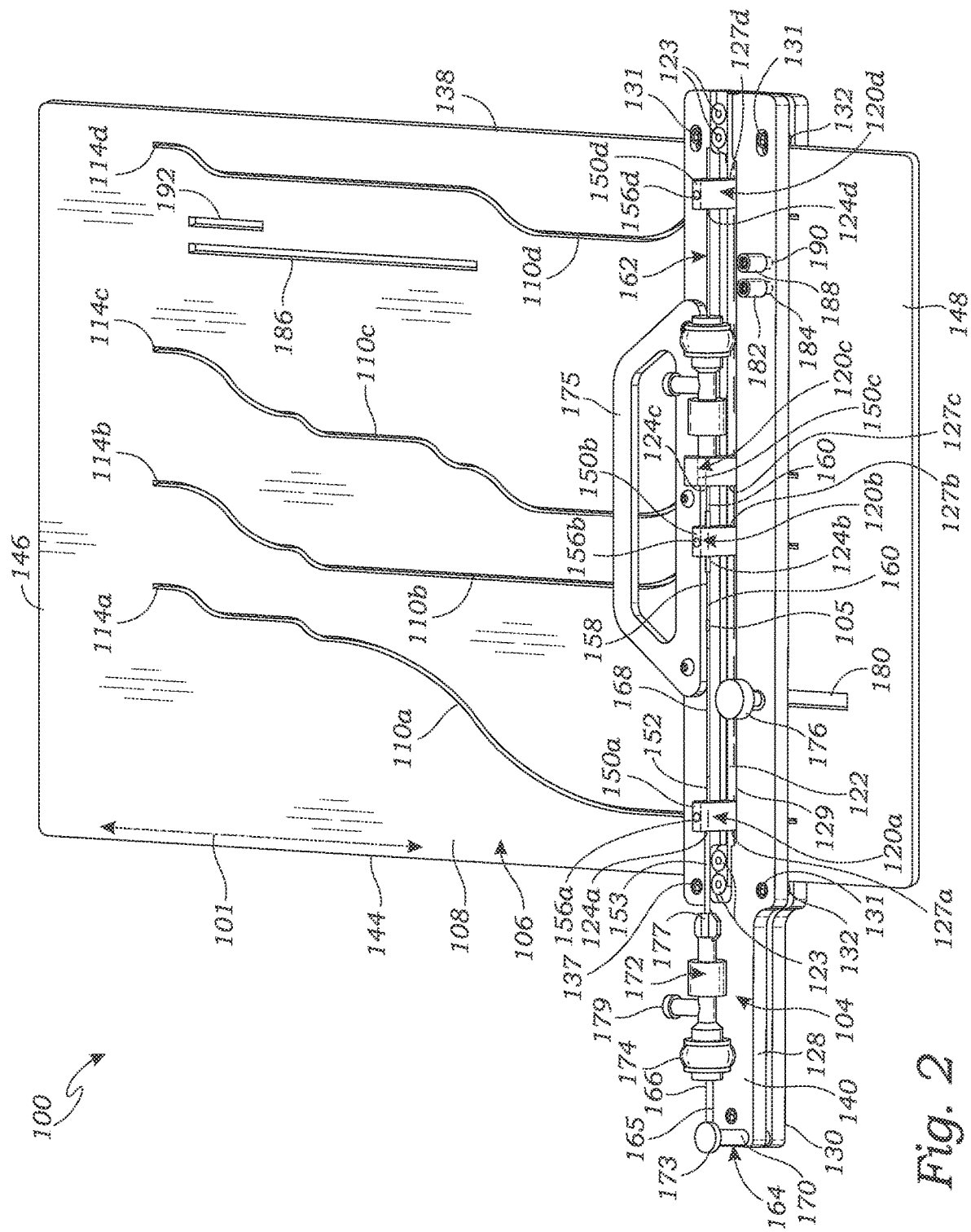
FIG. 2 is a front perspective view of a shunt loader and shunt assembly of FIG. 1 illustrating Step 1 of a method of using the shunt loader, according to one embodiment of the disclosed inventions.

As shown in FIG. 2, at the end of Step 1, the flush stop 176 hits the top end of the flush stop slot 180 which prevents further upward movement of the drive carriage 104. This is the flushing position of the drive carriage 104 (i.e., the end of Step 1 movement of the drive carriage 104). At this point, the shunt assembly 102 and transfer tube 152 are flushed to remove air from the shunt assembly 102 and transfer tube 152. A flushing fluid source is connected to the first flush port 179 of the of the first flushing adapter 172, and to the second flush port 206 of the second flushing adapter 200. The flushing fluid source connected to each of the first flushing adapter 172 and the second flushing adapter 200 may be the same fluid source or different fluid sources. The fluid source may be a source of pressurized saline, heparinized saline, or other suitable fluid. The flushing fluid is pressurized with flushing fluid to flush air from the first fittings 174, 204 (e.g., compression fittings) of the first flushing adapter 172 and second flushing adapter 200, respectively. The first fittings 174, 204 are then tightened to create a seal to the components running through them. The second flushing adapter 200 is pressurized with flushing fluid to flush air from shunt assembly 102 and transfer tube 152. Once the shunt assembly 102 and transfer tube 152 are sufficiently flushed to remove air, the flushing fluid is turned off. The first fittings 174, 204 are then loosened to allow for free lateral motion of the components running through them.

After the flushing step is completed, the plunger 178 of the flush stop 176 is pulled upward out of the flush stop slot 180 to allow the drive carriage 104 to be moved longitudinally upward past the flush stop slot 180. The plunger 178 can be locked in its retracted position by rotating it to a locked position (e.g., rotating it 90° for a quarter turn lock).

Figure 3:
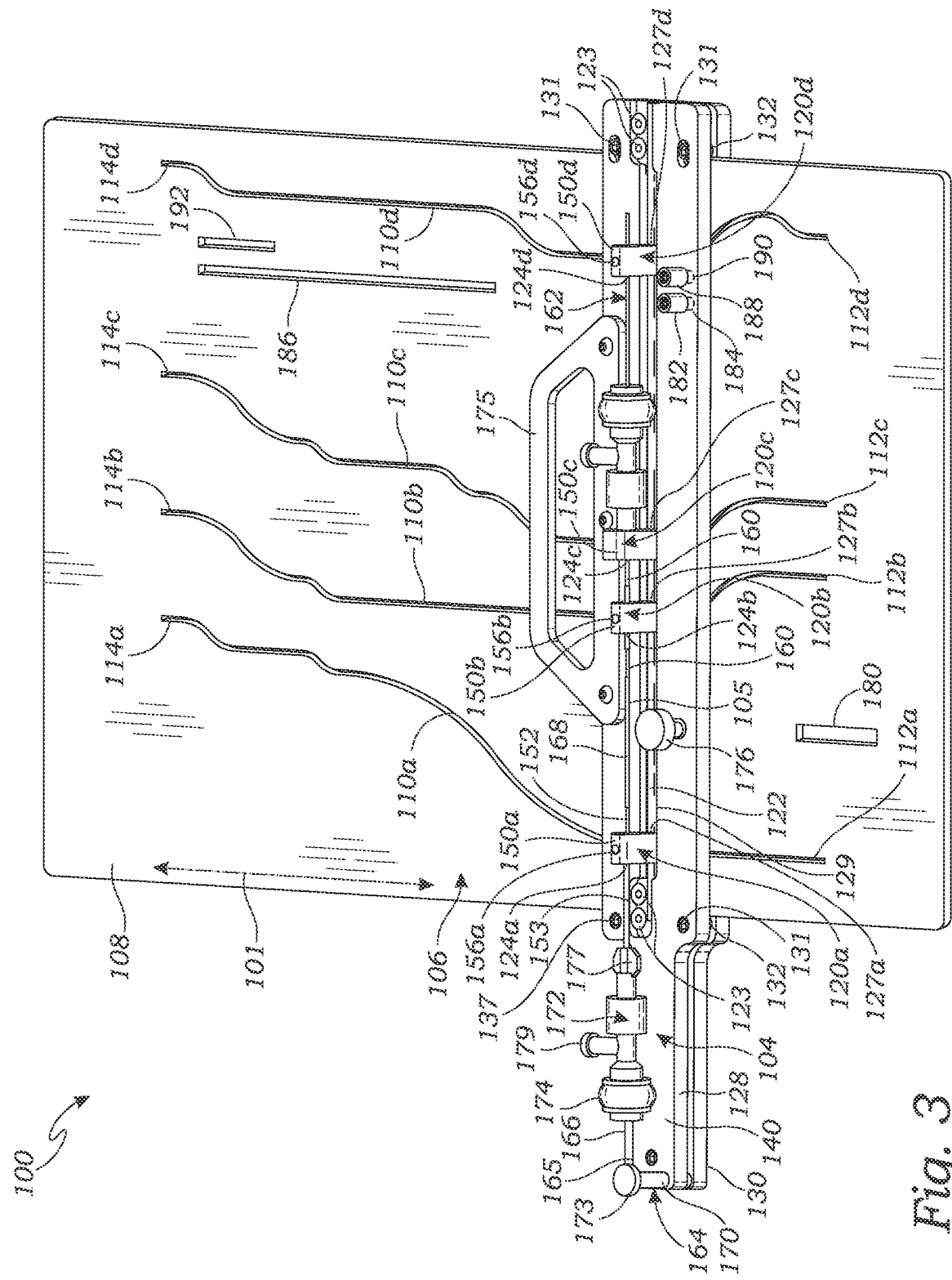
FIG. 3 is a front perspective view of a shunt loader and shunt assembly of FIG. 1 illustrating Step 2 of a method of using the shunt loader, according to one embodiment of the disclosed inventions.

Turning to FIG. 3, in Step 2, the drive carriage 104 is further advanced longitudinally upward relative to the guide base 106 from its ending position in Step 1. As shown in FIG. 26, in Step 2, the second guide slot 110b, third guide slot 110c, and fourth guide slot 110d curve to the left, and the first guide slot 110a continues to extend straight. As shown in the table of FIG. 27, the Step 2 portion of guide slots 110b, 110c and 110c curve laterally to the left by 16 mm, and the Step 2 portion of the first guide slot 110a has zero laterally movement.

Figure 18:
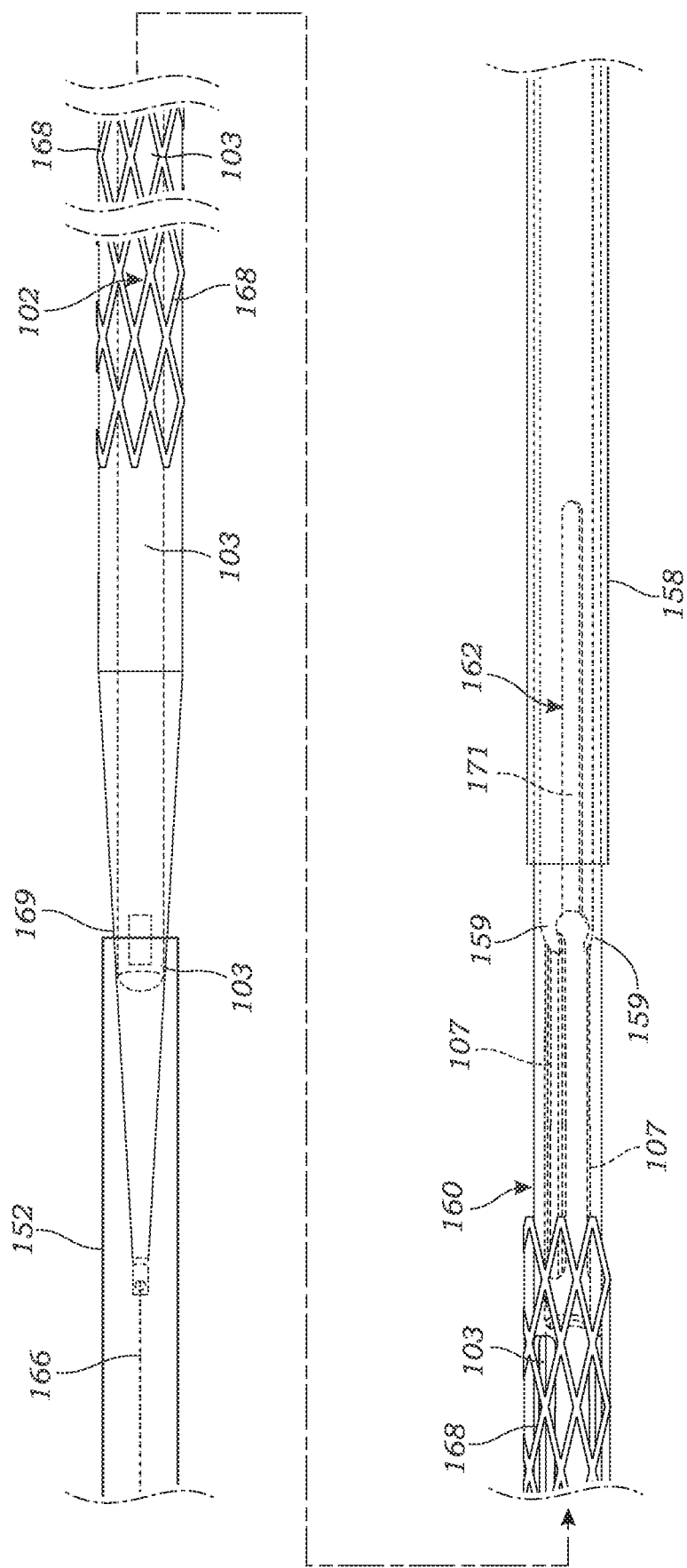

As the drive carriage 104 is moved upward in Step 2, the second guide boss 120b follows the guide slot 110b thereby moving the second guide boss 120b to the left (proximally), the third guide boss 120c follows the guide slot 110c thereby moving the third guide boss 120c to the left, and the fourth guide boss follows the fourth guide boss 120d thereby moving the fourth guide boss 120d to the left. The second guide boss 120b retains the malecot holding tube cover 152, and therefore the malecot holding tube cover 158 is moved to the left by 16 mm during Step 2. The third guide boss 120c retains the malecot holding tube 160, and therefore the malecot holding tube 160 is moved to the left by 16 mm during Step 2. During Step 2, the fourth guide boss 120d moves the claw-shaft 162 and shunt assembly 102 to the left by 16 mm. The shroud 168 does not move laterally during the entire method because it is held in place by the shroud tether 166 being attached to the shroud tether retainer 164 which does not move laterally as the drive carriage 104 is advanced upward. The movement of the shunt assembly 102 to the left during Step 2 pushes the proximal end of the shunt body 103 into the tapered section 169 of the shroud 168 such that the proximal end of the shunt body 103 is within the tapered section 169, as depicted in FIG. 18. As shown in FIG. 18, the malecot holding tube 160 also moves laterally to the left synchronously with the shunt assembly 102 so that the malecot 105 remains compressed in the non-slotted portion of the malecot holding tube 160.

Figure 4:
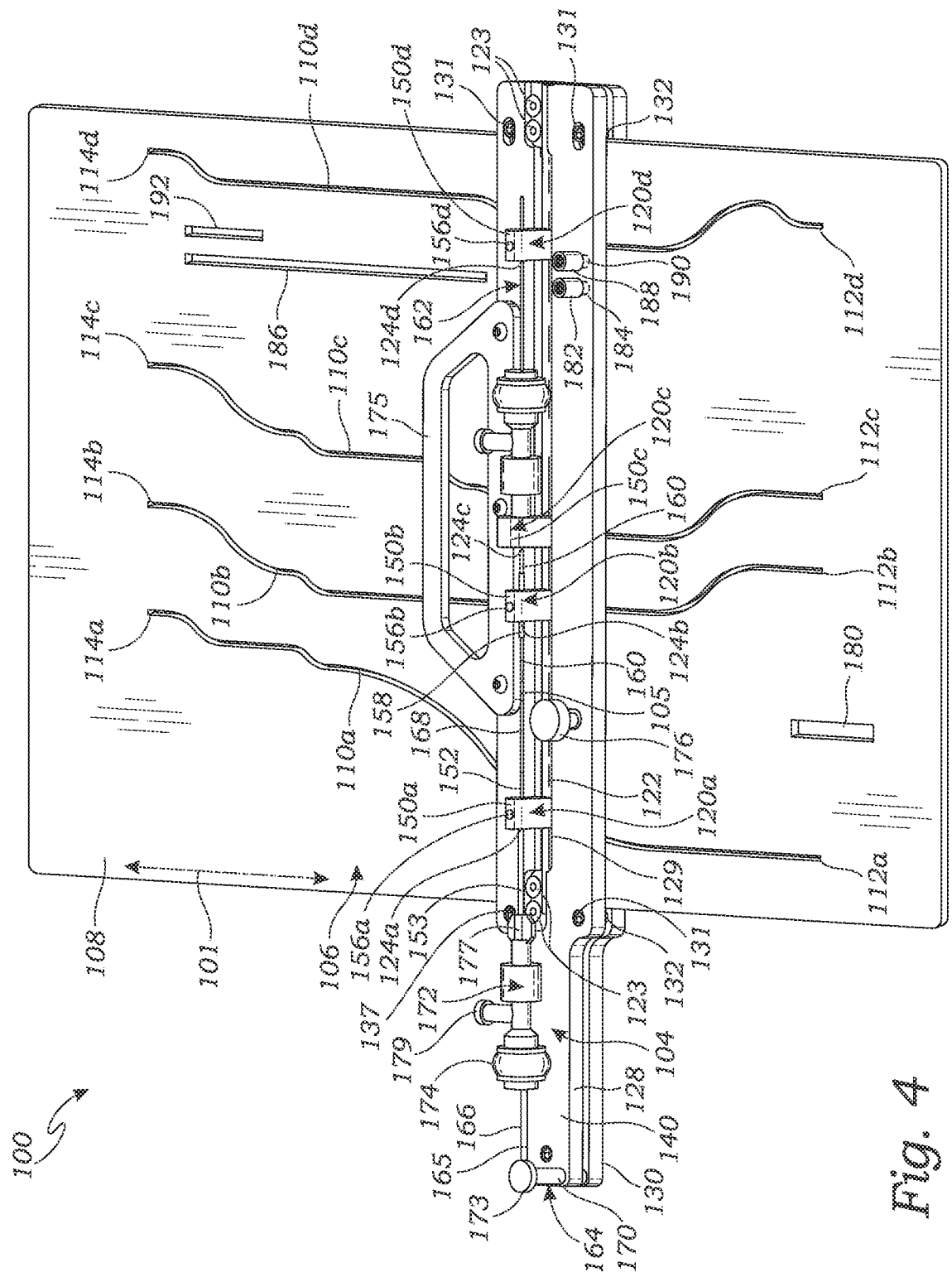
FIG. 4 is a front perspective view of a shunt loader and shunt assembly of FIG. 1 illustrating Step 3 of a method of using the shunt loader, according to one embodiment of the disclosed inventions.

Referring to FIG. 4, in Step 3, the drive carriage 104 is further advanced longitudinally upward relative to the guide base 106 from its ending position in Step 2. As shown in FIG. 26, in Step 3, the first guide slot 110a curves to the right, and the second guide slot 110b, third guide slot 110c, and fourth guide slot 110d extend straight. As shown in the table of FIG. 27, the Step 2 portion of the first guide slot 110a curves laterally to the right by 15 mm and, and the Step 2 portion of the first guide slot 110a, second guide slot 110b and third guide slot 110c have zero laterally movement.

Figure 19:
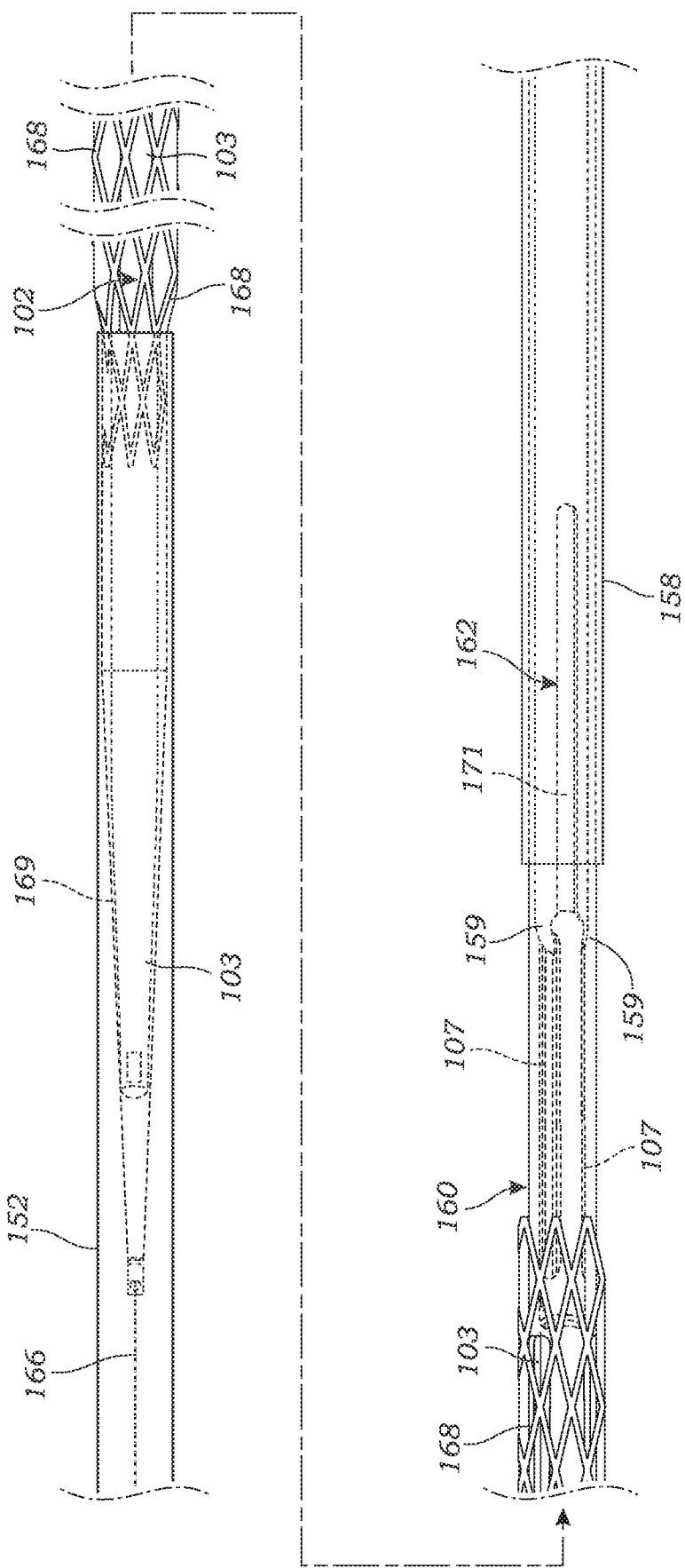

As the drive carriage 104 is moved upward in Step 3, the first guide boss 120a follows the guide slot 110b thereby moving the first guide boss 120a to the right. The first guide boss 120a retains the transfer tube 152, and therefore the transfer tube 152 is moved to the right by 15 mm in Step 3. The movement of the transfer tube 152 to the right during Step 3 moves the transfer tube 152 over the shunt body 103 and shroud 168 thereby sheathing part of the shunt body 103 and shroud 168 within the transfer tube 152, as depicted in FIG. 19. The outer diameter of the shroud 168 and shunt body 103 within the shroud 168 is slightly larger than the inner diameter of the transfer tube 152 such that as the transfer tube 152 is moved over the shroud 168 and shunt body 103, the shroud 168 and shunt body 103 collapse into the transfer tube 152. As the shroud 168 and shunt body 103 are compressed/collapsed into the transfer tube 152, the tapered section 169 of the shroud 168 is compressed onto the proximal end of the shunt body 103. As shown in FIG. 11, the shunt body 103 has a rigid, radio-opaque marker 196 in its proximal end such that when the tapered section 169 of shroud 168 is compressed onto the proximal end of the shunt body 103, the proximal end of the shunt body 103 is held tightly in place by the shroud 168.

Figure 5:
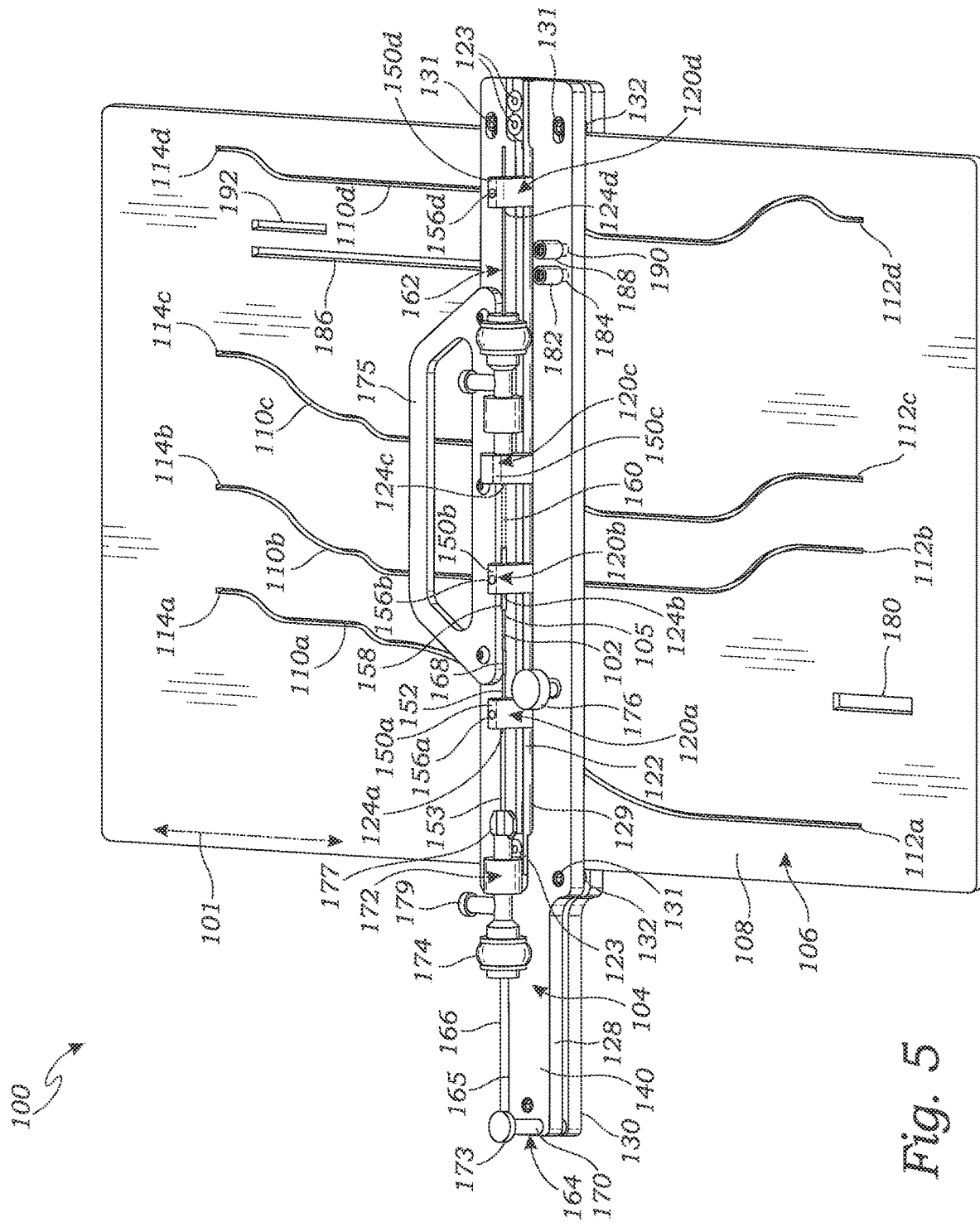
FIG. 5 is a front perspective view of a shunt loader and shunt assembly of FIG. 1 illustrating Step 4 of a method of using the shunt loader, according to one embodiment of the disclosed inventions.

Referring to FIG. 5, in Step 4, the drive carriage 104 is further advanced longitudinally upward relative to the guide base 106 from its ending position in Step 4. As shown in FIG. 26, in Step 4, the first guide slot 110a continues to curve to the right, the second guide slot 110b extends straight, the third guide slot 110c curves to the right, and the fourth guide slot 110d curves to the right. As shown in the table of FIG. 27, the Step 4 portion of the first guide slot 110a curves laterally to the right by 12.5 mm, the Step 4 portion of the second guide slot 110b has zero lateral movement, the third guide slot 110c curves laterally to the right by 12.5 mm and the fourth guide slot 110d curves laterally to the right by 12.5 mm.

Figure 20:
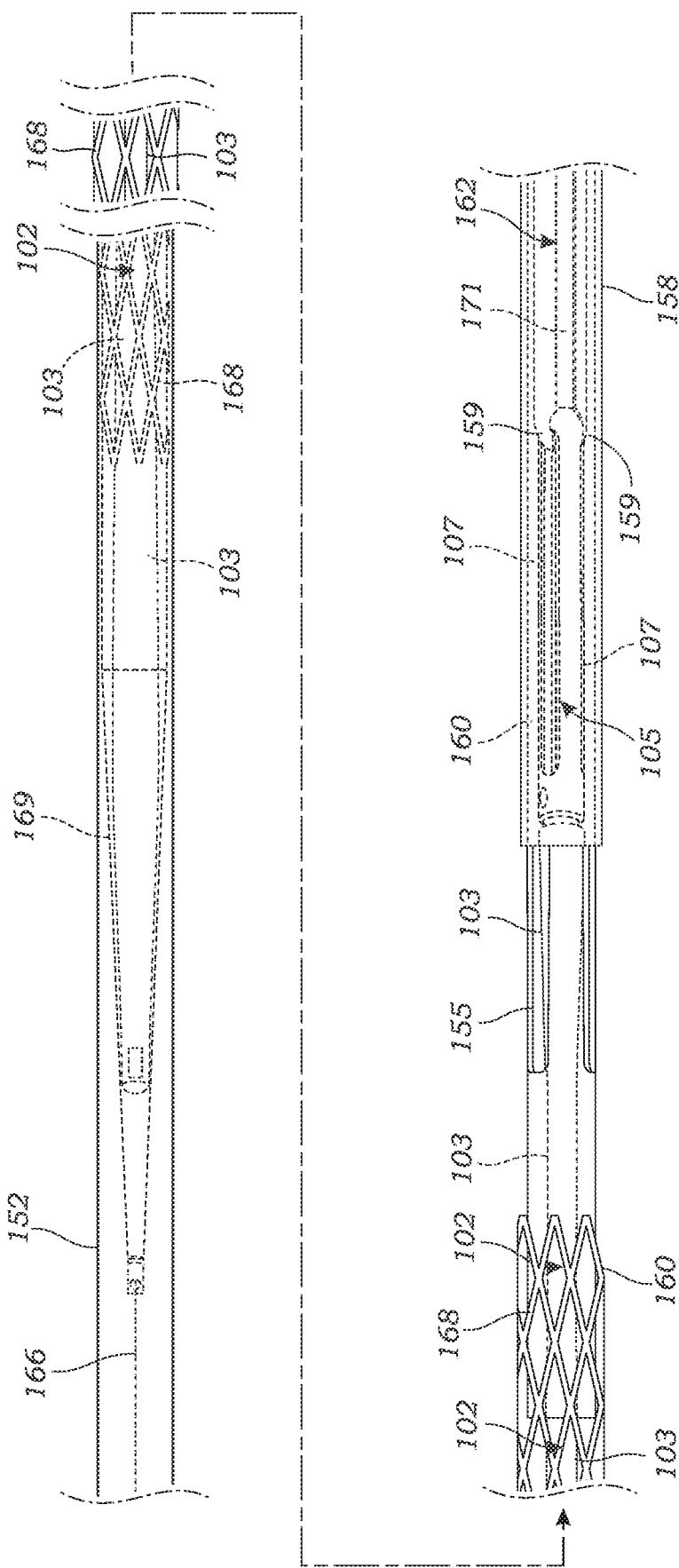

As the drive carriage 104 is moved upward in Step 4, the first guide boss 120a and attached transfer tube 152, the third guide boss 120c and attached malecot holding tube 160, and the fourth guide boss 120d and attached claw assembly 162, all move laterally to the right by 12.5 mm. In Step 4, the malecot holding tube cover 158 and shroud 168 do not move laterally. The movement of the claw assembly 162 to the right pulls the attached malecot 105 and distal end of the shunt body 103 (the claw 161 is still attached to the malecot 105) to the right thereby stretching the shunt body 103 (the proximal end of the shunt body 103 is held fixed in the same lateral position by the shroud 168), as shown in FIG. 20. As depicted in FIG. 20, the stretching of the shunt body 103 causes the diameter of the shunt body 103 to decrease by an effect known as "necking." The movement of the claw assembly 162 to the right also moves the malecot 105 into the malecot holding tube cover 158, as shown in FIG. 19. The movement of the transfer tube 152 to the right continues to sheath the shroud 168 and shunt body 103 within the transfer tube 152, as depicted in FIG. 19.

Also, at the end of Step 4, the first anti-reversal stop 182 reaches the first end of the first anti-reversal slot 186 and the plunger 184 moves downward into the first anti-reversal slot 186. At this point, the first anti-reversal stop 182 prevents the drive carriage 104 from being moved downward (backward), but still allows the drive carriage 104 to continue to move upward (forward) with the plunger 184 moving forward in the first anti-reversal slot 186.

Figure 6:
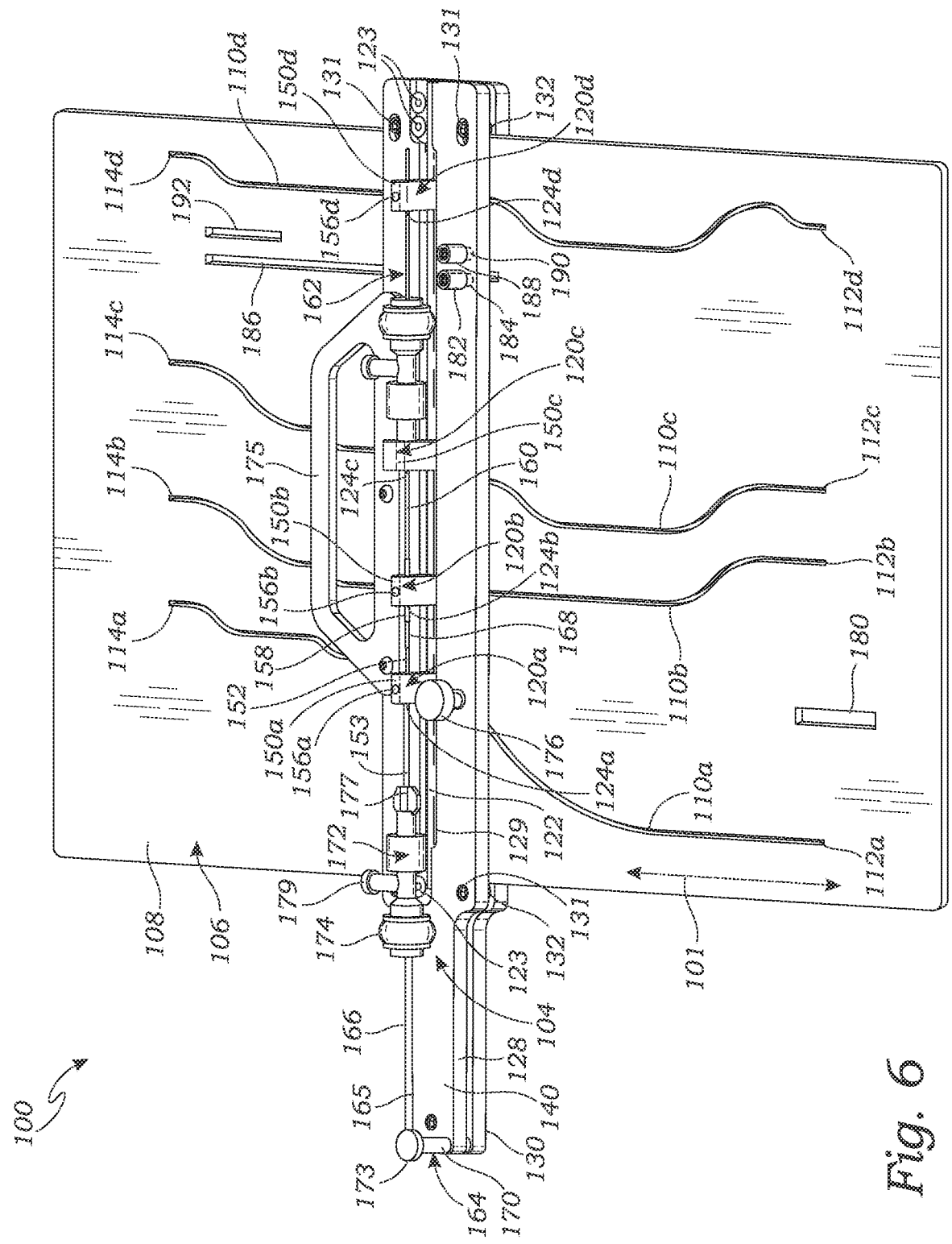
FIG. 6 is a front perspective view of a shunt loader and shunt assembly of FIG. 1 illustrating Step 5 of a method of using the shunt loader, according to one embodiment of the disclosed inventions.

Referring to FIG. 6, in Step 5, the drive carriage 104 is further advanced longitudinally upward relative to the guide base 106 from its ending position in Step 5. As shown in FIG. 26, in Step 5, the first guide slot 110a continues to curve to the right, the second guide slot 110b extends straight, the third guide slot 110c curves to the right, and the fourth guide slot 110d extends straight. As shown in the table of FIG. 27, the Step 5 portion of the first guide slot 110a curves laterally to the right by 7.5 mm, the Step 5 portion of the second guide slot 110b has zero lateral movement, the Step 5 portion of the third guide slot 110c curves laterally to the right by 7.5 mm and the fourth guide slot 110d has zero lateral movement.

Figure 21:
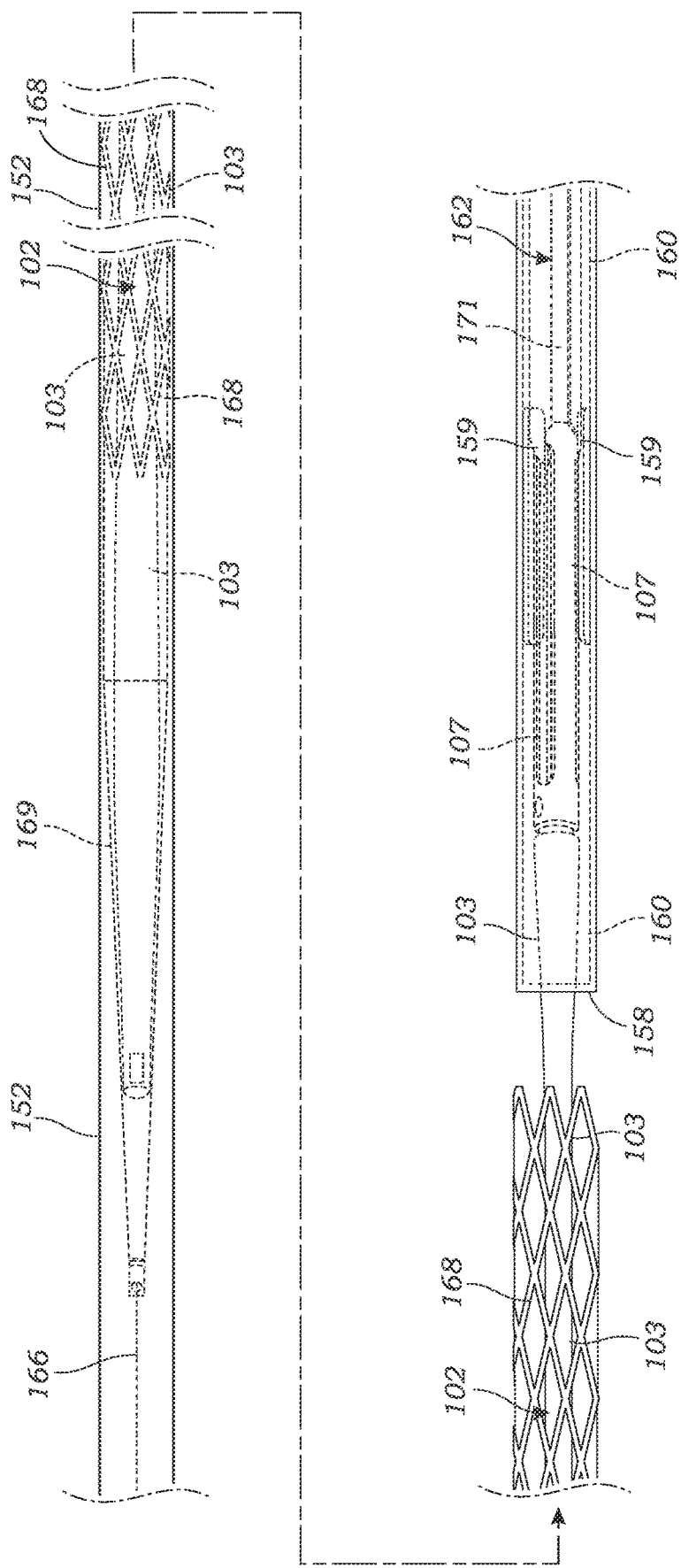

As the drive carriage 104 is moved upward in Step 5, the first guide boss 120a and attached transfer tube 152 move laterally to the right by 7.5 mm, which continues to sheath the shroud 168 and shunt body 103 within the transfer tube 152, as depicted in FIG. 21. The third guide boss 120c and attached malecot holding tube 160 move laterally to the right by 7.5 mm, which moves the malecot holding tube 160 to the right relative to the malecot holding tube cover 158 (which does not move laterally) and the shroud 168 (which does not move laterally). The movement of the malecot holding tube 160 to the right moves the slots 155 on the malecot holding tube 160 into the malecot holding tube cover 158. Step 5 also removes the malecot holding tube 160 from the shroud 168, which allows the distal end of shroud 168 which was previously disposed over the proximal end of the malecot holding tube 160 to be sheathed within the transfer tube 152, as shown in FIG. 21. In other words, while the distal end of the shroud 168 is disposed over the malecot holding tube 160, the distal end of the shroud 168 will not fit within the transfer tube 162.

Figure 7:
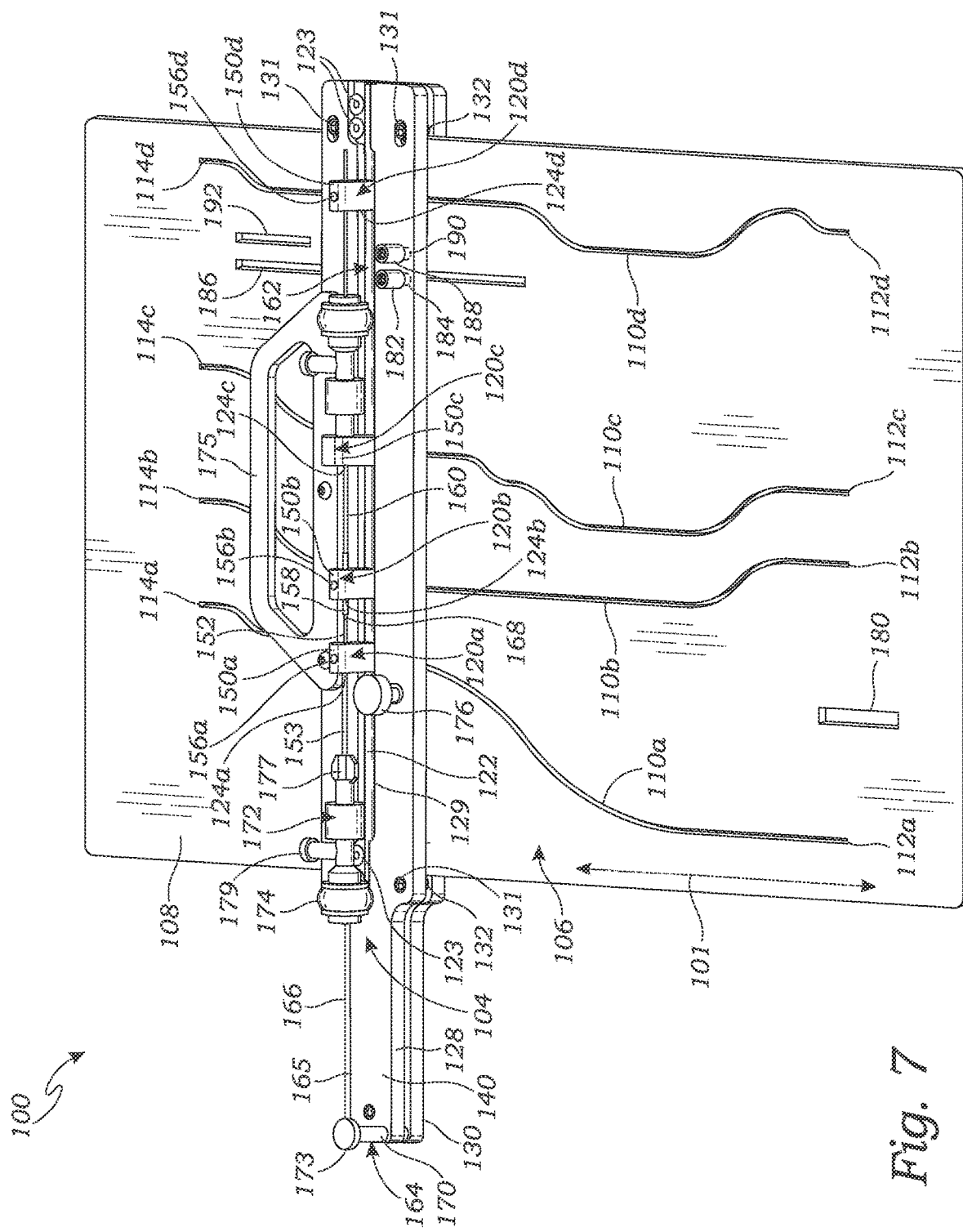
FIG. 7 is a front perspective view of a shunt loader and shunt assembly of FIG. 1 illustrating Step 6 of a method of using the shunt loader, according to one embodiment of the disclosed inventions.

Referring to FIG. 7, in Step 6, the drive carriage 104 is further advanced longitudinally upward relative to the guide base 106 from its ending position in Step 5. As shown in FIG. 26, in Step 6, the first guide slot 110a continues to curve to the right, and the second guide slot 110b, third guide slot 110c and fourth guide slot 110d each extends straight. As shown in the table of FIG. 27, the Step 6 portion of the first guide slot 110a curves laterally to the right by 14 mm, and the Step 6 portion of the second guide slot 110b, third guide slot 110c and fourth guide slot 110d each has zero lateral movement.

Figure 22:
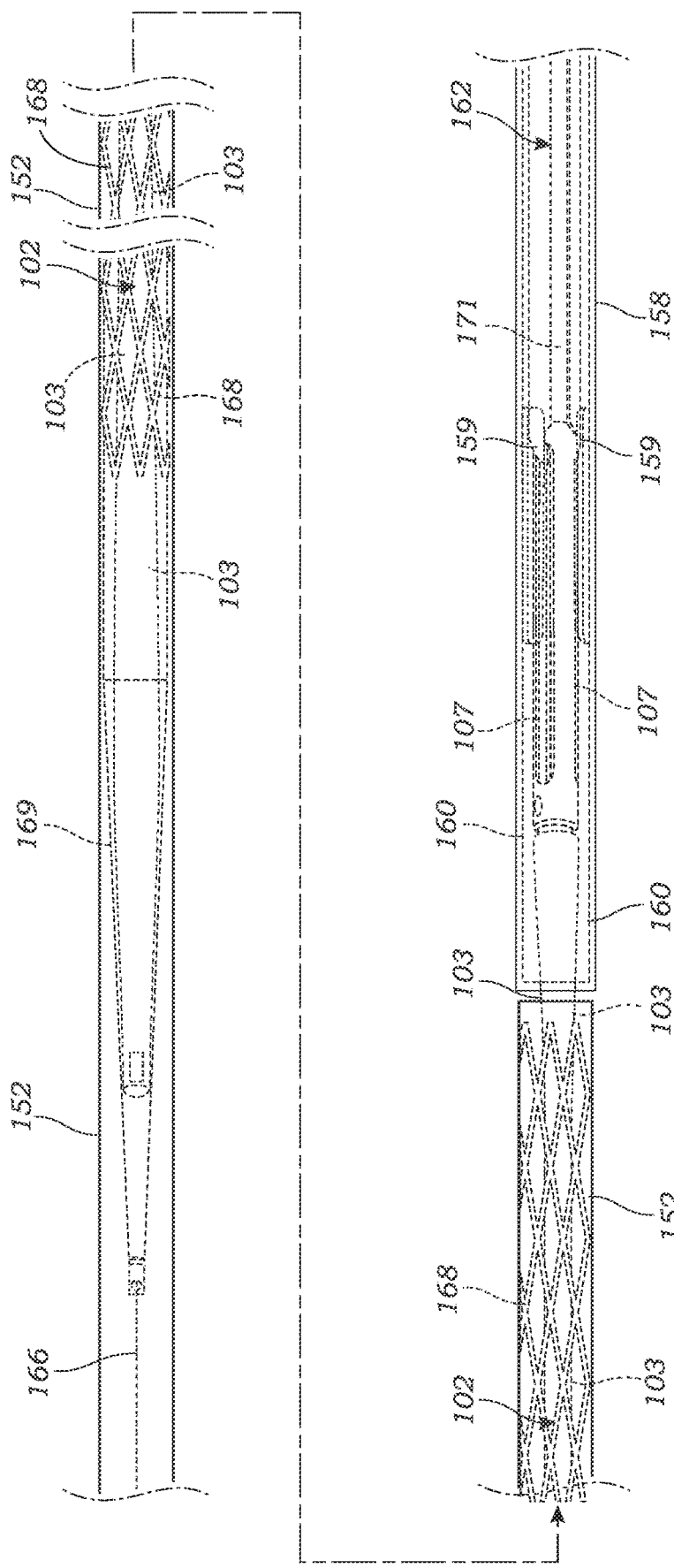

As the drive carriage 104 is moved upward in Step 6, the first guide boss 120a and attached transfer tube 152 move laterally to the right by 14 mm, which continues to sheath the shroud 168 and shunt body 103 within the transfer tube 152 until the distal end of the transfer tube 152 is proximate the proximal end of the malecot holding tube 160, as depicted in FIG. 22. In Step 6, the shroud 168, shunt assembly 102, malecot holding tube cover 158, malecot holding tube 160 and claw assembly 162 do not move laterally.

Figure 8:
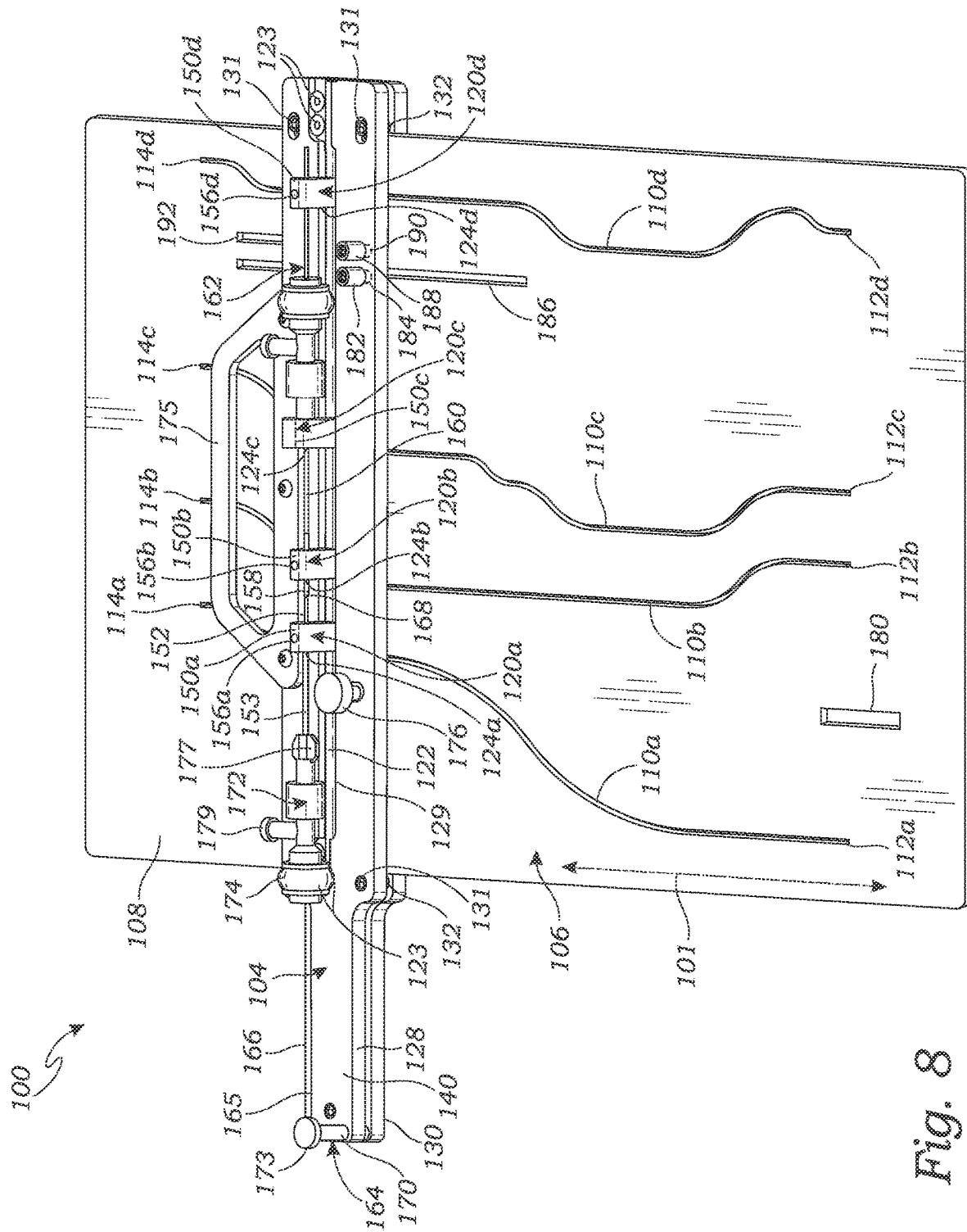
FIG. 8 is a front perspective view of a shunt loader and shunt assembly of FIG. 1 illustrating Step 7 of a method of using the shunt loader, according to one embodiment of the disclosed inventions.

Referring to FIG. 8, in Step 7, the drive carriage 104 is further advanced longitudinally upward relative to the guide base 106 from its ending position in Step 6. As shown in FIG. 26, in Step 7, the first guide slot 110a continues to curve to the right, the second guide slot 110b curves to the right, the third guide slot 110c curves to the right, and the fourth guide slot 110d extends straight. As shown in the table of FIG. 27, the Step 7 portion of the first guide slot 110a curves laterally to the right by 5.5 mm, the Step 7 portion of the second guide slot 110b curves laterally to the right by 5.5 mm, the Step 7 portion of the third guide slot 110c curves laterally to the right by 5.5 mm, and the Step 7 portion of the fourth guide slot 110d has zero lateral movement.

Figure 23:
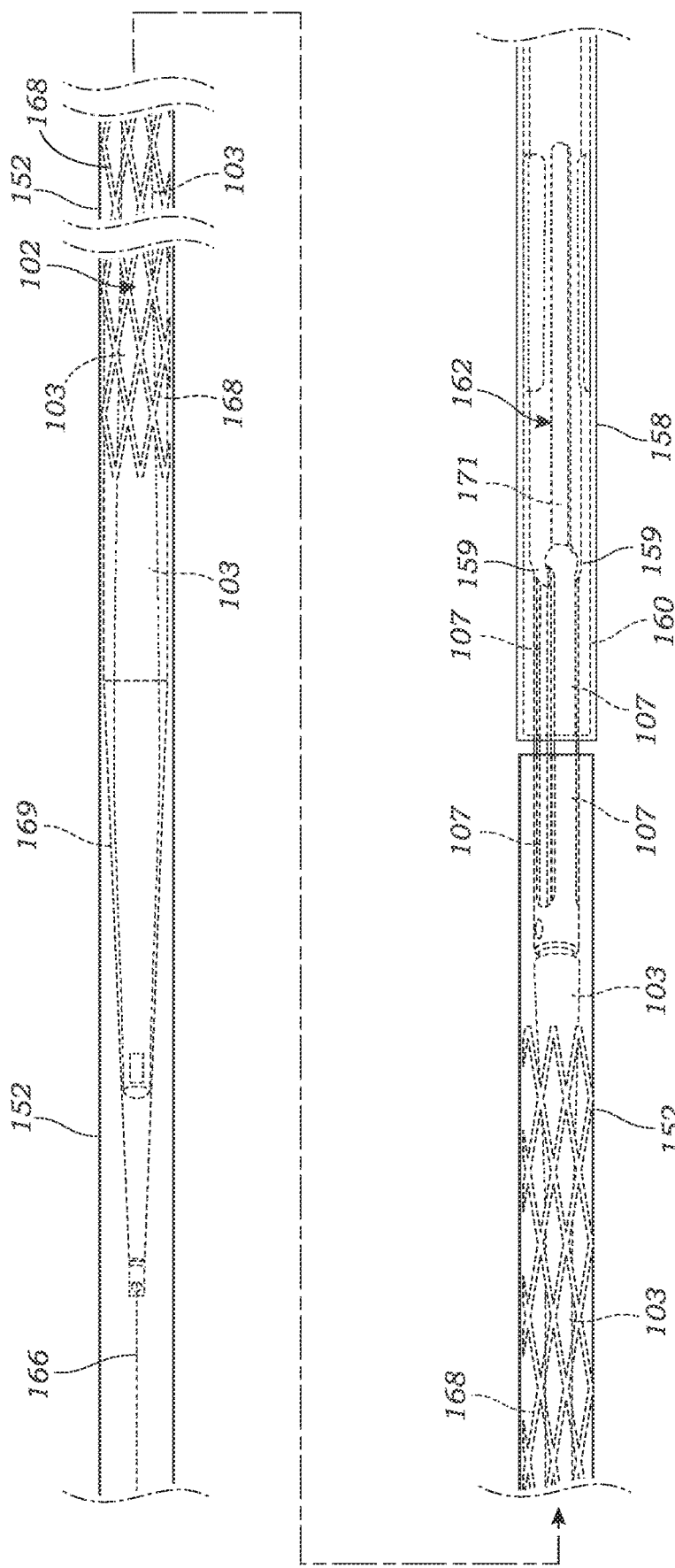

As the drive carriage 104 is moved upward in Step 7, the first guide boss 120a and attached transfer tube 152, the second guide boss 120b and attached malecot holding tube cover 158, and third guide boss 120c and attached malecot holding tube 160 synchronously move laterally to the right by 5.5 mm. This movement continues to move the transfer tube 152 over the shroud 168 and shunt body 103 (i.e., sheathing the shroud 168 and shunt body 103 within the transfer tube 152) while the malecot holding tube cover 158 and malecot holding tube 160 move to the right out of the way of the transfer tube 152, as shown in FIG. 23. The fourth guide boss 120d which holds the claw assembly 162 does not move laterally. As the malecot holding tube 160 moves over the malecot 105, the proximal end of the shaft 171 presses against the distal end of the malecot 105 and prevents the friction between the malecot fingers 107 and the malecot holding tube 160 from moving the malecot 105 distally. As shown in FIG. 23, during Step 7, the malecot holding tube cover 158 and malecot holding tube 160 are moving to the right relative to the malecot 105 such that the malecot 105 begins to exit the respective proximal ends of the malecot holding tube cover 158 and malecot holding tube 160 and the transfer tube 152 captures part of the malecot 105. The distal end of the transfer tube 152 is close enough to the proximal end of the malecot holding tube cover 158 such that the malecot 105 does not expand as it exits the malecot holding tube cover 158 and enters the transfer tube 152. In addition, the malecot holding tube cover 158 keeps the malecot 105 in the compressed state as the slots 155 on the malecot holding tube 160 are moved to the right past the malecot 105 during Step 7. When the malecot 105 enters the transfer tube 152, the transfer tube 152 keeps the malecot 105 in the compressed state.

Figure 9:
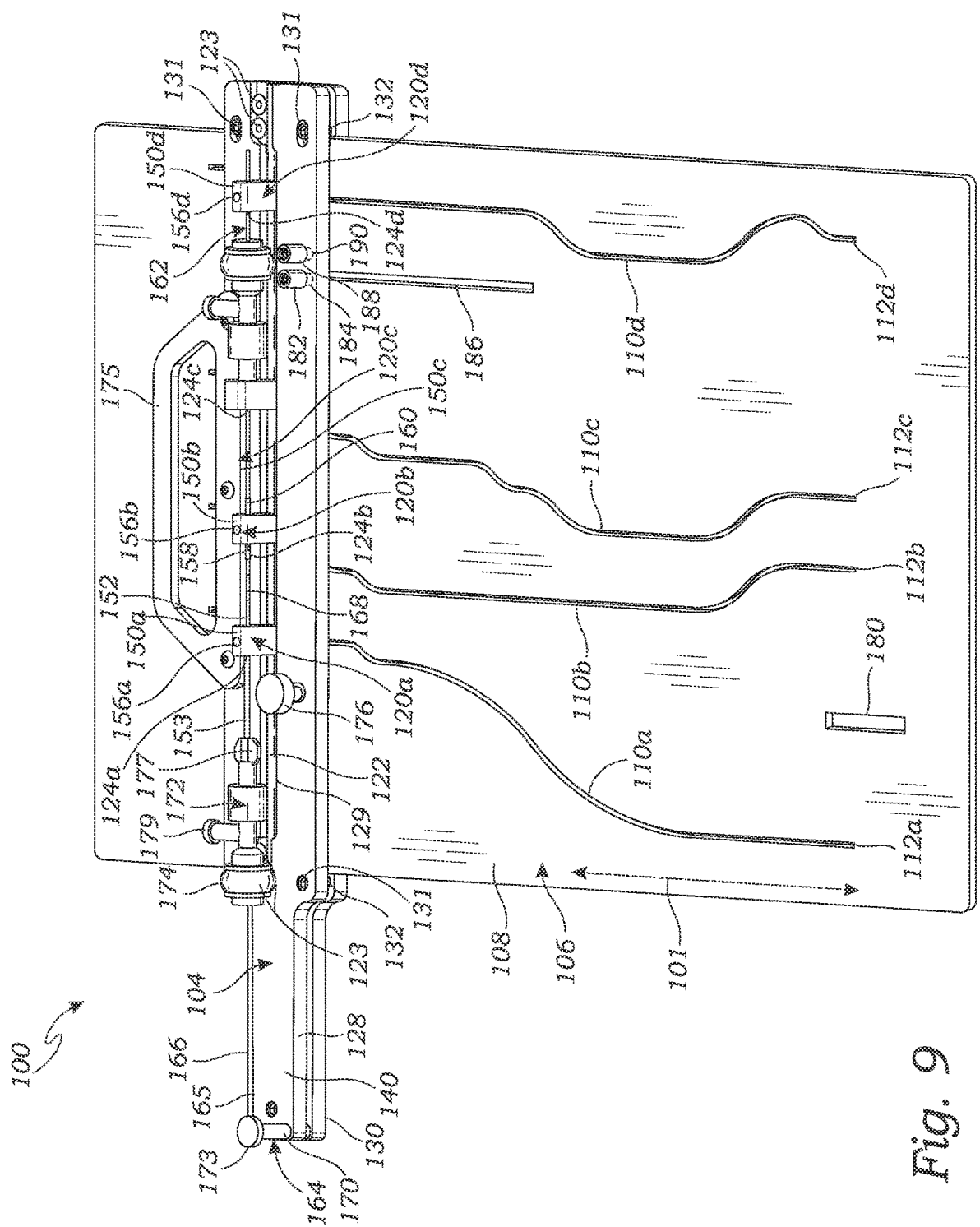
FIG. 9 is a front perspective view of a shunt loader and shunt assembly of FIG. 1 illustrating Step 8 of a method of using the shunt loader, according to one embodiment of the disclosed inventions.

Referring to FIG. 9, in Step 8, the drive carriage 104 is further advanced longitudinally upward relative to the guide base 106 from its ending position in Step 7. As shown in FIG. 26, in Step 8, the first guide slot 110a extends straight, the second guide slot 110b curves to the right, the third guide slot 110c curves to the right, and the fourth guide slot 110d continues to extend straight. As shown in the table of FIG. 27, the Step 8 portion of the first guide slot 110a has zero lateral movement, the Step 8 portion of the second guide slot 110b curves laterally to the right by 10 mm, the Step 8 portion of the third guide slot 110c curves laterally to the right by 10 mm, and the Step 8 portion of the fourth guide slot 110d has zero lateral movement.

Figure 24:
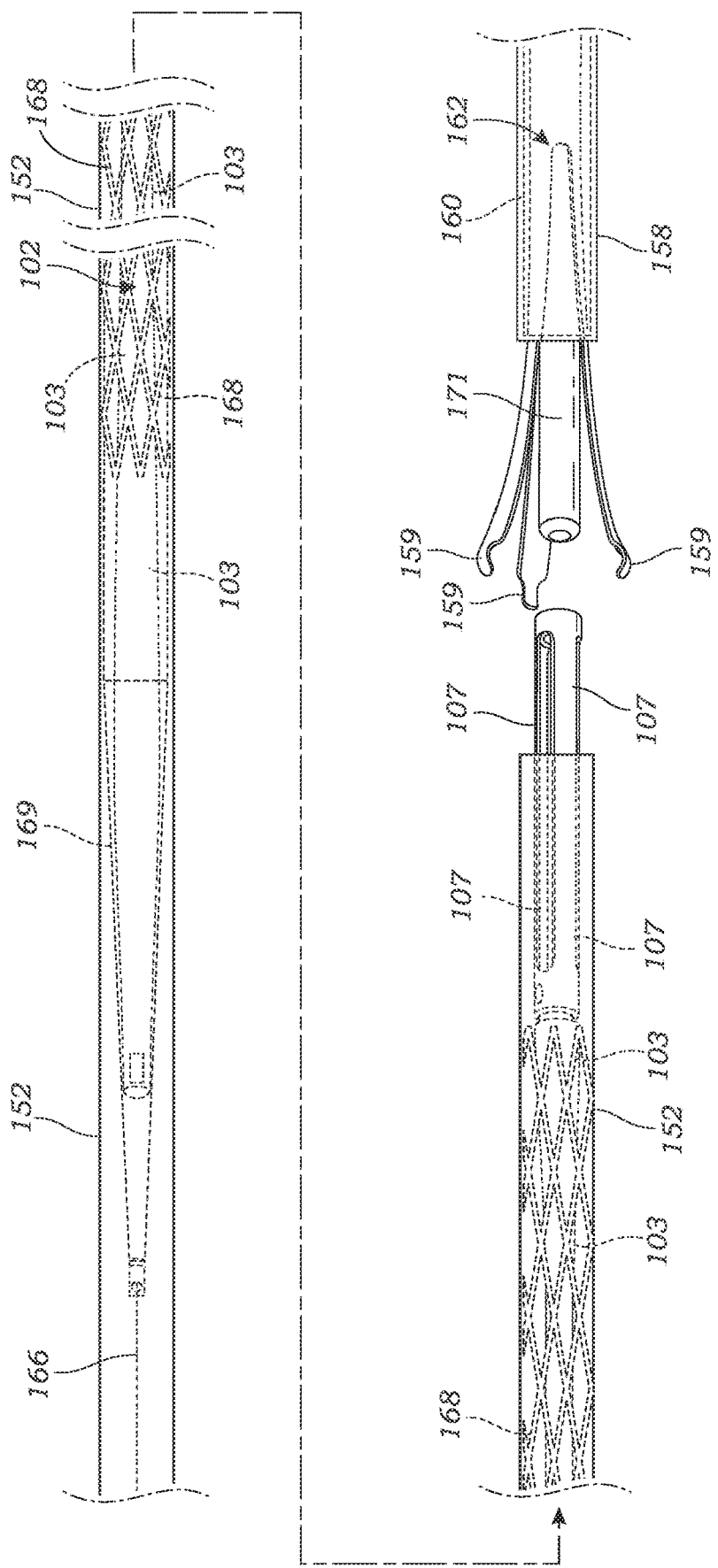

As the drive carriage 104 is moved upward in Step 8, the second guide boss 120b and attached malecot holding tube cover 158, and the third guide boss 120c and attached malecot holding tube 160 each move laterally to the right by 10 mm while the first guide boss 120a and attached transfer tube 152 and fourth guide boss 120d and attached claw-shaft 162 do not move laterally. Thus, in Step 8, the malecot holding tube cover 158 and malecot holding tube 160 are moved to the right which removes the claw 161 from within the malecot holding tube cover 158 and malecot holding tube 160, as depicted in FIG. 24. As a result, the claw 161 expands and releases the malecot 105. Once released, the malecot 105 will be pulled into the transfer tube 152 by the stretched shunt body 103. The malecot 105 will move until the proximal edge of the malecot 105 is resting against the distal end of the shroud. At this point, and as at the end of Step 7, the distal end of the malecot 105 is still extending out from the distal end of the transfer tube 152, as shown in FIG. 24.

Partway through Step 8, the second anti-reversal stop 188 reaches the first end of the second anti-reversal slot 192 and the plunger 190 moves downward into the second anti-reversal slot 192. At this position of the drive carriage 104, the second anti-reversal stop 182 prevents the drive carriage 104 from being moved downward (backward), but still allows the drive carriage 104 to continue to move upward (forward) with the plunger 190 moving forward in the second anti-reversal slot 192.

Figure 10:
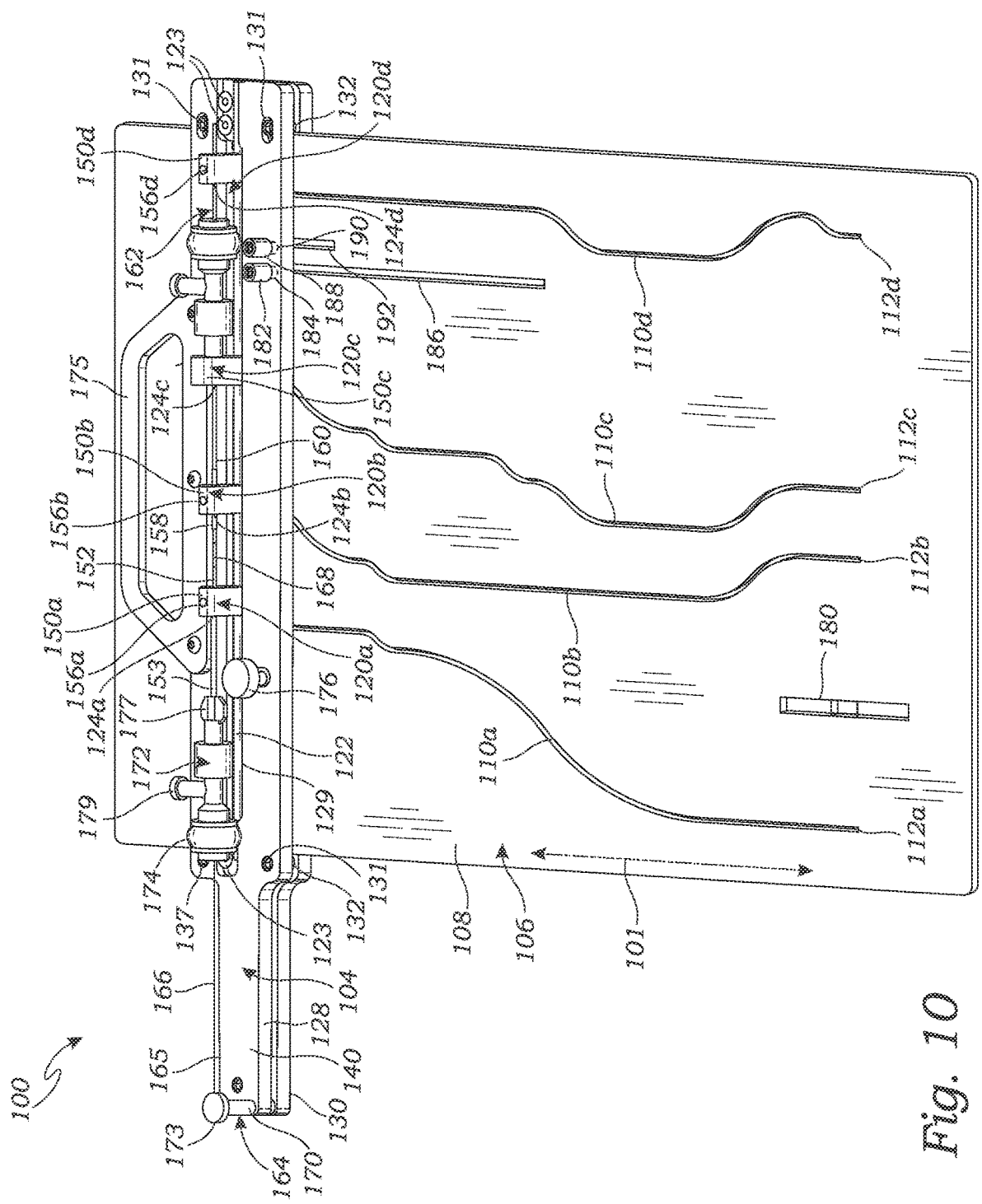
FIG. 10 is a front perspective view of a shunt loader and shunt assembly of FIG. 1 illustrating Step 9 of a method of using the shunt loader, according to one embodiment of the disclosed inventions.

Referring to FIG. 10, in Step 9, the drive carriage 104 is further advanced longitudinally upward relative to the guide base 106 from its ending position in Step 8. As shown in FIG. 26, in Step 9, the first guide slot 110a curves to the right, the second guide slot 110b curves to the right, the third guide slot 110c curves to the right, and the fourth guide slot 110d curves to the right. As shown in the table of FIG. 27, the Step 9 portion of the first guide slot 110a curves laterally to the right by 8 mm, the Step 9 portion of the second guide slot 110b curves laterally to the right by 8 mm, the Step 9 portion of the third guide slot 110c curves laterally to the right by 8 mm, and the Step 9 portion of the fourth guide slot 110d curves to the right by 8 mm.

Figure 25:
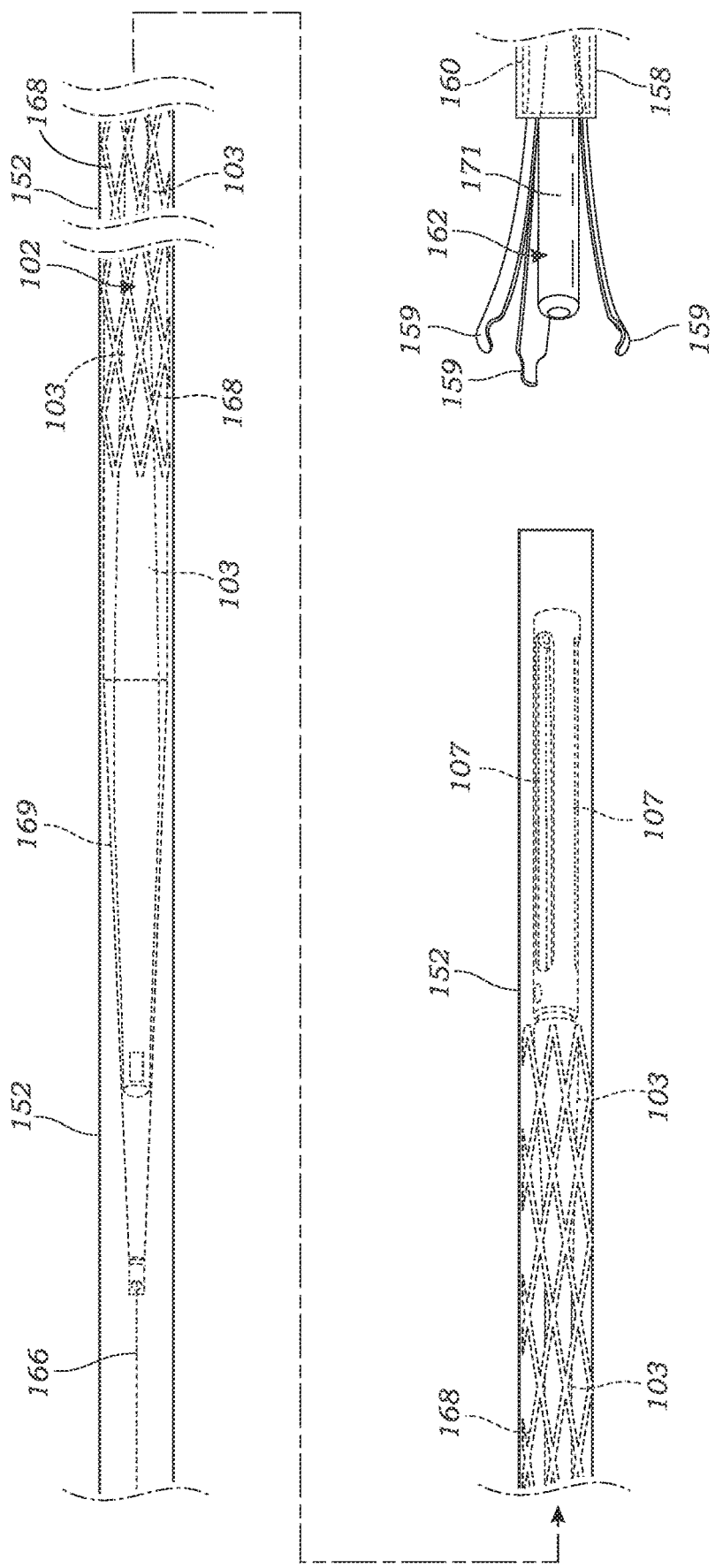

As the drive carriage 104 is moved upward in Step 9, the first guide boss 120a and attached transfer tube 152, the second guide boss 120b and attached malecot holding tube cover 158, the third guide boss 120c and attached malecot holding tube 160 move, and the fourth guide boss 120d and attached claw-shaft 162 each move laterally to the right by 8 mm. After the claw 161 has released the malecot 105 during Step 8, the shunt assembly 102 is held by the shroud 168. Accordingly, in Step 9, the transfer tube 152 moves to the right and sheaths the remainder of the collapsed malecot 105 into the transfer tube 152, as shown in FIG. 25. This also moves the transfer tube 152 further over the shroud 168 and the shunt body 103 which is disposed within the shroud 168. As shown in FIG. 25, the malecot holding tube cover 158, malecot holding tube cover 160 and claw-shaft 162 (with the claw 161 open) move to the right out of the way of the transfer tube 152.

At the end of Step 9, the shunt assembly 102 and shroud 168 are sheathed within the transfer tube 152. In addition, the transfer tube 152, shunt assembly 102 and shroud 168 have been flushed with a flushing fluid. The sheath tether 166 is released from the shroud tether retainer 164 by loosening the thumb screw 173. The first flushing adapter 172 is released from the transfer support tube 153 by releasing the second fitting 177, and the transfer tube 152, shunt assembly 102 and shroud 168 are removed from the transfer support tube 153 by sliding them out of the transfer support tube 153.

The endovascular shunt assembly comprising the shunt assembly 102 and shroud 168 sheathed within transfer tube 152 is now fully prepared to be loaded into the deliver catheter for use. The delivery catheter is then used to insert the shunt assembly 102 into the vascular system of a patient, and implant the shunt 103 in the patient. Exemplary devices and methods for using the shunt assembly 102 to implant the shunt body 103 are disclosed in the above-incorporated patent and application publications.

Turning now to FIGS. 28-49, another embodiment of an endovascular shunt loader 300 for preparing an endovascular shunt assembly 102 for use and loading the endovascular shunt assembly 102 onto a delivery catheter 302 is shown. The shunt assembly 102 may be the same shunt assembly 102 described herein for use with the shunt loader 100, or it may be a different shunt assembly 102. The shunt loader 300 will be described for use with the shunt assembly 102, with the understanding that the shunt loader 300 is not limited to use with the shunt assembly 102.

The endovascular shunt loader 300 differs from the endovascular shunt loader 100 in a number of respects. For one, the shunt loader 300 is configured to load the shunt assembly 102 directly into the delivery catheter 302, instead of loading the shunt assembly 102 into a transfer tube 152 which is then used to transfer the shunt assembly 102 into a delivery catheter (same or similar to the delivery catheter 302). In addition, the shunt loader 300 does not use a guide base and moving carriage to laterally move the guide bosses, as with the shunt loader 100. Instead the guide bosses of the shunt loader 300 are moved manually—directly by the hand of a user grasping a boss and sliding it laterally. Other differences will be apparent in the description and drawings of the shunt loader 300.

Figure 28:
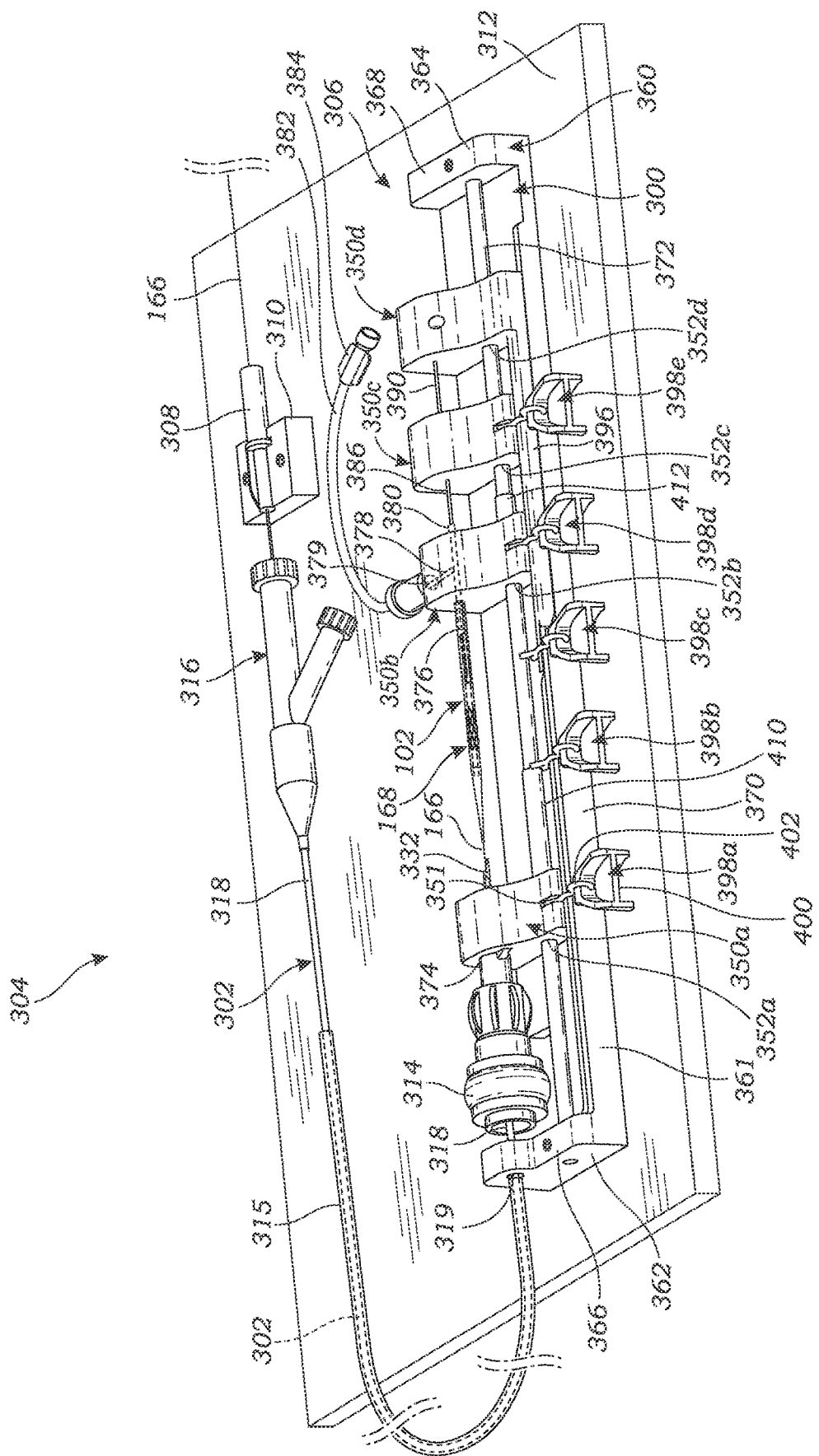
FIG. 28 is a front perspective view of a shunt loading system and shunt assembly installed thereon in an initial setup configuration, according to another embodiment of the disclosed inventions.
Figure 29:
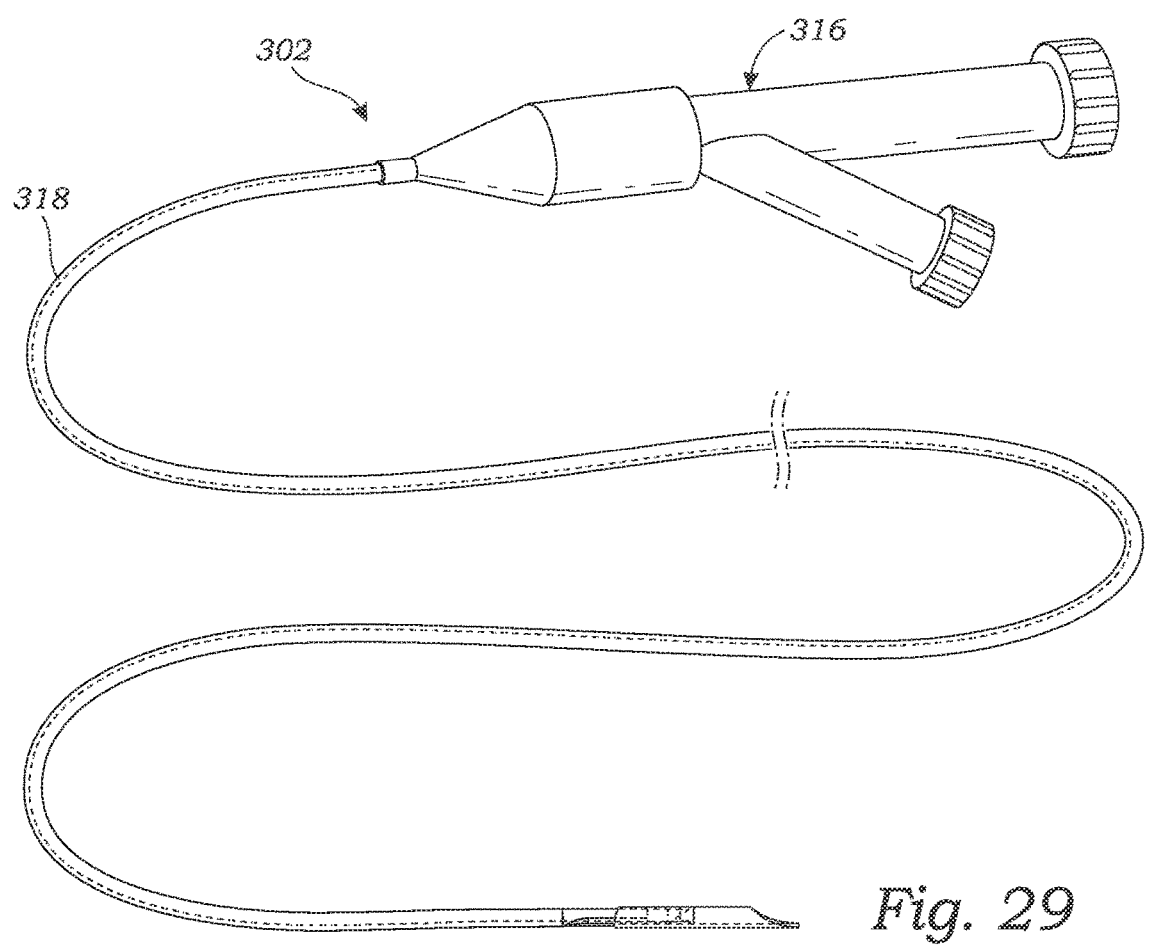
FIG. 29 is an enlarged, perspective view of the delivery catheter in the shunt loading system of FIG. 28, according to one embodiment of the disclosed inventions.

As shown in FIG. 28, the shunt loading system 304 includes the shunt loader 300, a mounting assembly 306, the shunt assembly 102, and the delivery catheter 302. In FIG. 28, the shunt loading system 304 is shown in an initial setup in which it is ready to be used to prepare the shunt assembly 102 and delivery catheter 302 for use in implanting the shunt assembly 102, including flushing the shunt assembly 102 and delivery catheter 302, and loading the shunt assembly 102 into the delivery catheter 302.

In the initial setup of the shunt loading system 304, the delivery catheter 302 and shunt loader 300 are secured to the mounting assembly 306, and the shunt assembly 102 is installed on the shunt loader 300. Accordingly, the components of the shunt loading system 304 are secured to the mounting assembly 306, and may be packaged for shipping and storage without damaging the system 304.

The mounting assembly 306 includes a base 312 and a torquer holder 310 mounted to the base 312. The torquer holder 310 is configured to receive and hold a torquer 308 installed on a proximal end of the shroud tether 166 that extends through a proximal delivery catheter fitting 316 (e.g., a Luer assembly 316). The torquer 308 may snap-fit into the torquer holder 310 to hold the torquer 308 in place, thereby securing the proximal end of the delivery catheter 302 to the mounting assembly 306. The delivery catheter 302 is also held by a compression fitting 314 which is attached to the shunt loader 300 (more specifically, the compression fitting 314 is attached to a Luer fitting which is in turn attached to a delivery catheter guide boss 350*a* of the shunt loader 300). The shunt loader 300 is mounted to the base 312 using a plurality of fasteners, adhesive or other suitable fastening method.

The mounting assembly 306 may also include a protective cover tube 315 installed on the delivery catheter 302. The protective cover tube 315 extends from proximate the proximal wall 366 of the shunt loader 300 to a distance away from a proximal catheter fitting 316. The cover tube 315 is shorter than the length of the delivery catheter 302 between the proximal wall 366 of the shunt loader 300 and the proximal catheter fitting 316 so that the cover tube 315 does not prevent the delivery catheter 302 from being advanced distally through the hole 319 in the proximal wall 366 of the shunt loader 300 during the loading process, as described below.

Figure 30:
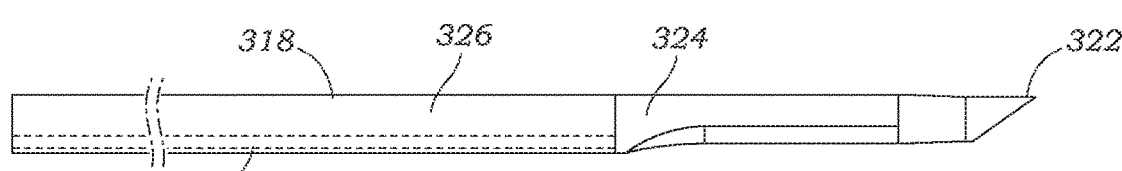
FIG. 30 is an enlarged, side view of the needle and catheter of the delivery catheter of FIGS. 28, 28A-28B and 30, according to one embodiment of the disclosed inventions.
Figure 31:
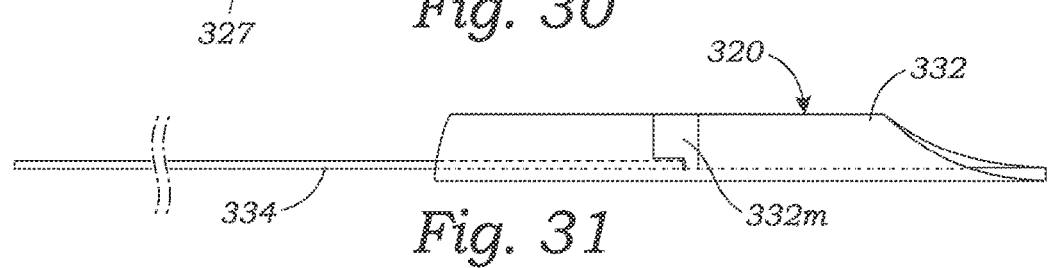
FIG. 31 is an enlarged, side view of the needle guard of the delivery catheter of FIGS. 28, 28A-28B and 30, according to one embodiment of the disclosed inventions.

As shown in FIGS. 29-32, the delivery catheter 302 comprises an elongate tubular catheter 318, a needle 322, and a needle guard assembly 320 (also referred to as a "shuttle 320"). The needle 322 is attached to the distal end of the catheter 318. The needle 322 has a needle lumen 324 in communication with a main lumen 326 of the catheter 318. An exemplary embodiment of the needle 322 is depicted in FIG. 30. Referring to FIG. 31, the needle guard assembly 318 includes a needle guard 332 attached to the distal end of one or more pull wires 334. The pull wires 334 may be disposed in a pull wire lumen 327 of the tubular catheter 318, and extend from the needle guard 332 to the proximal catheter fitting 316 where the pull wires 326 may be manipulated to move the needle guard 332. The catheter 318 extends into the left side of the shunt loader 300 through a hole 319 in the proximal wall 366, through the compression fitting 314 and through the delivery catheter guide boss 350*a*. The compression fitting 314 can be tightened to retain the catheter 318 so that the catheter 318 (and needle 322 and needle guard 332) moves along with the delivery catheter guide boss 350*a*. The compression fitting 314 may be loosened to allow removal of the catheter 318.

Figure 32:
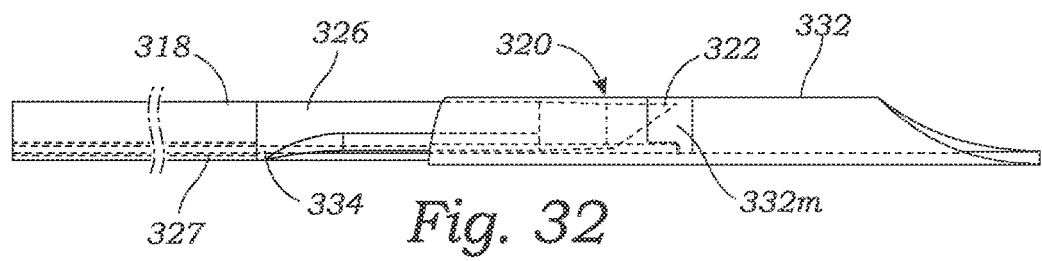
FIG. 32 is an enlarged, side view of the needle, catheter and needle guard assembly of the delivery catheter of FIGS. 28, 28A-28B and 30, according to one embodiment of the disclosed inventions.

The needle guard 332 is movable longitudinally relative to the needle 322 using the pull wires 334 such that the needle guard 332 may be selectively positioned over the needle 322 or pulled back to expose the needle 322 through the distal end of the needle guard 332. In the initial setup, and throughout the loading procedure, the needle 322 is locked in place relative to the needle guard 332 with the needle 322 enclosed within the needle guard 332, as depicted in FIG. 32.

The shunt assembly 102 is the same shunt assembly 102 described above with respect to the shunt loader 100, and depicted in FIG. 11. Again, it is understood the shunt loading system 304 (and components thereof) is not limited to use with the shunt assembly 102, but may be used to load any suitable endovascular device, such as a shunt, stent, or other implantable medical device.

Figure 33:
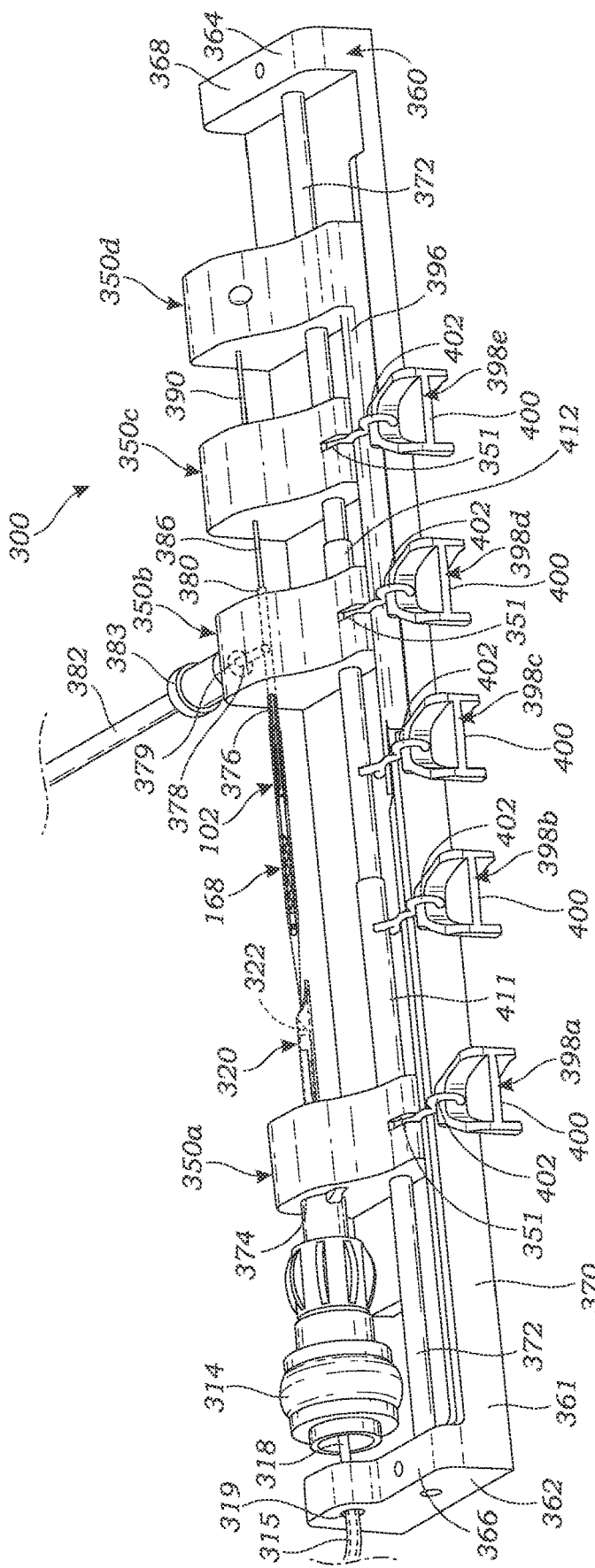
FIG. 33 is front, perspective view of the shunt loader of FIG. 28 in an initial setup configuration, according to one embodiment of the disclosed inventions.
Figure 34:
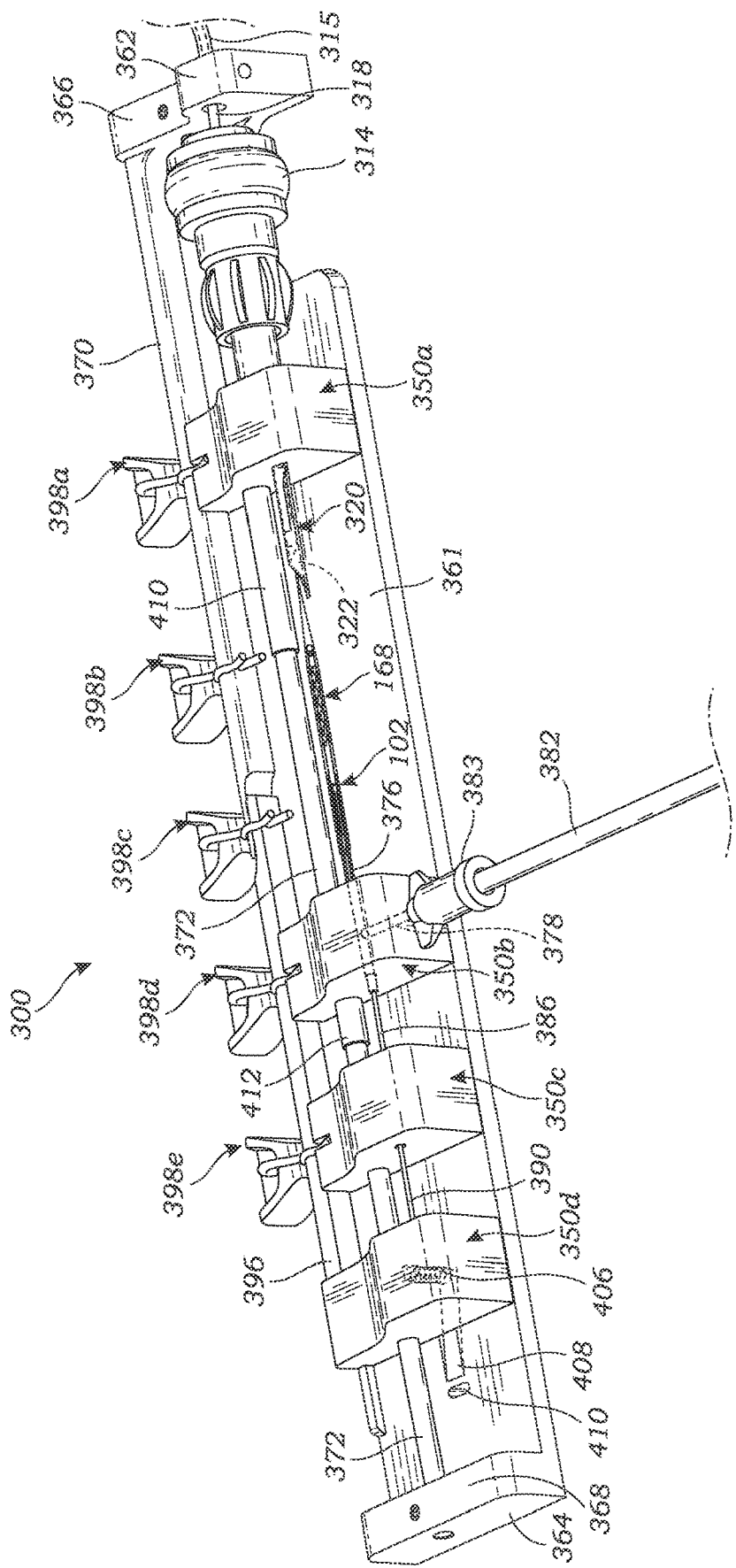
FIG. 34 is rear, perspective view of the shunt loader of FIG. 28 in an initial setup configuration, according to one embodiment of the disclosed inventions.
Figure 35:
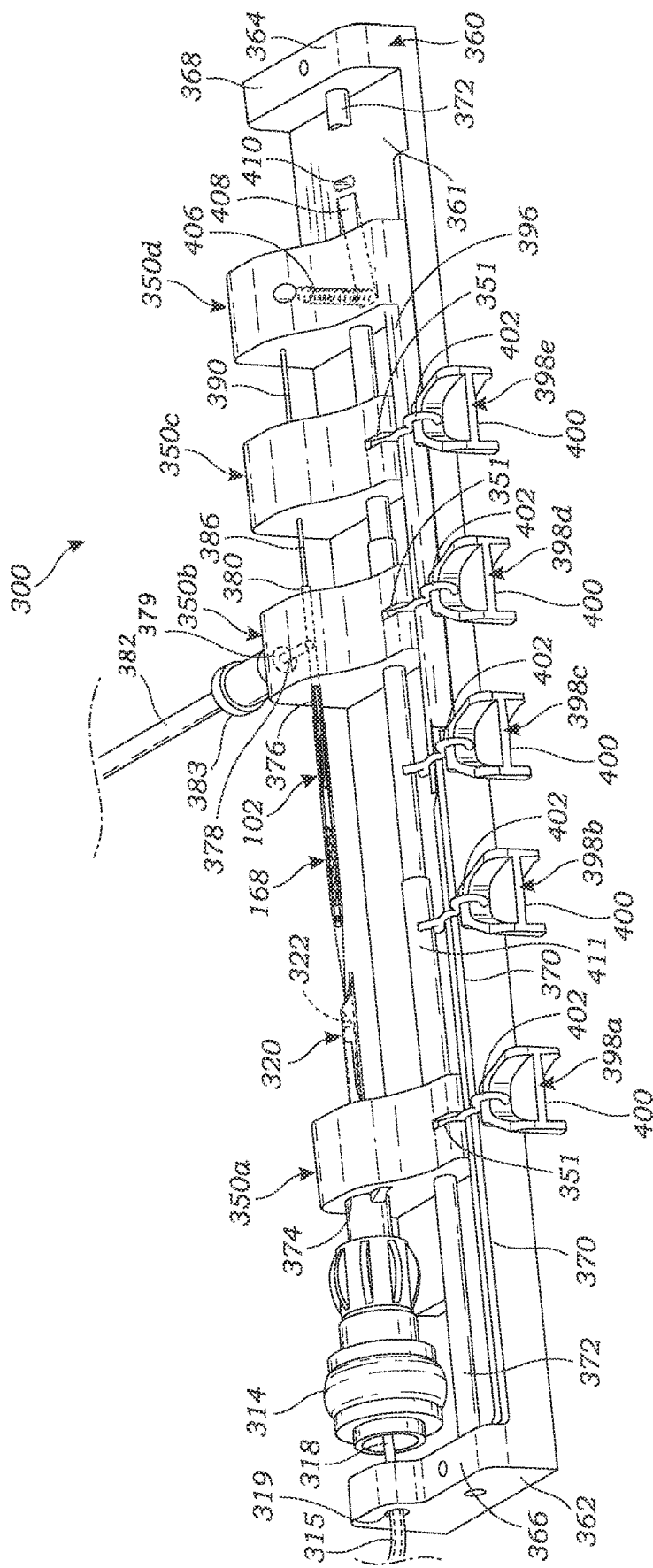
FIG. 35 is a front, perspective view of the shunt loader of FIG. 28 in an initial setup configuration showing details of the locking pin, according to one embodiment of the disclosed inventions.

Referring now to FIGS. 33-35, the shunt loader 300 comprises a loader base 360 having a proximal end 362 and a distal end 364. The base 360 has a bottom 361 comprising a rectangular plate, a proximal wall 366 extending upward from the bottom 361 at the proximal end 362 and a distal wall 368 extending upward from the bottom 361 the distal end 364. The bottom 361 has a rectangular cut-out in the proximal, back part of the bottom 361 to accommodate, and provide access to, the compression fitting 314 so that the compression fitting 314 can be manually adjusted by rotating an adjustment ring on the compression fitting 314. The base 360 also includes a front wall 370 extending upward from the bottom along a front of the bottom 361. The front wall 370 extends longitudinally from the proximal end 362 to about the middle of the base 360.

The shunt loader 300 also includes a boss rod 372 extending longitudinally across the base 360, and having a first end attached to the proximal wall 366 and a second end attached to the distal wall 368. A plurality of guide bosses 350*a*, 350*b*, 350*c* and 350*d* are slidably mounted on the boss rod 372 by respective apertures 352*a*, 352*b*, 352*c* and 352*d* which slidably receive the boss rod 372. The bottom of each guide boss 350 may sit on the bottom 361 of the base 360 and is slidable longitudinally along the bottom 361.

The delivery catheter guide boss 350a is configured to move the delivery catheter 302 during the shunt loading procedure. A distal end 374 of the compression fitting 314 is attached to the proximal face of the delivery catheter guide boss 350a. The compression fitting 314 may be attached to the delivery catheter guide boss 350a by any suitable method, including, for example, bonding, mating threads, fasteners, etc. The delivery catheter 302 inserts through the compression fitting 314 and the compression fitting 314 is tightened to retain the delivery catheter 302; because the compression fitting 314 is attached to the delivery catheter guide boss 350a, longitudinal movement of the delivery catheter guide boss 350a moves the delivery catheter 302 longitudinally. The catheter 318 (and attached needle 332) and pull wire(s) 334 (and needle guard 332) are longitudinally fixed together (such as by the catheter fitting 316) such that they move together (i.e., move the same longitudinally) in response to longitudinal movement of the delivery catheter guide boss 350a.

A first bump tube 411 is attached to the distal face of the delivery catheter guide boss 350a. The first bump tube 411 is slidably received on the boss rod 372. As the delivery catheter guide boss 350a is moved distally, the first bump tube 411 slides on the boss rod 372. During the loading procedure as described below, as the delivery catheter guide boss 350a is moved distally, the first bump tube 411 contacts the proximal face of the malecot holding tube guide boss 350b. Accordingly, depending on the particular step of the procedure, the contact of the first bump tube 411 with the proximal face of the malecot holding tube guide boss 350b either stops the distal movement of the delivery catheter guide boss 350a, or pushes the malecot holding tube guide boss 350b distally along with the delivery catheter guide boss 350a.

The malecot holding tube guide boss 350b is configured to move a malecot holding tube 376 which is attached to the malecot holding tube guide boss 350b. The malecot holding tube 376 inserts partway into a proximal face of the malecot holding tube guide boss 350a and extends proximally from such proximal face. The malecot holding tube 376 is fixed to the malecot holding tube guide boss 350b by any suitable method, such as bonding, press fit, set screw, mating threads, etc. The malecot holding tube 376 is in fluid communication with a flush lumen 378 within the malecot holding tube guide boss 350b. The flush lumen 378 is also in fluid communication with an aperture 379 on the back of the malecot holding tube guide boss 350b. A first end of a flush tube 382 is connected to the back of the malecot holding tube guide boss 350b in fluid communication with the aperture 379. The first end of the flush tube 382 may have a fitting 383 for making the connection to the back of the malecot holding tube guide boss 350b. The fitting 383 may snap into the malecot holding tube guide boss 350b or they may have mating threads. A Luer fitting 384 is attached to the second end of the flush tube 382. The malecot holding tube guide boss 350b has a lumen 381 extending distally from the flush lumen 378 through the distal face of the malecot holding tube guide boss 350b. A sealing tube 380 is inserted into the lumen 381. The sealing tube 380 has an inside diameter that is slightly smaller than the malecot holding tube 376 such that when the shaft 387 of the claw assembly 386 is inserted through the sealing tube 380 and malecot holding tube 376, the cross-sectional flow area between the shaft 387 and the sealing tube 380 is smaller than the cross-sectional flow area between the shaft 387 and the malecot holding tube 376.

A second bump tube 412 is attached to the distal face of the malecot holding tube guide boss 350b. The second bump tube 412 is slidably received on the boss rod 372. As the malecot holding tube guide boss 350b is moved distally, the second bump tube 412 slides on the boss rod 372. During the loading procedure as described below, as the malecot holding tube guide boss 350b is moved distally, the second bump tube 412 contacts the proximal face of the claw guide boss 350c. Accordingly, depending on the particular step of the procedure, the contact of the second bump tube 412 with the proximal face of the claw guide boss 350c either stops the distal movement of the malecot holding tube guide boss 350b, or pushes the claw guide boss 350c distally along with the malecot holding tube guide boss 350b.

Figure 36:
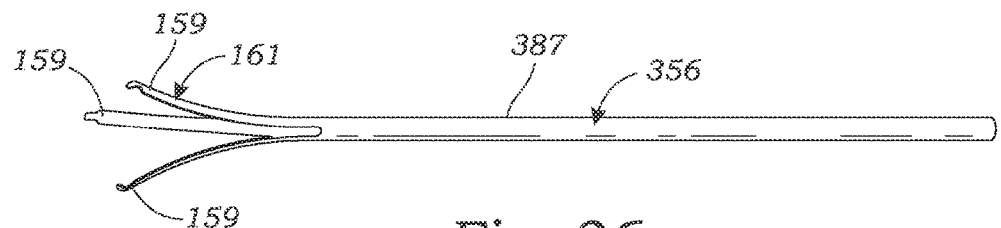
FIG. 36 is a side, perspective view of a claw assembly of the shunt loader of FIGS. 28 and 33, according to one embodiment of the disclosed inventions.
Figure 37:
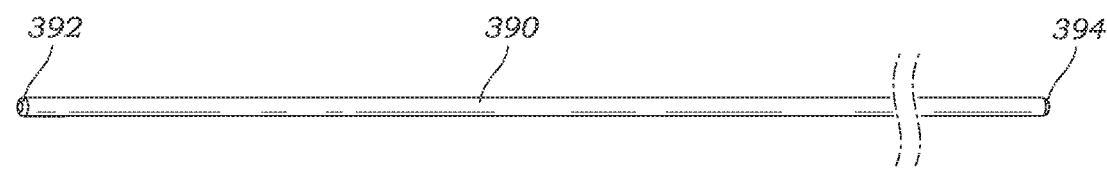
FIG. 37 is a side, perspective view of the chase pin of the shunt loader of FIGS. 28 and 33, wherein the claw is in an open position, according to one embodiment of the disclosed inventions.
Figure 38:
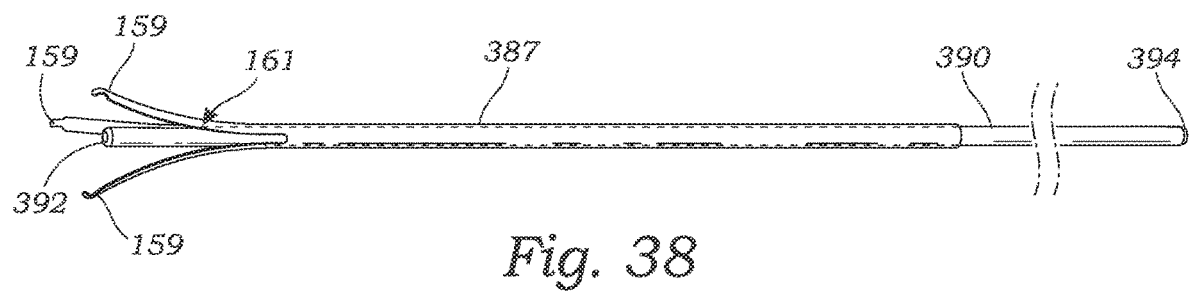
FIG. 38 is a side, perspective view of the claw assembly and chase pin assembly of the shunt loader of FIGS. 28 and 33, according to one embodiment of the disclosed inventions.

The claw guide boss 350c is configured to move a claw assembly 386 which is attached to the claw guide boss 350c. The claw assembly 386 includes a claw 161 attached to the proximal end of a shaft 387. The shaft 387 inserts into a hole in the claw guide boss 350c, and is attached to the claw guide boss 350c by any suitable method, such as a set screw, bonding, press fit, mating threads, etc. Referring to FIG. 36, the claw assembly 386 is similar to the claw assembly 162, and operates in the same manner as the claw assembly 162. The main difference is that the shaft 387 of the claw assembly 386 is a tube having a lumen for receiving a chase pin 390 (see FIG. 37). The claw assembly 386 includes a claw 161 having a plurality of prongs 159 (in this case, 3 prongs 159). As shown in FIG. 37, the chase pin 390 comprises an elongate rod having a proximal end 392 and a distal end 395. The claw 161 is biased to an open position, as described above. Same as the claw assembly 162, the claw assembly 386 releasably attaches to the malecot 105. As shown in FIG. 38, the chase pin 390 inserts into the lumen of the shaft 387 such that the proximal end 392 of the chase pin 390 extends to proximate the prongs 159 and the distal end of the chase pin 390 extends distally out of the distal end of the shaft 387. The claw assembly 386 and chase pin 390 extend through the sealing tube 380, through the malecot holding tube guide boss 350b, and into the malecot holding tube 376 to a position within the malecot holding tube 376 proximal to the proximal face of the malecot holding tube guide boss 350b.

The chase pin guide boss 350d is configured to move the chase pin 390. The chase pin 390 extends distally through the claw guide boss 350c (within the shaft 387 of the claw assembly 386) to the chase pin guide boss 350d. The distal end 394 of the chase pin 390 inserts into a hole in the chase pin guide boss 350d, and is attached to the claw guide boss 350c by any suitable method, such as, bonding, press fit, a set screw, mating threads, etc. Hence, longitudinal movement of the chase pin guide boss 350d moves the chase pin 390 longitudinally.

The chase pin guide boss 350d is connected to a distal end of a connecting arm 396 (also referred to as a sled 396) which extends proximally from the proximal face of the chase pin guide boss 350d. The connecting arm 396 is positioned at the front of the bottom 361 of the base 360 such that it is an extension of the front wall 370 of the base 360. In the initial setup, the proximal end of the connecting arm 396 is proximate, or overlapping, the distal end of the front wall 370. The connecting arm 396 allows the malecot holding tube guide boss 350b and the claw guide boss 350c to be connected to the connecting arm 396 such that the three bosses 350b, 350c and 350d may be moved together synchronously.

Referring to FIGS. 34 and 35, the chase pin guide boss 350*d* also has a spring-loaded locking pin 406 which extends out of the bottom of the chase pin guide boss 350*d*. The spring-loaded locking pin 406 rides on a ramp 408 in the bottom 361 of the loader base 360 as the chase pin guide boss 350*d* is moved distally. The proximal end of the ramp 408 is below the top surface of the bottom 361 and distal end of the ramp 408 is flush with the top surface of the bottom 361 such that the ramp 408 angles upward from its proximal end to distal end. The bottom 361 of the loader base 360 has a locking pin slot 410 just distal of the distal end of the ramp 408. When the chase pin guide boss 350*d* is moved distally to the position in which the locking pin 406 is located over the locking pin slot 410, the spring-loaded locking pin 406 pushes the pin 406 into the locking pin slot 410, thereby locking the chase pin guide boss 350*d* in place.

The shunt loader 300 also has a plurality of removable retainers 398, including a delivery catheter boss retainer 398*a*, a stop retainer 398*b*, a connecting arm retainer 398*c*, a malecot holding tube boss retainer 398*d*, and a claw boss retainer 398*e*. Each of the retainers 398 comprises a cotter pin 402 and a pull tab 400 connected to the cotter pin 402. The delivery catheter boss retainer 398*a* is removably installed in a first hole in the front wall 370 such that the cotter pin 402 extends into the retaining slot 351 of the delivery catheter guide boss 350*a*. The delivery catheter boss retainer 398*a* prevents the delivery catheter guide boss 350*a* from moving when installed, and allows the delivery catheter guide boss 350*a* to move longitudinally when it is removed.

The stop retainer 398*b* is removably installed in a second hole in the front wall 370 such that the cotter pin 402 extends toward the boss rod 372. The stop retainer 398*b* will stop the delivery catheter guide boss 350*a* from moving distally past the stop retainer 398*b* when the distal face of the delivery catheter guide boss 350*a* contacts the stop retainer 398*b*, the during the shunt loading procedure, as described below.

The connecting arm retainer 398*c* is removably installed through a third hole in the front wall 370 and through a connecting arm hole in the connecting arm 396. Thus, the connecting arm retainer 398*c* prevents the connecting arm 396 from moving when installed, and allows the connecting arm 396 to move longitudinally when removed.

The malecot holding tube boss retainer 398*d* is removably installed through a hole in the connecting arm 396 such that the cotter pin 402 extends into the retaining slot 351 of the malecot holding tube guide boss 350*b*. Hence, the malecot holding tube retainer 398*d* connects the malecot holding tube guide boss 350*b* to the connecting arm 396 such that it tracks the longitudinal movement of the connecting arm 396 (i.e., prevents movement when the connecting arm 396 is stationary and moves longitudinally when the connecting arm 396 moves longitudinally) when installed, and allows the malecot holding tube guide boss 350*b* to move independent of the connecting arm 396 when removed.

The claw boss retainer 398*e* is removably installed through a hole in the connecting arm 396 such that the cotter pin 402 extends into the retaining slot 351 of the claw guide boss 350*c*. Hence, the claw boss retainer 398*e* connects the claw guide boss 350*c* to the connecting arm 396 such that the claw guide boss 350*c* tracks the longitudinal movement of the connecting arm 396 (i.e., prevents movement when the connecting arm 396 is stationary and moves longitudinally when the connecting arm 396 moves longitudinally) when installed, and allows the claw guide boss 350*c* to move independent of the connecting arm 396 when removed.

With reference to FIGS. 28, 28A-28B and 39-49, a method of using the shunt loading system 304 to flush the delivery catheter 302 and shunt assembly 102, and load the shunt assembly 102 into the delivery catheter 302, in preparation for inserting the delivery catheter 302 into a patient and implanting the shunt assembly 102, will now be described. FIGS. 28, 39, 41, 43, 45, and 47 illustrate the steps of the operation of the shunt loader 300, while FIGS. 28A-28B, 40, 42, 44, 46 and 47 illustrate the components of the delivery catheter 302, shunt assembly 102 and loading components of the shunt loader 300 at each step of the method without showing the entire shunt loader 300. It should be understood that FIGS. 28A-28B, 40, 42, 44, 46 and 47 show the components of the delivery catheter 302, shunt assembly 102 and loading components of the shunt loader 300 as they are positioned on the shunt loader 300 at each respective step of the method.

First, the initial setup of the shunt loading system 304 will be described. As shown in FIG. 28, each of the guide bosses 350 is positioned in their initial positions and the respective retainers 398 are installed to set and maintain these positions. The connecting arm 396 is in its initial position and connected to the front wall 370 by retainer 398*c*.

The shunt assembly 102 is installed on the shunt loader 300 by attaching the claw 161 to the malecot 105. This may be accomplished by removing the malecot holding tube boss retainer 398*d* and moving the malecot holding tube guide boss 350*b* and malecot holding tube 376 distally until the claw 161 extends out of the proximal end of the malecot holding tube 376, which allows the claw 161 to open. The malecot 105 is positioned in the claw 161 and then the malecot holding tube guide boss 350*b* and malecot holding tube 376 are moved proximally such that malecot holding tube 376 moves back over the claw 161 thereby closing the claw 161 onto the malecot 105. The malecot holding tube boss retainer 398*d* is then installed to hold the malecot holding tube guide boss 350*b* in place.

The shroud tether 166 is inserted through the needle 322 and catheter 318 such that the proximal end of the tether 166 extends out of the proximal catheter fitting 316 and the distal end of the shroud tether 166 and the shroud 168 are distal of the needle 322 and needle guard 332. The catheter 318, needle 322 and needle guard 322 of the delivery catheter 302, and the shroud 168 are inserted through the protective cover 315, through the hole 319 on the proximal wall 366, through the compression fitting 314 (compression fitting 314 is in its loosened position) and through the delivery catheter guide boss 350*a*. The compression fitting 314 is tightened to retain the catheter 318. The compression fitting 314 retains the catheter 318 in place, and allows the delivery catheter 318 (and needle 322 and needle guard 332) to be moved when the delivery catheter guide boss 350*a* is moved.

Figure 40:
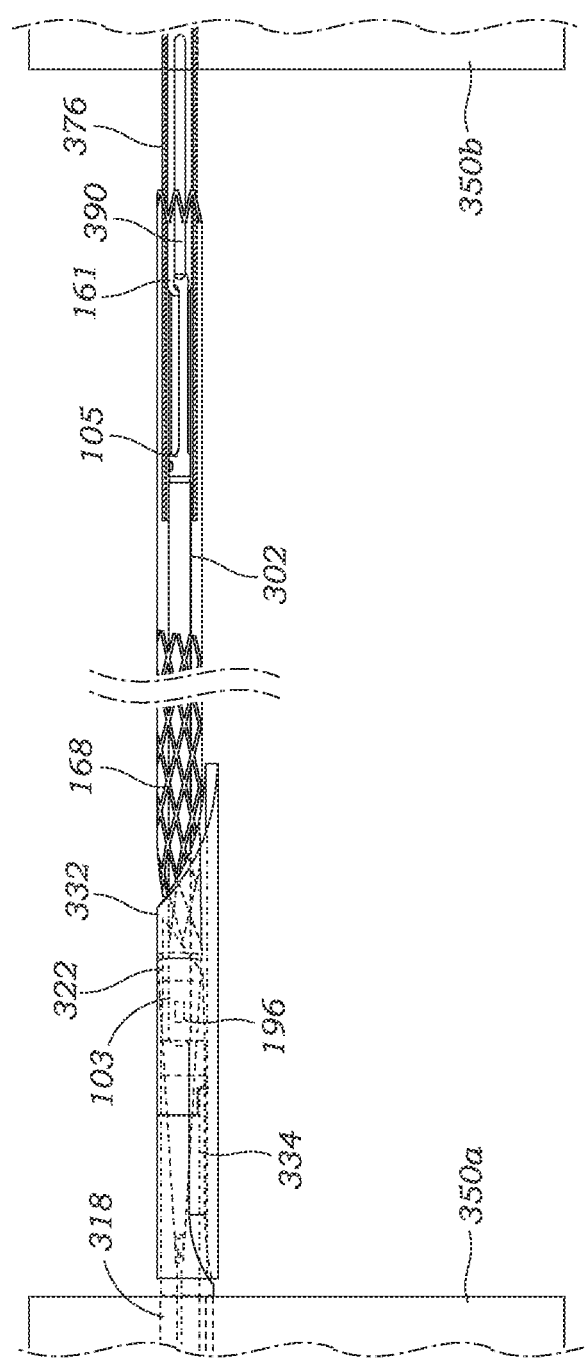
FIG. 40 is a side, partial sectional view depicting the shunt assembly delivery catheter of FIGS. 28 and 33 illustrating Step 1 of a method of using the shunt loading system of FIG. 28, according to one embodiment of the disclosed inventions.

The shroud 168 extends distally over the shunt body 103 such that the shunt body 103 extends proximally from the malecot 105 into the shroud 168. The shroud 168 also extends over the malecot holding tube 376 (and the malecot 105 and claw 161), as shown in FIG. 40.

The chase pin 390 inserts into the claw shaft 387 such that the proximal end 392 of the chase pin 390 is proximate the proximal end of the claw 161. The chase pin 390 extends from its proximal end 392, through the claw shaft 387, through sealing tube 380, through the malecot holding tube 376 and malecot holding tube guide boss 350*a* (within the claw shaft 387), through the claw guide boss 350*c*, and into the chase pin guide boss 350*d* where the distal end 394 of the chase pin 390 is fixed to the chase pin guide boss 350*d*.

The torquer 308 is inserted onto the distal end of the shroud tether 166. The shroud 168 is adjusted to the proper longitudinal position over the shunt malecot holding tube 376 for the initial setup, and the torquer 308 is tightened onto the shroud tether 166 at the position of the torquer holder 310. The torquer 308 is then mounted onto the torquer holder 310, thereby securing the shroud tether 166 to the mounting assembly 306.

In this initial setup position, the shunt loading system 304 can be securely shipped and stored in a sterilized condition. When the shunt loading system 304 is going to be used in a surgical procedure to implant the shunt 102 in a patient, the shunt loading system 304 is unpackaged, and the following preparation and loading method is performed.

The first step of the preparation and loading method is to ensure that the delivery catheter 302 is properly positioned to begin the preparation procedure. Notably, a proximal edge or "base" 322B of the needle 322 (i.e., the edge of the needle 322 that is welded to the reinforcing hypotube of the delivery catheter 302) can be seen in FIG. 28B, as can a marker 332M embedded in the needle guard 332. The correct setup position for the delivery catheter 302 is set by aligning the needle base 322B approximately 2-3 mm away from the distal face of the delivery catheter guide boss 350a, as illustrated in FIG. 28B. If the delivery catheter 302 is not in this setup position, then the position of the delivery catheter 302 should be adjusted by loosening the compression fitting 314, moving the delivery catheter 302 to align the proximal edge of the needle base 322B approximately 2-3 mm away from the distal face of the delivery catheter guide boss 350a, and then tightening the compression fitting 314 onto the catheter 318.

The next step is to flush the delivery catheter 302 and shunt assembly 102, with the shunt loading system 304 in the initial setup as described above and shown in FIGS. 28, 28A-28B and 33. A source of flushing fluid is connected to the proximal delivery catheter fitting 316, and injects flushing fluid into the fitting 316. The flushing fluid flows into the delivery catheter 302 thereby flushing air out of the delivery catheter 302. When flushing fluid is seen exiting the needle 322 and needle guard 332, the delivery catheter 302 is flushed. A source of flushing fluid is connected to the Luer fitting 384 and is used to inject flushing fluid into the Luer fitting 384. The flushing fluid flows through the flush tube 382 into the flush lumen 378. The flushing fluid then flows through the malecot holding tube 376 and into the shunt assembly 102, until the shunt assembly 102 is sufficiently flushed to remove air (e.g., until flushing fluid is visible flowing out of the proximal end of the shunt body 103).

Next, the shunt loader 300 is operated to load the shunt assembly 102 into the delivery catheter 302. The table of FIG. 49 shows the magnitude of the movement of each of the guide bosses 350 in inches during each of the Steps 1-5 of a method for operating the shunt loader 300 to prepare the shunt assembly 102 using the shunt loading system 304. All movements of the guide bosses 350 are in the distal direction (i.e., to the right, as the system 304 and components are oriented in the drawings). The specific magnitude of the movement of the guide bosses 350 in each of the steps of the method are exemplary for the preparation of a particular configuration and size of shunt assembly 102, and may vary depending on the design and size of the intravascular device being prepared using the shunt loader 300 and the method of using the shunt loader 300 for the particular shunt assembly.

Figure 39:
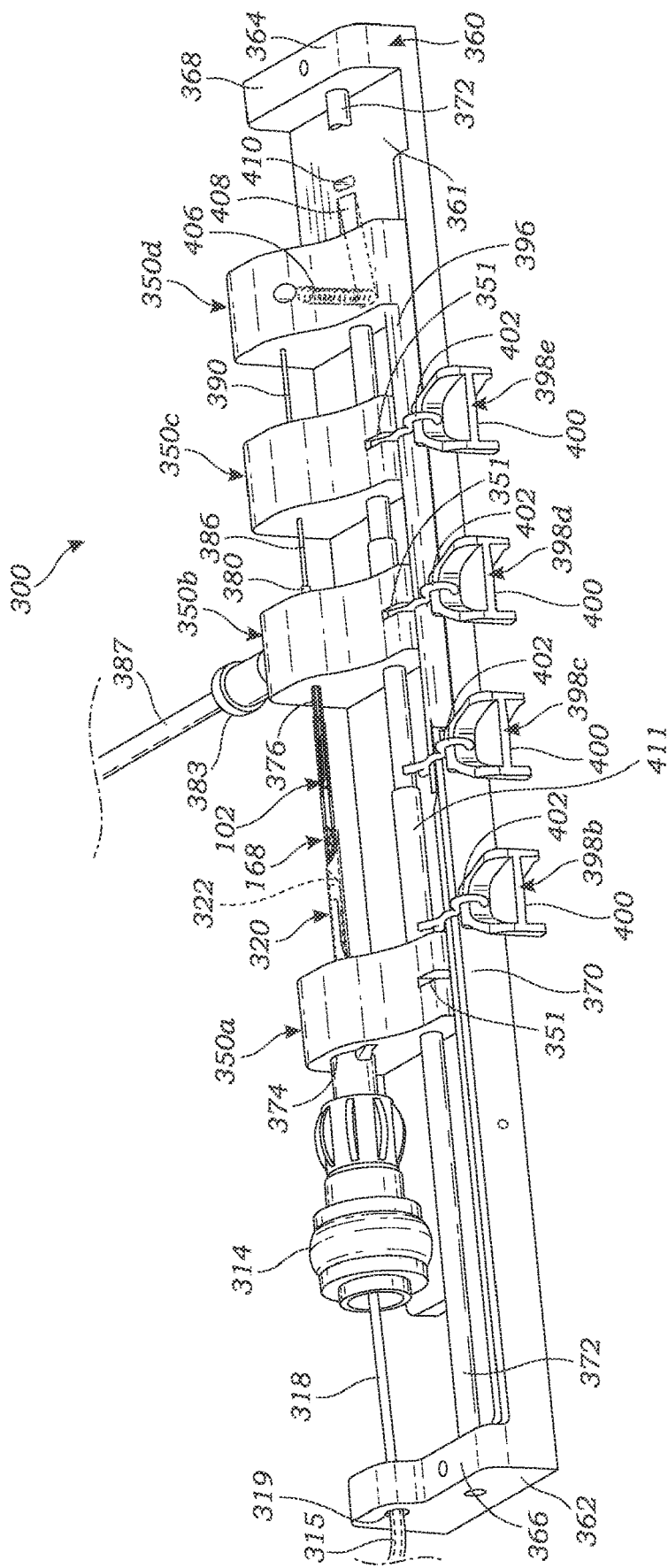
FIG. 39 is a front, perspective view of the shunt loader and shunt assembly of FIGS. 28 and 33 illustrating Step 1 of a method of using the shunt loading system of FIG. 28, according to one embodiment of the disclosed inventions.

Referring to FIGS. 39 and 40, at Step 1, the delivery catheter retainer 398a is removed, thereby allowing longitudinal movement of the delivery catheter guide boss 350a. The delivery catheter guide boss 350a is moved distally until the distal face of the delivery catheter guide boss 350a contacts the stop retainer 398b which prevents further distal movement of the delivery catheter guide boss 350a, as shown in FIG. 39. The delivery catheter 302, including the needle 322 and needle guard 332 move distally along with the delivery catheter guide boss 350a. As shown in the table of FIG. 49, at Step 1, the delivery catheter guide boss 350a moves 0.877 inches distally (i.e., to the right as shown in the figures).

As shown in FIG. 40, the distal movement of the needle 322 and needle guard 332 causes the needle 322 to capture a portion of the shroud 168 and shunt body 103. The outer diameter of the shroud 168 and shunt body 103 within the shroud 168 is slightly larger than the inner diameter of the needle 322 such that as the needle 322 is moved over the shroud 168 and shunt body 103, the shroud 168 and shunt body 103 collapse into the needle 322. As the shroud 168 and shunt body 103 are compressed/collapsed into the needle 322, the tapered section 169 of the shroud 168 is compressed onto the proximal end of the shunt body 103. As shown in FIG. 11, the shunt body 103 has a rigid, radio-opaque marker 196 in its proximal end such that when the tapered section 169 of shroud 168 is compressed onto the proximal end of the shunt body 103, the proximal end of the shunt body 103 is held tightly in place by the shroud 168 and needle 322.

Figure 41:
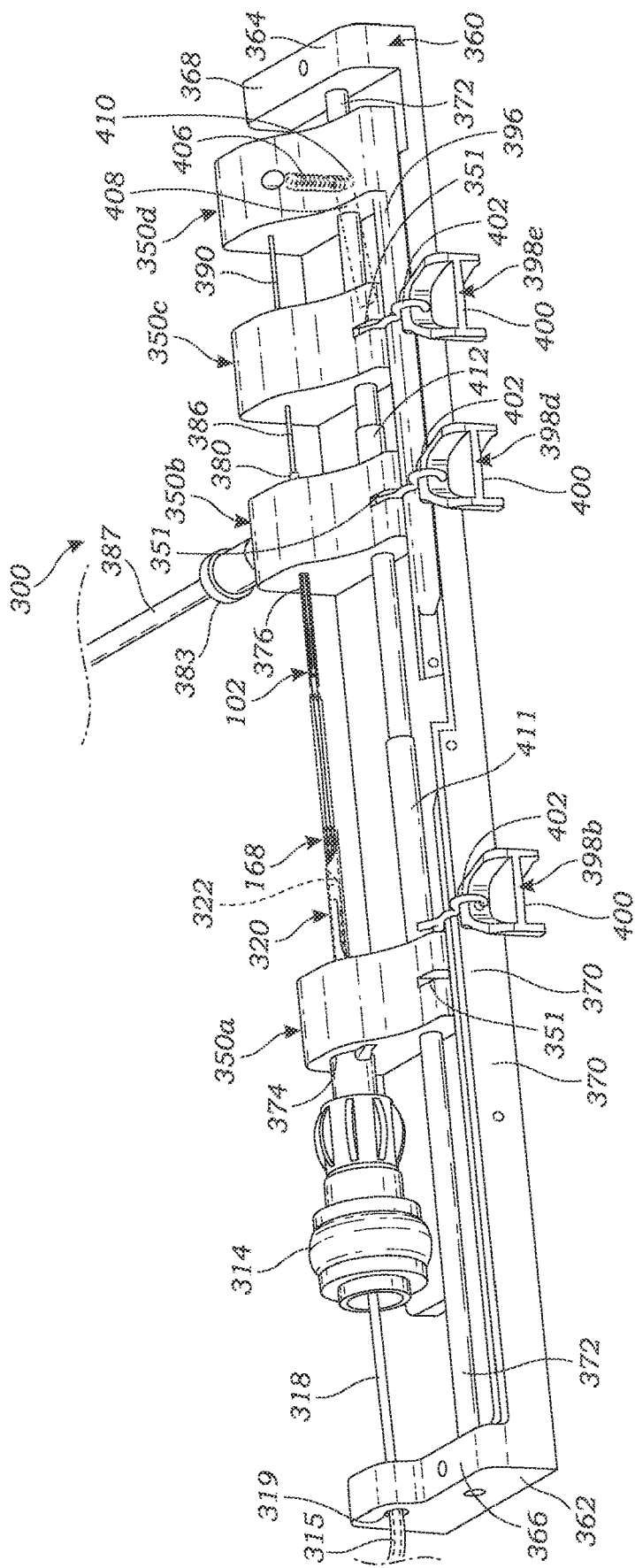
FIG. 41 is a front, perspective view of the shunt loader and shunt assembly of FIGS. 28 and 33 illustrating Step 2 of a method of using the shunt loading system of FIG. 28, according to one embodiment of the disclosed inventions.
Figure 42:
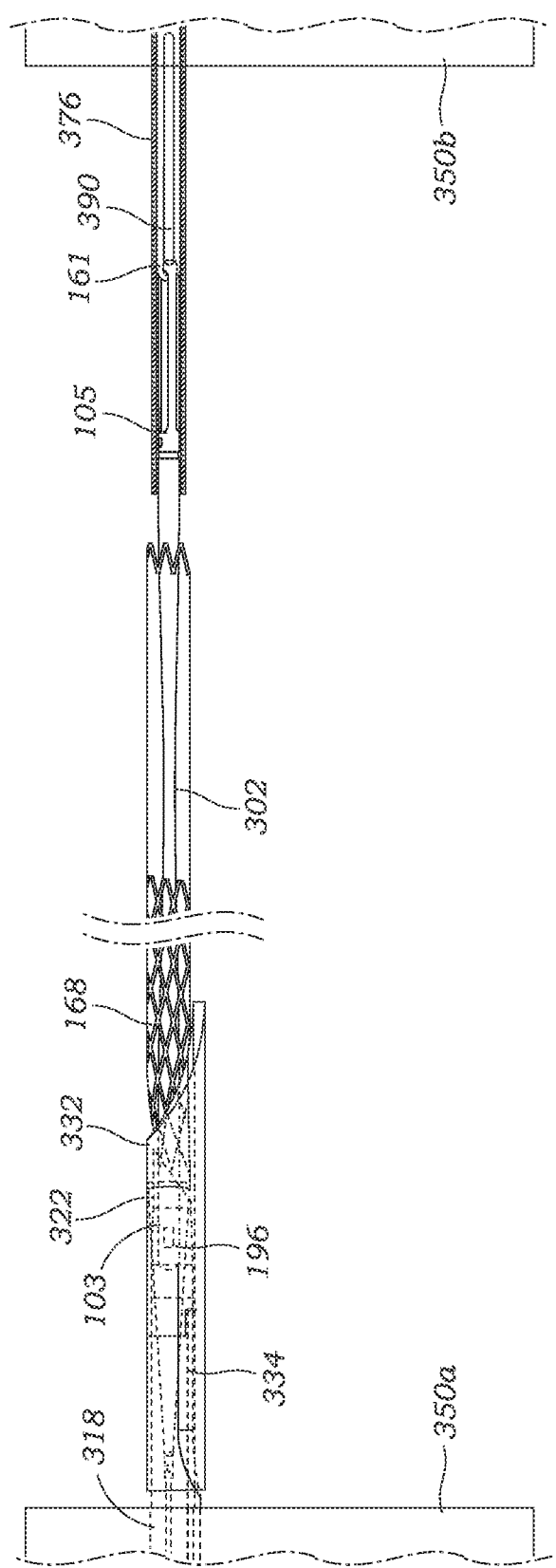
FIG. 42 is a side, partial sectional view depicting the shunt assembly delivery catheter of FIGS. 28 and 33 illustrating Step 2 of a method of using the shunt loading system of FIG. 28, according to one embodiment of the disclosed inventions.

Referring to FIGS. 41 and 42, at Step 2, the connecting arm retainer 398c is removed, thereby allowing longitudinal movement of the connecting arm 396, as well as the malecot holding tube guide boss 350b, claw guide boss 350c and chase pin guide boss 350d. As shown in the table of FIG. 49, at Step 2, the connecting arm 396, malecot holding tube guide boss 350b, claw guide boss 350c and chase pin guide boss 350d move 0.622 inches distally. The connecting arm 396, malecot holding tube guide boss 350b and attached malecot holding tube 376, claw guide boss 350c and attached claw assembly 356, and chase pin guide boss 350d and attached chase pin 390, are moved distally until the spring-loaded locking pin 406 is pushed into the locking pin slot 410 which stops the movement and locks the connecting arm 396 and chase pin guide boss 350d in place.

As depicted in FIG. 42, the claw assembly 356 pulls the attached malecot 105 and distal end of the shunt body 103 (the proximal end of the shunt body 103 is held fixed in the same lateral position by the shroud 168, as described for Step 1), thereby stretching the shunt body 103. The stretching of the shunt body 103 causes the diameter of the shunt body 103 to decrease by an effect known as "necking."

Figure 43:
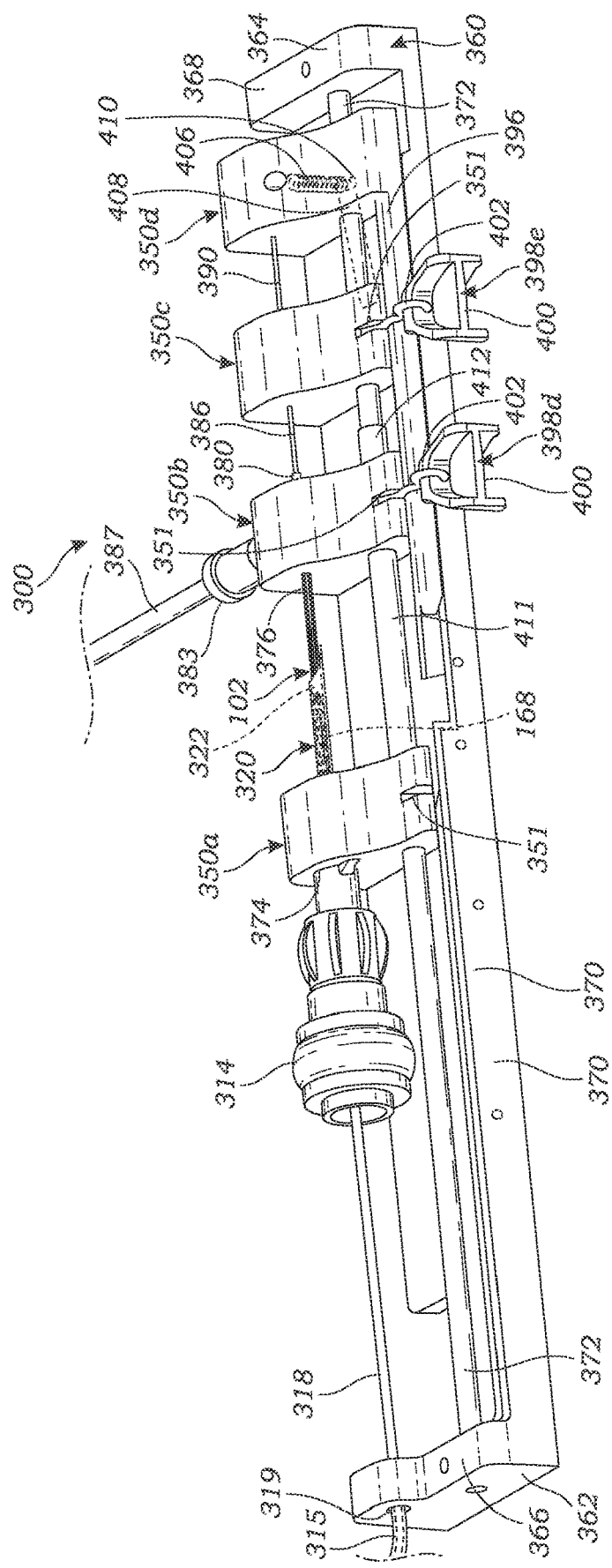
FIG. 43 is a front, perspective view of the shunt loader and shunt assembly of FIGS. 28 and 33 illustrating Step 3 of a method of using the shunt loading system of FIG. 28, according to one embodiment of the disclosed inventions.
Figure 44:
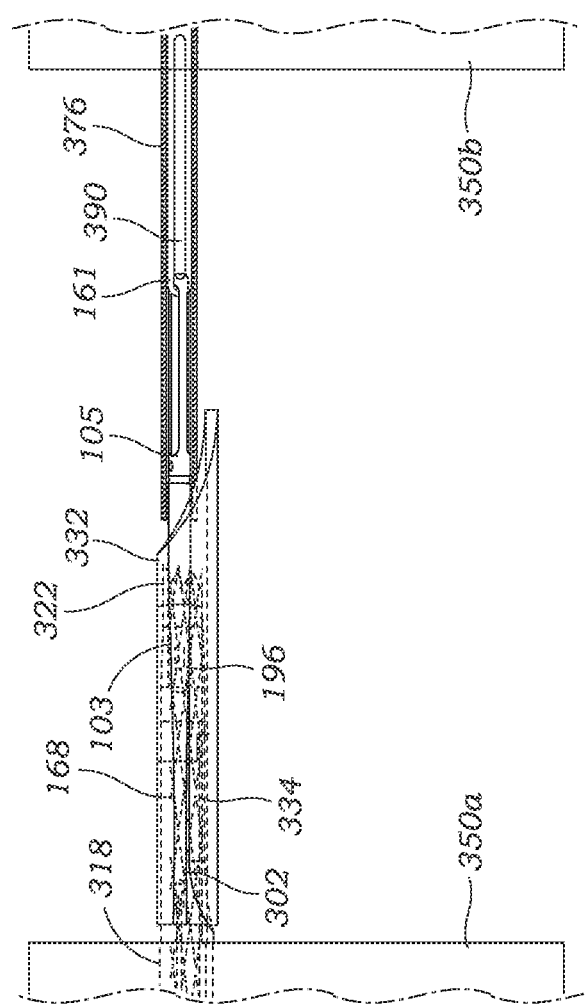
FIG. 44 is a side, partial sectional view depicting the shunt assembly delivery catheter of FIGS. 28 and 33 illustrating Step 3 of a method of using the shunt loading system of FIG. 28, according to one embodiment of the disclosed inventions.

Referring to FIGS. 43 and 44, at Step 3, the stop retainer 398b is removed, thereby allowing further longitudinal movement of the delivery catheter guide boss 350a. As shown in the table of FIG. 49, at Step 3, the delivery catheter guide boss 350a moves 1.288 inches distally. The delivery catheter guide boss 350a and attached delivery catheter 302, including the needle 322, needle guard 332 and catheter 318, are moved distally until the first bump tube 411 contacts the proximal face of the malecot holding tube guide boss 350b which stops the distal movement.

As depicted in FIG. 44, the distal movement of the delivery catheter 302 (including the needle 322, needle guard 332 and catheter 318) causes the delivery catheter 302 to capture the remainder of the shroud 168 and shunt body 103.

Figure 45:
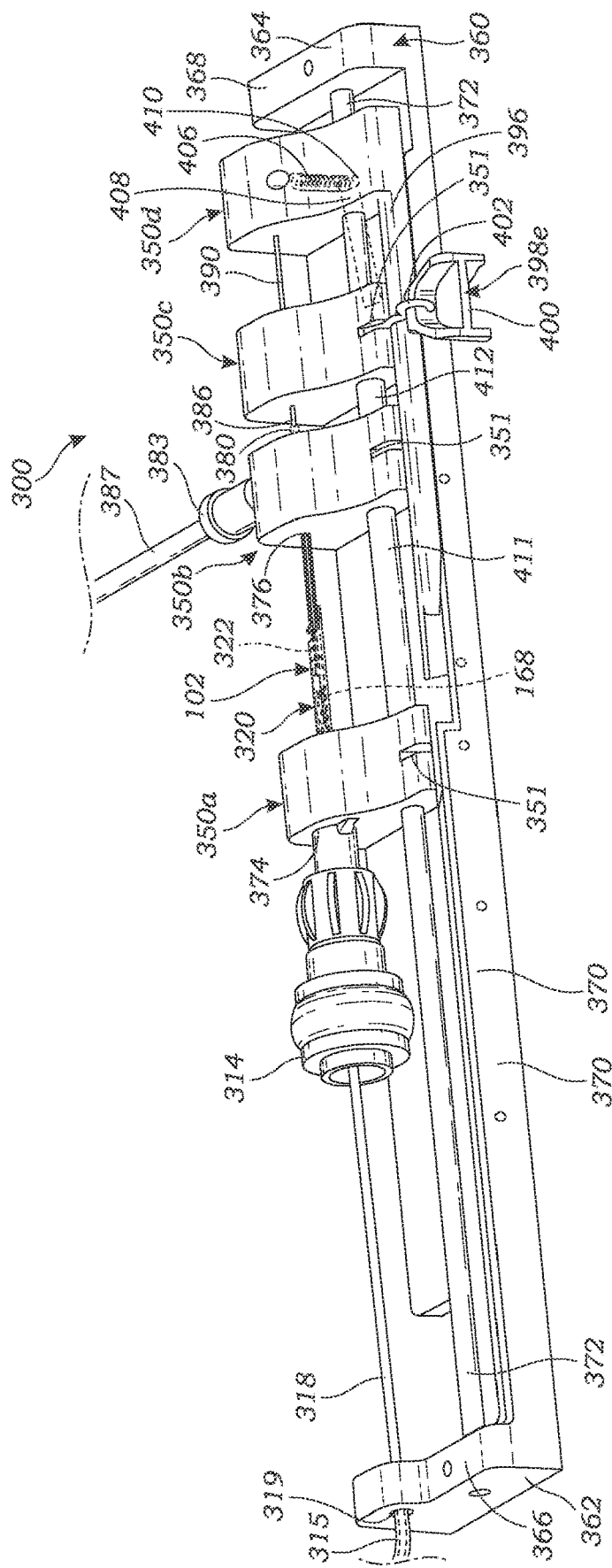
FIG. 45 is a front, perspective view of the shunt loader and shunt assembly of FIGS. 28 and 33 illustrating Step 4 of a method of using the shunt loading system of FIG. 28, according to one embodiment of the disclosed inventions.
Figure 46:
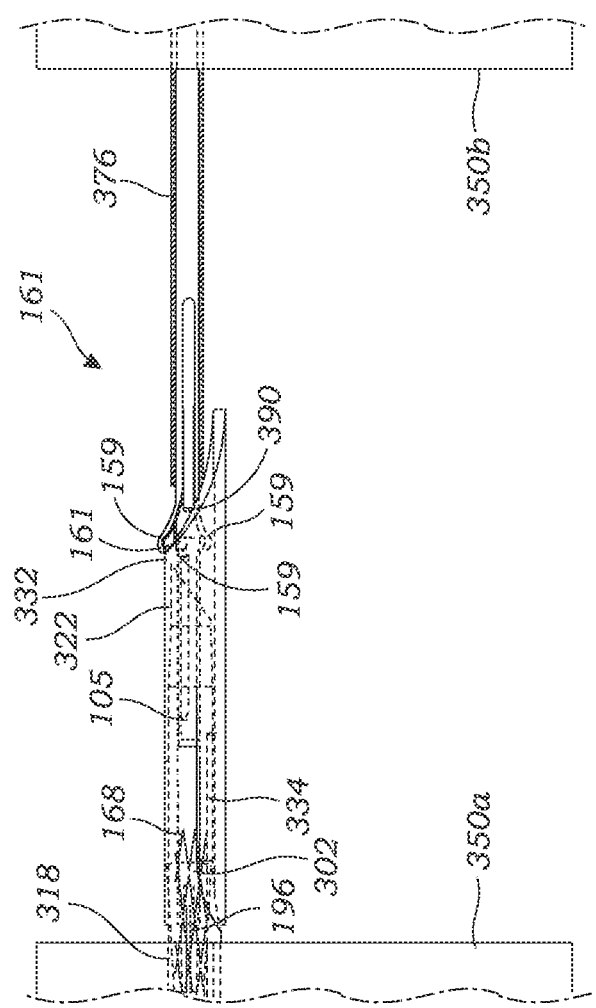
FIG. 46 is a side, partial sectional view depicting the shunt assembly delivery catheter of FIGS. 28 and 33 illustrating Step 4 of a method of using the shunt loading system of FIG. 28, according to one embodiment of the disclosed inventions.

Referring to FIGS. 45 and 46, at Step 4, the malecot holding tube retainer 398d is removed, thereby allowing concurrent longitudinal movement of the delivery catheter guide boss 350a and the malecot holding tube guide boss 350b. The concurrent movement of Step 4 is caused by moving the delivery catheter guide boss 350a distally, while the first bump tube 411 pushes the malecot holding tube guide boss 350b. As shown in the table of FIG. 49, at Step 4, the delivery catheter guide boss 350a and the malecot holding tube guide boss 350b move 0.25 inches distally. The delivery catheter guide boss 350a and attached delivery catheter 302, and the malecot holding tube guide boss 350b and attached malecot holding tube 376, are moved distally until the second bump tube 412 contacts the proximal face of the claw guide boss 350c which stops the distal movement.

As depicted in FIG. 46, the delivery catheter 302 (including the needle 322, needle guard 332 and catheter 318) is moved distally such that the needle 322 has captured part of the malecot 105. At the same time, the malecot holding tube 376 is moved distally such that the claw extends out of the proximal end of the malecot holding tube 376 allowing the claw to open and release the malecot 105.

Figure 47:
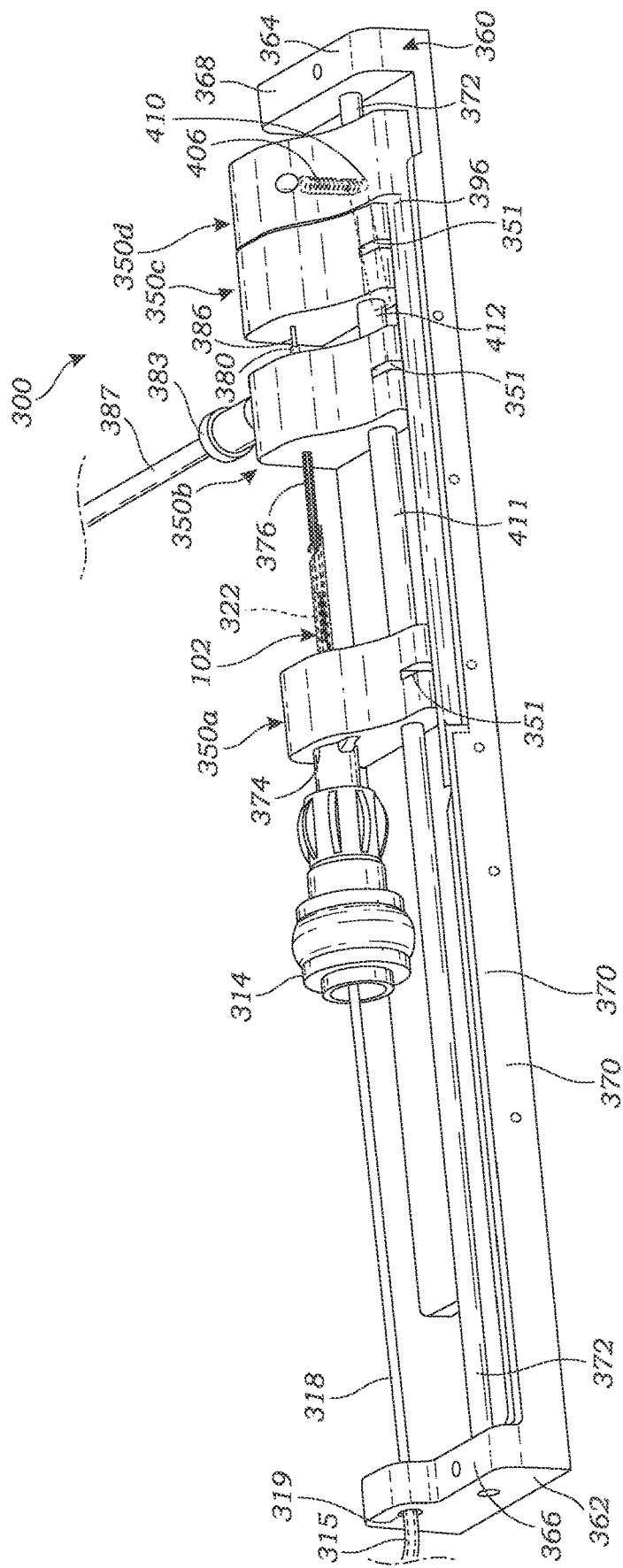
FIG. 47 is a front, perspective view of the shunt loader and shunt assembly of FIGS. 28 and 33 illustrating Step 5 of a method of using the shunt loading system of FIG. 28, according to one embodiment of the disclosed inventions.
Figure 48:
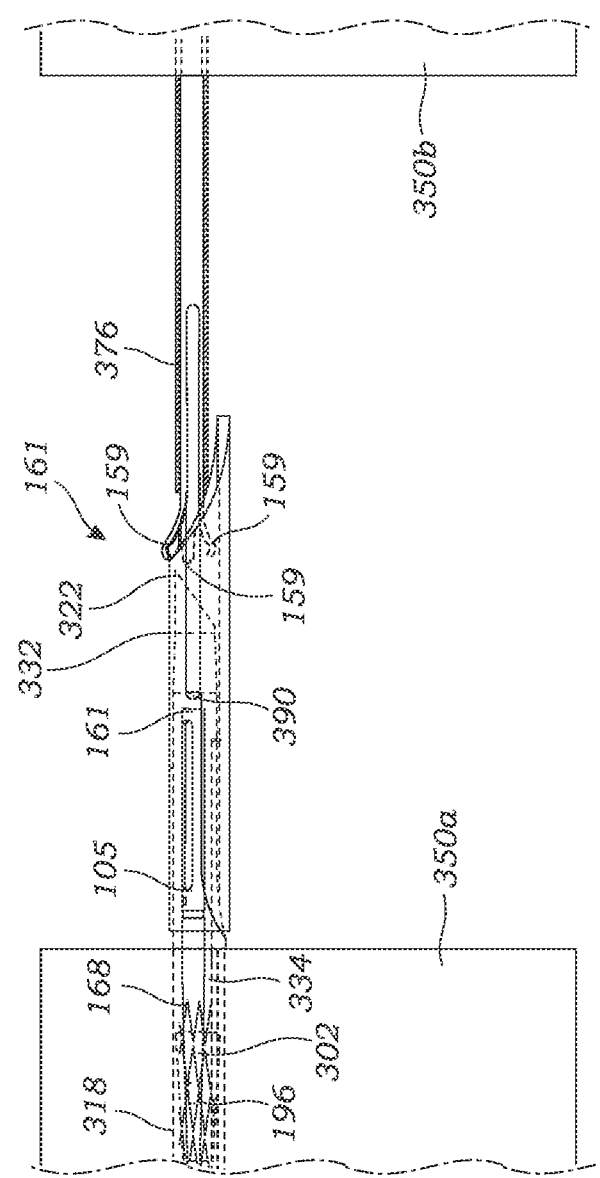
FIG. 48 is a side, partial sectional view depicting the shunt assembly delivery catheter of FIGS. 28 and 33 illustrating Step 5 of a method of using the shunt loading system of FIG. 28, according to one embodiment of the disclosed inventions.

Referring to FIGS. 47 and 48, at Step 5, the claw guide boss retainer 398e is removed, thereby allowing concurrent longitudinal movement of the delivery catheter guide boss 350a, the malecot holding tube guide boss 350b and the claw guide boss 350c. The concurrent movement of Step 5 is caused by moving the delivery catheter guide boss 350a distally, while the first bump tube 411 pushes the malecot holding tube guide boss 350b distally and the second bump tube 412 pushes the claw guide boss 350c. As shown in the table of FIG. 49, at Step 5, the delivery catheter guide boss 350a, the malecot holding tube guide boss 350b and the claw guide boss 350c move 0.5 inches distally. The delivery catheter guide boss 350a and attached delivery catheter 302, the malecot holding tube guide boss 350b and attached malecot holding tube 376, and the claw guide boss 350c and attached claw assembly 356 are moved distally until the distal face of the claw guide boss 350c contacts the proximal face of the chase pin guide boss 350d which stops the distal movement.

As depicted in FIG. 48, the delivery catheter 302 (including the needle 322, needle guard 332 and catheter 318) is moved distally such that the remainder of the malecot 105 is captured in the needle 322 of the delivery catheter 302, and at the same time the malecot cover tube 376 and claw assembly 356 are moved distally out of the way of the delivery catheter 302. The chase pin 390 remains stationary such that the distal end 392 of the chase pin 390 ensures that the malecot 105 does not move distally while the delivery catheter 302 is moved over the malecot 105.

At the end of Step 5, the shunt assembly 102 and shroud 168 are sheathed within the delivery catheter 302, and the shunt body 103 is in a stretched and necked condition. In addition, the delivery catheter 302, shunt assembly 102 and shroud 168 have been flushed with a flushing fluid. The delivery catheter 302 may now be released from the compression fitting 314 by loosening the compression fitting 314. The shroud tether 166 is released from the torquer holder 310 and/or the torquer 308. The delivery catheter 302 with the shunt assembly 102 and shroud 168 loaded in the delivery catheter 302 is removed from the shunt loader 300.

The delivery catheter 302 with the shunt assembly 102 and shroud 168 loaded in the delivery catheter 302 is now fully prepared to be used to insert the shunt assembly 102 into the vascular system of a patient, and implant the shunt 103 in the patient. Exemplary devices and methods for using the delivery catheter 302 and shunt assembly 102 to implant the shunt body 103 are disclosed in the above-incorporated patent and application publications.

Figure 50:
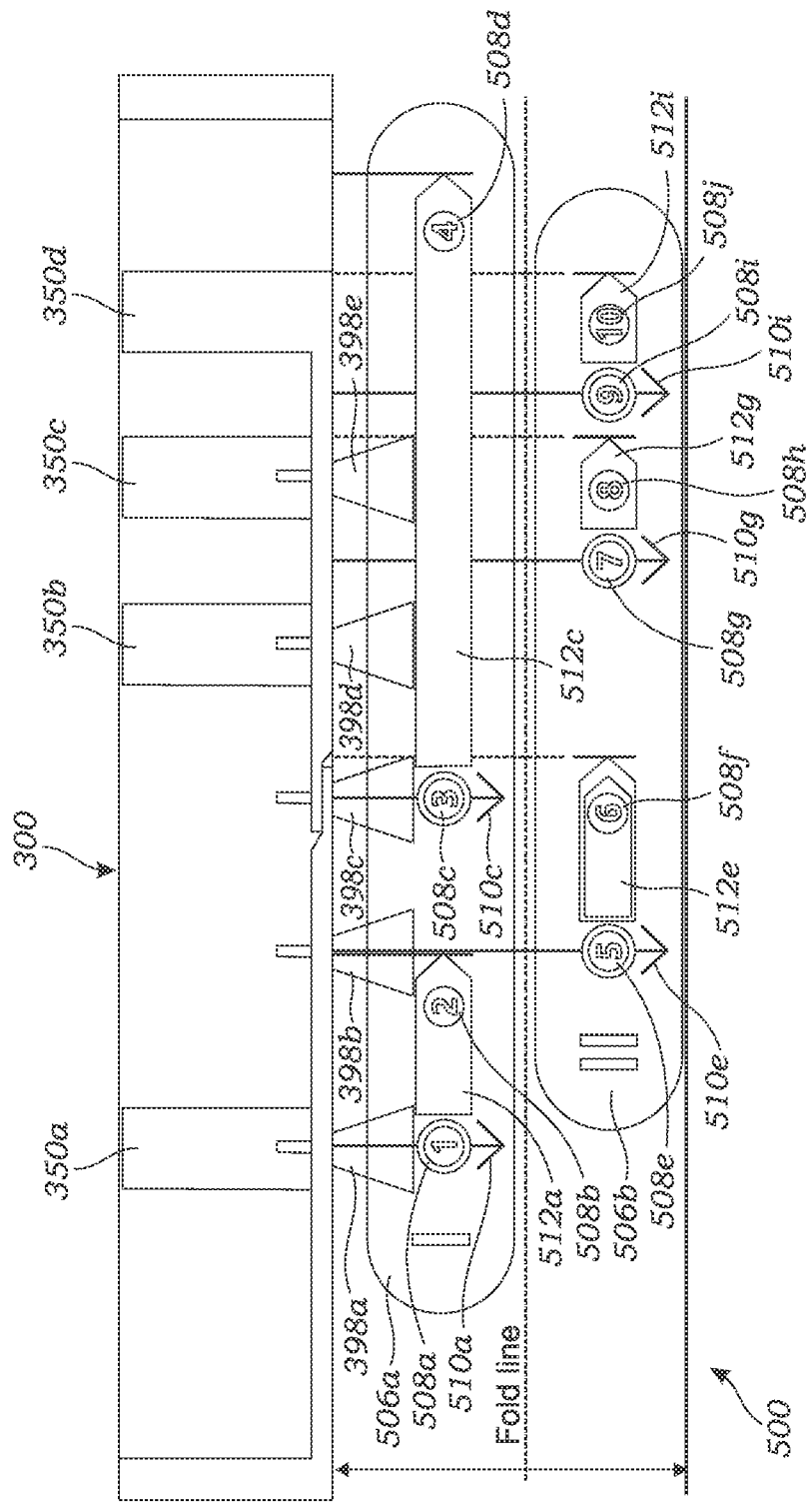
FIG. 50 is a plan view of an instructional graphic adjacent a schematic view of the shunt loading system of FIG. 28, according to one embodiment of the disclosed inventions.

Turning to FIG. 50, one embodiment of an instructional graphic 500 is shown. The instructional graphic 500 provides user instructions for operating the endovascular shunt loader 300 in loading the endovascular shunt assembly 102 onto the delivery catheter 302, as described herein and illustrated in the drawings. The instructional graphic 500 includes a substrate 502 upon which is printed graphic instructions 504 for operating the shunt loader 300. The substrate 502 may be a printed card, a portion of the packaging for the shunt loader 300 and shut assembly 102, a decal, a film or other suitable substrate upon which the graphic instructions 504 are printed.

The graphic instructions 504 include a plurality of markers, arrows, numbers and indicators to instruct a user in operating the shunt loader 300. The graphic instructions 504 include two adjacent backgrounds 506a and 506b, within which the graphic instructions are printed. The backgrounds 506a and 506b are elongated printed areas which are parallel to the shunt loader 300. The first background 506a is numbered with a roman numeral "I" and the second background 506b is numbered with a roman numeral "II", indicating that the instructions on the first background 506a are performed before the instructions on the second background 506b.

On the first background 506a is a first marker 508a numbered as number "1" indicating that this corresponds to a first step of operating the shunt loader 300. The first marker 508a is colored circle (i.e., a different color than the first background 506a) with the number "1" within the colored circle. It is understood that the first marker 508a may be any suitable shape. A first directional arrow 510a is positioned at the first marker 508a and points laterally outward away from the shunt loader 300. The first marker 508a and first directional arrow 510a are laterally aligned with the delivery catheter guide boss 350a and the delivery catheter boss retainer 398a. The first marker 508a and first directional arrow 510a indicate that the first step of operating the shunt loader 300 is remove the delivery catheter boss retainer 398a by pulling the delivery catheter boss retainer 398a in the direction of the directional arrow 510a. The first marker 508a and first directional arrow 510a may have the same first color, which is orange in the illustrated example of FIG. 50. It is understood that the first color may be any suitable color, which differs from the other colors of the instructional graphic 500.

Adjacent to the first marker 508a and first directional arrow 510a is a Step 1 motion indicator 512a. The delivery catheter guide boss motion indicator 512b is an arrow pointing to the right from the first marker 508a indicating a direction of motion for moving the corresponding delivery catheter guide boss 350a. A first end of the Step 1 motion indicator 512a is laterally aligned with the delivery catheter guide boss 350a, and a second end (pointed end) is laterally aligned with the ending position of the delivery catheter guide boss 350a after it is moved during Step 1 of the method of using the shunt loader 300. The Step 1 motion indicator 512a is also the first color, orange. The Step 1 motion indicator 512a has a second marker 508b numbered as number "2" on or within the boss motion indicator 512a indicating that this corresponds to a second step of operating the shunt loader 300 (the first and second steps on the instructional graphic 500 correspond to "Step 1" of operating the shunt loader, as described above).

The first background 506a has a third marker 508c numbered as number "3" indicating that this corresponds to a third step of operating the shunt loader 300. The third marker 508c is the same as the first marker 508a, except that it is a second color different from the first color, in this example, yellow. A second directional arrow 510c is positioned at the third marker 508c and points laterally outward away from the shunt loader 300, and is also the second color. The third marker 508c and second directional arrow 510c are laterally aligned with the connecting arm retainer 398c. The third marker 508c and second directional arrow 510c indicate that the third step of operating the shunt loader 300 is to remove the connecting arm retainer 398c by pulling the connecting arm retainer 398c in the direction of the directional arrow 510c. The third marker 508c and third directional arrow 510c may have the same second color, which is yellow in the illustrated example of FIG. 50. It is understood that the second color may be any suitable color, which differs from the other colors of the instructional graphic 500.

Adjacent to the third marker 508c and second directional arrow 510c is a Step 2 motion indicator 512c. The Step 2 motion indicator 512c is an arrow pointing to the right from the third marker 508c indicating a direction of motion for moving the connecting arm 396. A first end of the Step 2 motion indicator 512c is laterally aligned with the connecting arm retainer 398c, and a second end (pointed end) is laterally aligned with the ending position of the chase pin guide boss 350d after the connecting arm 396, malecot holding tube guide boss 350b, claw guide boss 350c, and chase pin guide boss 350d are all moved during Step 2 of the method of using the shunt loader 300. The Step 2 motion indicator 512c is also the second color, yellow. The Step 2 motion indicator 512c has a fourth marker 508d numbered as number "4" on or within the Step 2 motion indicator 512c indicating that this corresponds to a fourth step of operating the shunt loader 300 (the third and fourth steps on the instructional graphic 500 correspond to "Step 2" of the method of operating the shunt loader, as described above).

On the second background 506b is a fifth marker 508e numbered as number "5" indicating that this corresponds to a fifth step of operating the shunt loader 300. The fifth marker 508e is the same as the first marker 508a, except that it is a third color different from the first and second colors, in this example, green. A third directional arrow 510e is positioned at the fifth marker 508e and points laterally outward away from the shunt loader 300, and is also the third color. The fifth marker 508e and third directional arrow 510e are laterally aligned with the stop retainer 398b and the position of the delivery catheter guide boss 350a after it is moved during the second step (part of Step 1 of the method of using the shunt loader 300). The fifth marker 508e and third directional arrow 510e indicate that the fifth step of operating the shunt loader 300 is to remove the stop retainer 398b by pulling the stop retainer 398c in the direction of the directional arrow 510e. The fifth marker 508e and third directional arrow 510e may have the same third color, which is green in the illustrated example of FIG. 50. It is understood that the third color may be any suitable color, which differs from the other colors of the instructional graphic 500.

Adjacent to the fifth marker 508e and third directional arrow 510e is a Step 3 motion indicator 512e. The Step 3 motion indicator 512e is two arrows pointing to the right from the fifth marker 508e indicating a direction of motion for moving the catheter guide boss 350a, after the stop retainer 398b is removed. The Step 3 motion indicator 512e has a first arrow having the third color, green, and a second arrow overlying the first arrow having the first color, orange. The color of the first arrow indicates that the Step 3 motion indicator 512e is related to the fifth marker 508e, and the color of second arrow matches the color of the guide boss motion indicator 512a to indicate that the Step 3 motion indicator 512e corresponds to the motion of the catheter guide boss 350a. A first end of the Step 3 motion indicator 512e is laterally aligned with the stop retainer 398b and catheter guide boss 350a after it is moved during Step 1, and a second end (pointed end) is laterally aligned with the ending position of the catheter guide boss 350a after it is moved during Step 3 of the method of using the shunt loader 300. The Step 3 motion indicator 512e has a sixth marker 508f numbered as number "6" on or within the Step 3 motion indicator 512c indicating that this corresponds to a sixth step of operating the shunt loader 300 (the fifth and sixth steps on the instructional graphic 500 correspond to "Step 3" of the method of operating the shunt loader, as described above).

On the second background 506b is a seventh marker 508g numbered as number "7" indicating that this corresponds to a seventh step of operating the shunt loader 300. The seventh marker 508g is the same as the first marker 508a, except that it is a fourth color different from the first, second and third colors, in this example, blue. A fourth directional arrow 510g is positioned at the seventh marker 508g and points laterally outward away from the shunt loader 300, and is also the fourth color. The seventh marker 508g and fourth directional arrow 510g are laterally aligned with the position of the malecot holding tube guide boss 350b and the malecot holding tube boss retainer 398d after they are moved during the Step 2. The seventh marker 508g and fourth directional arrow 510g indicate that the seventh step of operating the shunt loader 300 is to remove the malecot holding tube boss retainer 398d by pulling the malecot holding tube boss retainer 398d in the direction of the directional arrow 510g. The seventh marker 508g and fourth directional arrow 510c may have the same fourth color, which is blue in the illustrated example of FIG. 50. It is understood that the fourth color may be any suitable color, which differs from the other colors of the instructional graphic 500.

Adjacent to the seventh marker 508g and fourth directional arrow 510g is Step 4 motion indicator 512g. The Step 4 motion indicator 512g is an arrow pointing to the right from the seventh marker 508g indicating a direction of motion for moving the malecot holding tube guide boss 350b, after the malecot holding tube boss retainer 398d is removed. The Step 4 motion indicator 512g is an arrow pointing to the right from the seventh marker 508g indicating a direction of motion for moving the malecot holding tube guide boss 350b. A first end of the Step 4 motion indicator 512g is laterally aligned with the location of the malecot holding tube guide boss 350b after it has been moved during Step 3, and a second end (pointed end) is laterally aligned with the ending position of the malecot holding tube boss 350b after being moved during the eighth step of operating the shunt loader 300 (part of Step 4 of the method of using the shunt loader 300). The Step 4 motion indicator 512g is also the fourth color, blue. The Step 4 motion indicator 512g has an eighth marker 508h numbered as number "8" on or within the malecot holding tube guide boss motion indicator 512g indicating that this corresponds to the eighth step of operating the shunt loader 300 (the seventh and eighth steps on the instructional graphic 500 correspond to "Step 4" of the method of operating the shunt loader, as described above).

On the second background 506b is a ninth marker 508i numbered as number "9" indicating that this corresponds to a ninth step of operating the shunt loader 300. The ninth marker 508i is the same as the first marker 508a, except that it is a fifth color different from the first, second, third and fourth colors, in this example, purple. A fifth directional arrow 510*i* is positioned at the ninth marker 508*i* and points laterally outward away from the shunt loader 300, and is also the fifth color. The ninth marker 508*i* and fifth directional arrow 510*i* are laterally aligned with the position of the claw guide boss 350*c* and claw boss retainer 398*e* after they are moved during Step 4 of the method of operating the shunt loader 300. The ninth marker 508*i* and fifth directional arrow 510*i* indicate that the ninth step of operating the shunt loader 300 is to remove the claw boss retainer 398*e* by pulling the claw boss retainer 398*e* in the direction of the directional arrow 510*i*. The ninth marker 508*i* and fifth directional arrow 510*i* may have the same fifth color, which is purple in the illustrated example of FIG. 50. It is understood that the fifth color may be any suitable color, which differs from the other colors of the instructional graphic 500.

Adjacent to the ninth marker 508*i* and fifth directional arrow 510*i* is a Step 5 motion indicator 512*i*. The Step 5 motion indicator 512*i* is an arrow pointing to the right from the ninth marker 508*i* indicating a direction of motion for moving the malecot holding tube guide boss 350*b* and claw guide boss 350*c*, after the claw guide boss retainer 398*e* is removed. The Step 5 motion indicator 512*i* is an arrow pointing to the right from the ninth marker 508*i* indicating a direction of motion for moving the delivery catheter guide boss 350*a*, malecot holding tube guide boss 350*b* and claw guide boss 350*c* during Step 5. A first end of the Step 5 motion indicator 512*i* is laterally aligned with the location of the claw guide boss 350*c* and claw guide boss retainer 398*e* after being moved during Step 3, and a second end (pointed end) is laterally aligned with the ending position of the claw guide boss 350*c* after the delivery catheter guide boss 350*a*, malecot holding tube guide boss 350*b*, and claw guide boss 350*c* are moved during Step 5 of the method of using the shunt loader 300. The Step 5 motion indicator 512*i* is also the fifth color, purple. The Step 5 motion indicator 512*i* has a tenth marker 508*j* numbered as number "10" on or within the Step 5 motion indicator 512*i* indicating that this corresponds to a tenth step of operating the shunt loader 300 (the ninth and tenth steps on the instructional graphic 500 correspond to "Step 5" of the method operating the shunt loader, as described above).

Figure 51:
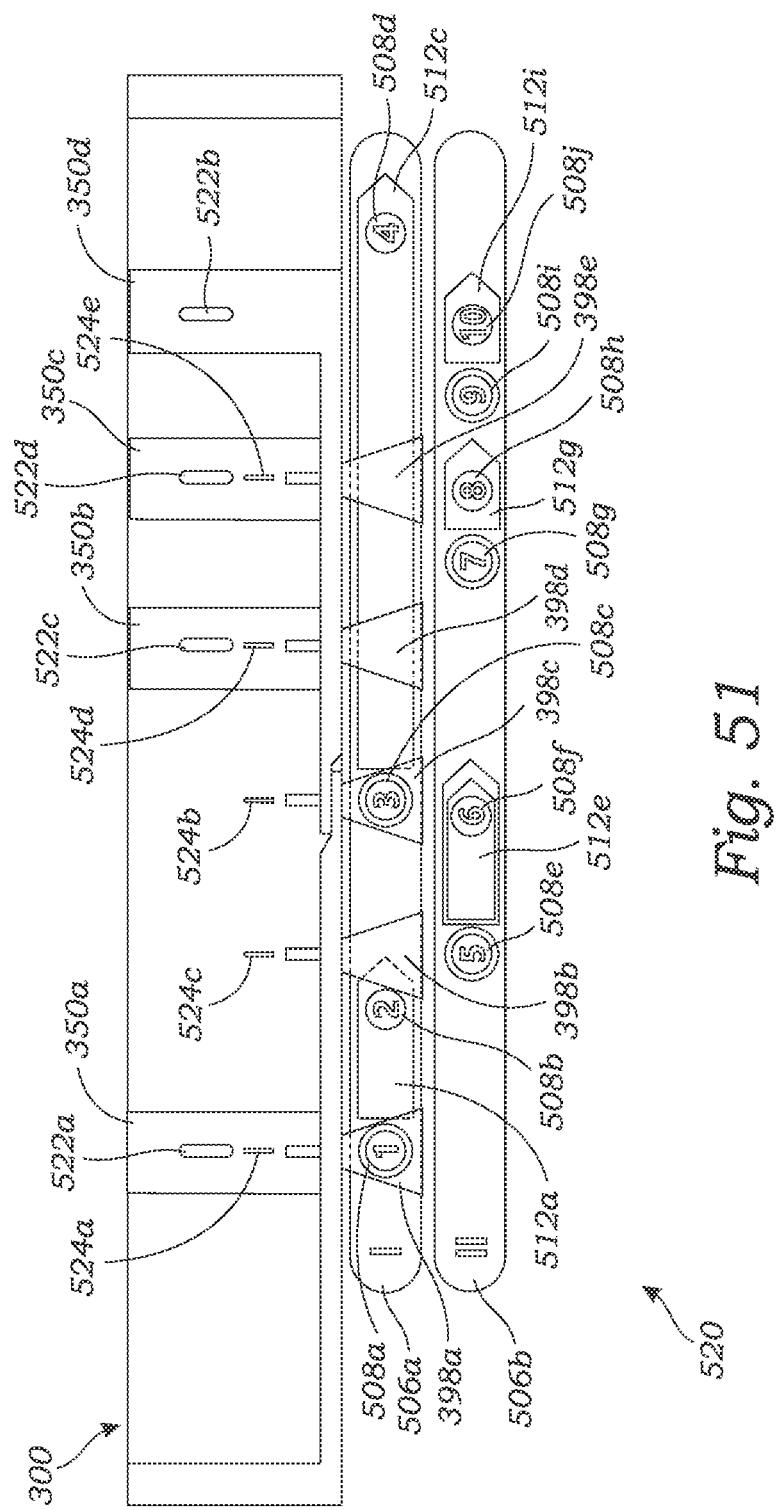
FIG. 51 is a plan view of another instructional graphic adjacent a schematic view of the shunt loading system of FIG. 28, according to one embodiment of the disclosed inventions.

Referring to FIG. 51, another embodiment of an instructional graphic 520 having user instructions for operating the endovascular shunt loader 300 is shown. The instructional graphic 520 is similar to the instruction graphics 510, except that instead of directional arrows 510, the instructional graphic 520 includes icons printed on the guide bosses 350 and base 360 of the shunt loader 300. Also, the first and second backgrounds 506*a*, 506*b* are narrower, such that they occupy less space. Thus, for Step 1, a first guide boss icon 522*a* is disposed on the delivery catheter guide boss 350*a*, and a first retainer icon 524*a* is disposed on the delivery catheter guide boss 350*a*. The first guide boss icon 522*a* and first retainer icon 524*a* are the same first color, orange, to match the first color of the first marker 508*a* and Step 1 motion indicator 512*a*, indicating that they correspond to each other.

A second retainer icon 524*b* is disposed on the base 360 of the shunt loader 300 laterally aligned with the connecting arm retainer 398*c*. In addition, a second guide boss icon 522*b* is disposed on the chase pin guide boss 350*d*. The second retainer icon 524*b* and second guide boss icon 522*b* are the same second color (yellow) as the third marker 508*c* and Step 2 motion indicator 512*c*, indicating that they correspond to each other.

A third retainer icon 524*c* is disposed on the base 360 laterally aligned with the stop retainer and the position of the catheter guide boss 350*a* after being moved during Step 1. The third retainer icon 524*c* is the same third color (green) as the fifth marker 508*e* and the first arrow of the Step 3 motion indicator 512*e* indicating that they correspond to each other. Also, the first guide boss icon 524*a* matches the color of the second arrow of the Step 3 motion indicator indicating that they correspond to each other.

A third guide boss icon 522*c* is disposed on the malecot holding tube guide boss 350*b*, and a fourth retainer icon 524*d* is disposed on the malecot holding tube guide boss 350*b*. The fourth retainer icon 524*d* and third guide boss icon 522*c* are the same fourth color (blue) as the seventh marker 508*g* and Step 4 motion indicator 512*g*, indicating that they correspond to each other.

A fourth guide boss icon 522*d* is disposed on the claw guide boss 350*c*, and a fifth retainer icon 524*e* is disposed on the claw guide boss 35*c*. The fifth retainer icon 524*e* and fourth guide boss icon 522*d* are the same fifth color (purple) as the eighth marker 508*g* and Step 5 motion indicator 512*i*, indicating that they correspond to each other.

Figure 52:
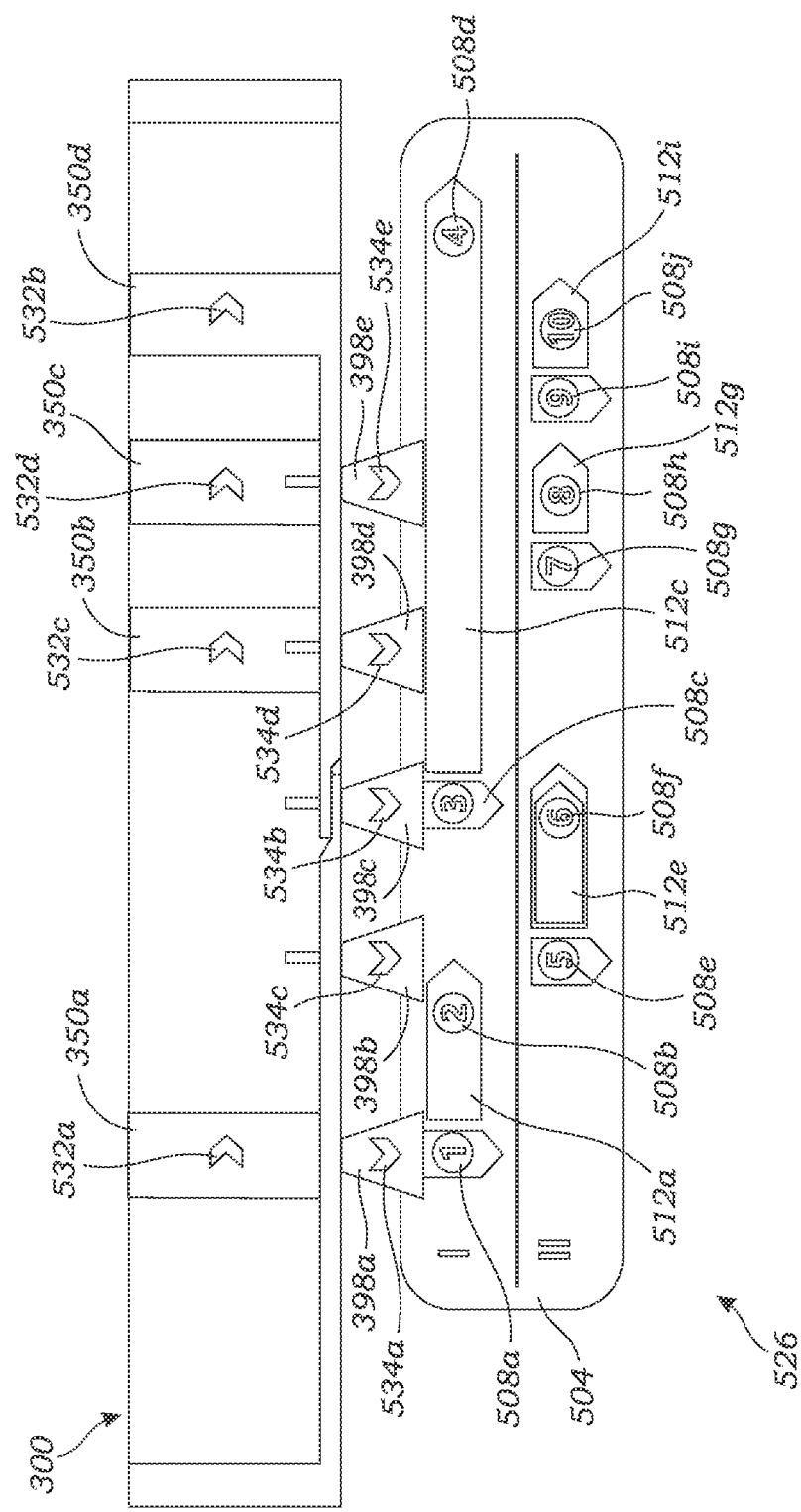
FIG. 52 is a plan view of another instructional graphic adjacent a schematic view of the shunt loading system of FIG. 28, according to one embodiment of the disclosed inventions.

Referring to FIG. 52, still another embodiment of an instructional graphic 526 having user instructions for operating the endovascular shunt loader 300 is shown. The instructional graphic 520 is similar to the instruction graphics 500 and 520, except that instead of directional arrows 510, the instructional graphic 520 includes icons printed on the guide bosses 350 and the retainers 398. Also, the markers 508*a*, 508*c*, 508*e*, 508*g* and 508*i* are arrows instead of circles, with the arrows pointing laterally outward from the shunt loader 300 in the direction of removing the respective retainers 398.

Thus, for Step 1, a first guide boss icon 532*a* is disposed on the delivery catheter guide boss 350*a*, and a first retainer icon 534*a* is disposed on the delivery catheter guide boss retainer 398*a*. The first guide boss icon 532*a* has a chevron shape pointing in the direction of motion of the delivery catheter guide boss during Step 1. The first retainer icon 534*a* is also a chevron pointing laterally outward from the shunt loader 300 in the direction of removing the delivery catheter guide boss retainer 398*a*. The first guide boss icon 532*a* and first retainer icon 534*a* are the same first color, orange, to match the first color of the first marker 508*a* and Step 1 motion indicator 512*a*, indicating that they correspond to each other.

Corresponding to Step 2, a second retainer icon 534*b* is disposed on the connecting arm retainer 398*c*, and a second guide boss icon 532*b* is disposed on the chase pin guide boss 350*d*. The second retainer icon 534*b* is a chevron pointing laterally outward from the shunt loader 300 in the direction of removing the connecting arm retainer 398*c*. The second guide boss icon 532*b* is a chevron pointing in the direction of motion of the connecting arm 396, malecot holding tube guide boss 350*b*, claw guide boss 350*xc* and chase pin guide boss 350*d* during Step 2. The second retainer icon 534*b* and second guide boss icon 532*b* are the same second color (yellow) as the third marker 508*c* and Step 2 motion indicator 512*c*, indicating that they correspond to each other.

For Step 3, a third retainer icon 534*c* is disposed on the stop retainer 598*b*. The third retainer icon 534*b* is a chevron pointing laterally outward from the shunt loader 300 in the direction of removing the stop retainer 398*b*. The third retainer icon 534*c* is the same third color (green) as the fifth marker 508*e* and the first arrow of the Step 3 motion indicator 512*e* indicating that they correspond to each other. Also, the first guide boss icon 534*a* matches the color of the second arrow of the Step 3 motion indicator indicating that they correspond to each other.

For Step 4, a third guide boss icon 532c is disposed on the malecot holding tube guide boss 350b, and a fourth retainer icon 534d is disposed on the malecot holding tube guide boss retainer 398d. The fourth retainer icon 534d is a chevron pointing laterally outward from the shunt loader 300 in the direction of removing the malecot holding tube guide boss retainer 398d. The third guide boss icon 532c is a chevron pointing in the direction of motion of the malecot holding tube guide boss 350b during Step 4. The fourth retainer icon 534d and third guide boss icon 532c are the same fourth color (blue) as the seventh marker 508g and Step 4 motion indicator 512g, indicating that they correspond to each other.

For Step 5, a fourth guide boss icon 532d is disposed on the claw guide boss 350c, and a fifth retainer icon 534e is disposed on the claw guide boss retainer 398e. The fifth retainer icon 534e is a chevron pointing laterally outward from the shunt loader 300 in the direction of removing the claw guide boss retainer 398e. The fourth guide boss icon 532d is a chevron pointing in the direction of motion of the malecot holding tube guide boss 350b and claw guide boss 350c during Step 5. The fifth retainer icon 534e and fourth guide boss icon 532d are the same fifth color (purple) as the eighth marker 508g and Step 5 motion indicator 512i, indicating that they correspond to each other.

Figure 53A:
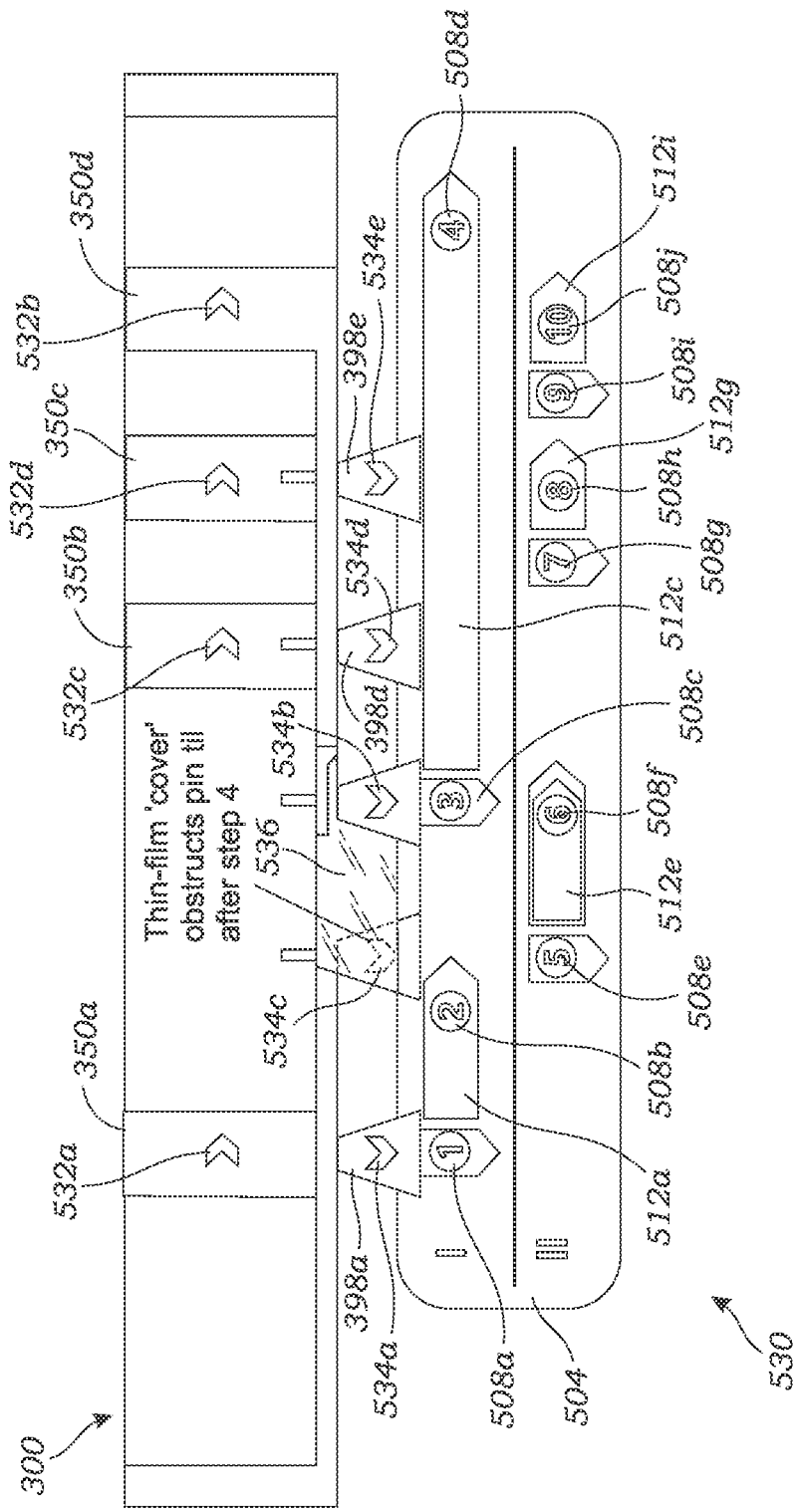
FIGS. 53A and 53B are plan views of another instructional graphic adjacent a schematic view of the shunt loading system of FIG. 28, according to one embodiment of the disclosed inventions.
Figure 53B:
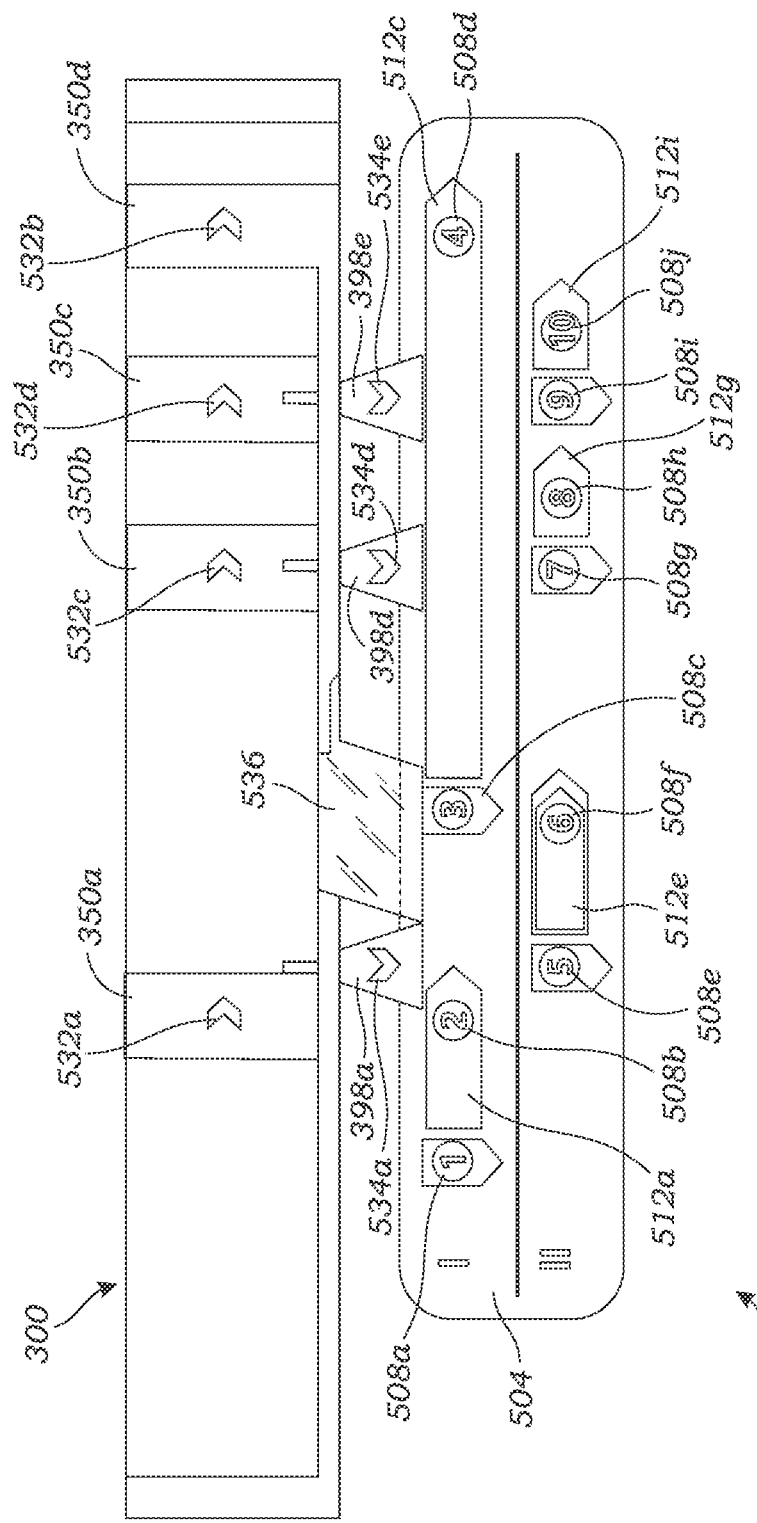

Turning to FIGS. 53A and 53B, another embodiment of an instructional graphic 530 having user instructions for operating the endovascular shunt loader 300 is shown. The instructional graphic 530 is similar to the instruction graphic 520, except that it also includes a retainer cover 536. The stop retainer cover 536 is a thin film which is attached to the connecting arm 396 and covers the stop retainer 398b until the connecting arm 396 is moved during the fourth step, as shown in FIG. 53B. This prevents a user from incorrectly removing the stop retainer 398b before performing the third and fourth steps (i.e., removing the connecting arm retainer 398c and moving the connecting arm 396, malecot holding tube guide boss 350b, claw guide boss 350c and chase pin guide boss 350d during Step 2). This is a potential problem because the stop retainer 398b is the first retainer 398 to the right of the delivery catheter guide boss retainer 398a, and user may assume that the next step is to remove the stop retainer 398b. The stop retainer cover 536 prevents this error.

Figure 54:
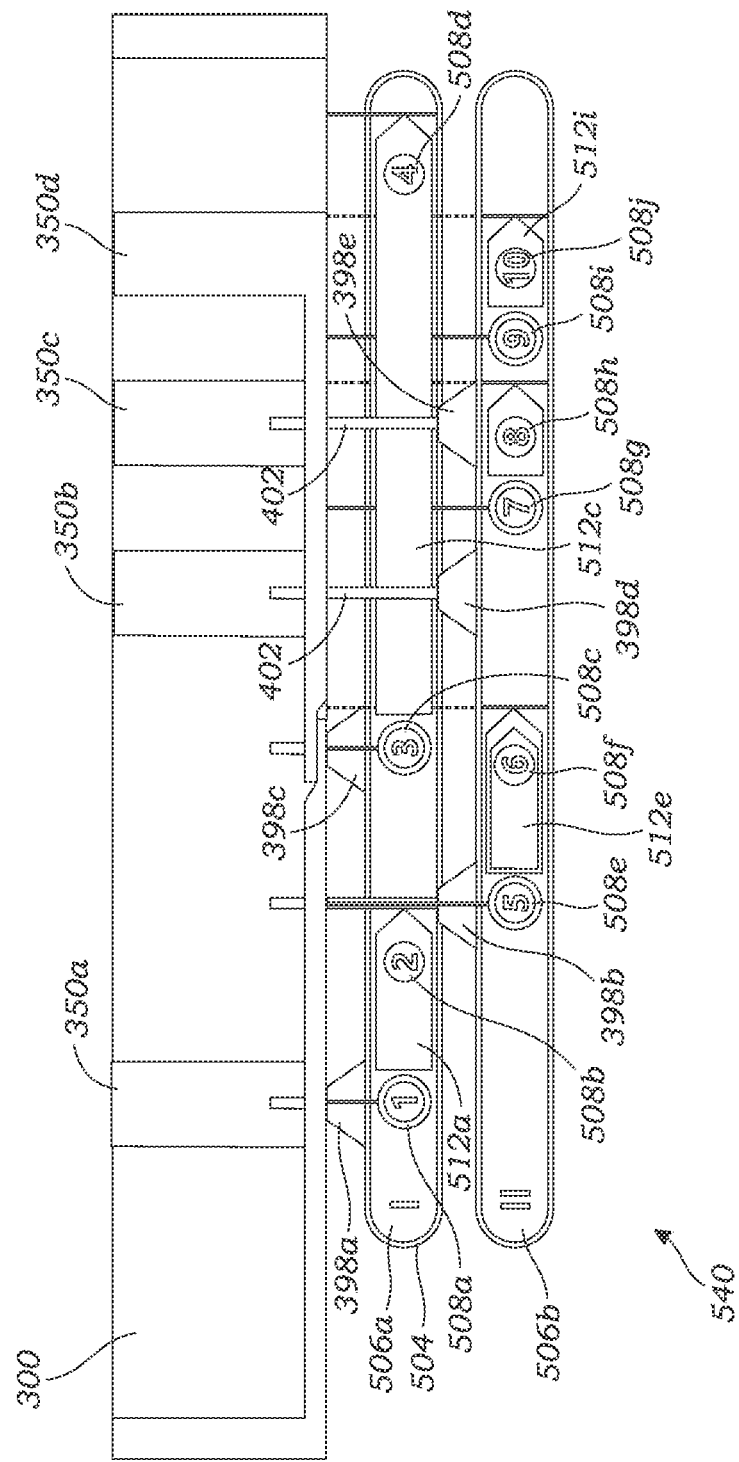
FIG. 54 is a plan view of another instructional graphic adjacent a schematic view of the shunt loading system of FIG. 28, according to one embodiment of the disclosed inventions.

Referring to FIG. 54, another embodiment of an instructional graphic 540 having user instructions for operating the endovascular shunt loader 300 is shown. The instructional graphic 540 is similar to the instruction graphic 520, except that instead of using icons, the entire guide bosses 350 and retainers 398 are colored with the respective color to match the corresponding markers 508 and motion indicators 512, and the retainers 398 for steps on the second background have extended pins 402 so the that pull tab 400 is located proximate the respective markers 508.

For Step 1, the delivery catheter guide boss 350a and the delivery catheter guide boss retainer 398a (the pin 402 and the pull tab 400) are both the first color, orange indicating that they correspond to the first marker 508a and the Step 1 motion indicator 512a, which are also the first color. The delivery catheter guide boss 350a and the delivery catheter guide boss retainer 398a may be painted the first color, or pigmented the first color (e.g., if they are molded plastic parts), or colored in another suitable manner. All of the other guide bosses 350 and retainers 398 may be colored in the same manner.

For Step 2, the connecting arm 396, connecting arm retainer 398c, and chase pin guide boss 350d are the second color, yellow, indicating that they correspond to the third marker 508c and the Step 2 motion indicator 512c, which are also the second color.

For Step 3, the stop retainer 398b is the third color, green, indicating that it corresponds to the fifth marker 508e and the first arrow of the Step 3 motion indicator 512e, which are also the third color. Also, the first color of the delivery catheter guide boss 350a matches the first color of the second arrow of the Step 3 motion indicator 512e. In addition, the stop retainer 398b has a long pin 402 such that the pull tab 400 for the stop retainer 398b is adjacent the fifth marker 508e and between the first and second backgrounds 506a, 506b.

For Step 4, the malecot holding tube guide boss 350b and malecot holding tube guide boss retainer 398d are the fourth color, blue, indicating that they correspond to the seventh marker 508g and the Step 4 motion indicator 512g, which are also the fourth color. Also, the malecot holding tube guide boss retainer 398d has a long pin 402 such that the pull tab 400 for the malecot holding tube guide boss retainer 398d is adjacent the seventh marker 508g and between the first and second backgrounds 506a, 506b.

For Step 5, the claw guide boss 350c and the claw guide boss retainer 398e are the fifth color, purple, indicating that they correspond to the ninth marker 508i and the Step 5 motion indicator 512i, which are also the fifth color. Also, the claw guide boss retainer 398e has a long pin 402 such that the pull tab 400 for the claw guide boss retainer 398d is adjacent the ninth marker 508i and between the first and second backgrounds 506a, 506b.

Figure 55:
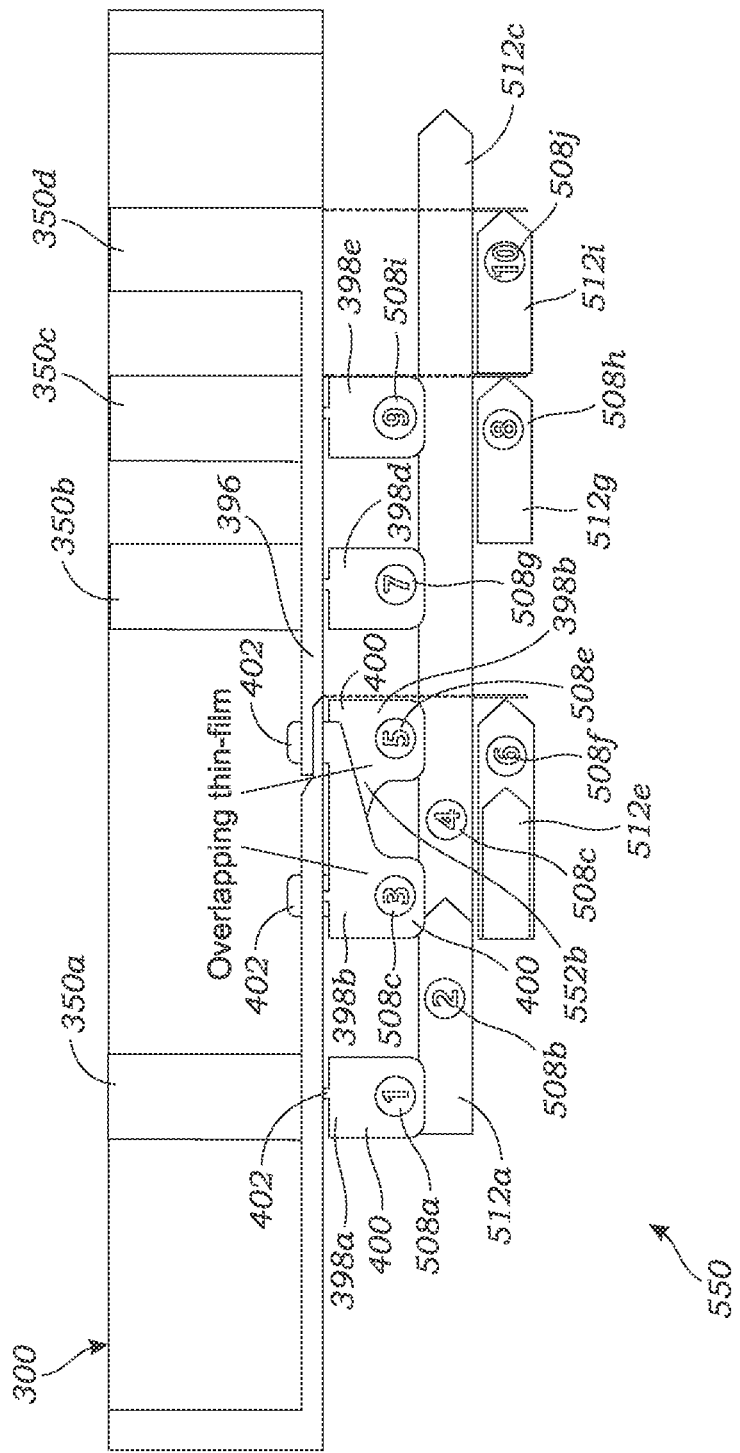
FIG. 55 is a plan view of another instructional graphic adjacent a schematic view of the shunt loading system of FIG. 28, according to one embodiment of the disclosed inventions.

FIG. 55 illustrates another embodiment of an instructional graphic 550 having user instructions for operating the endovascular shunt loader 300 is shown. The instructional graphic 550 also entails some modifications to the retainers 398. The instructional graphic 550 is similar to the instructional graphic 540, in that the entire guide bosses 350 and retainers 398 are colored with the respective color to match the corresponding markers 508 and motion indicators 512. Also, the markers 508 are disposed on the retainers 398.

For Step 1, the delivery catheter guide boss 350a and the delivery catheter guide boss retainer 398a are both the first color, orange indicating that they correspond to the first marker 508a and the Step 1 motion indicator 512a, which is also the first color. As shown in FIG. 55, the delivery catheter guide boss retainer 398a (and each of the other retainers 398) is a substantially flat tab 400 and a pin 402. The first marker 508a is disposed on the flat tab 400. The guide bosses 350 and retainers 398 for the embodiment of FIG. 55 may be painted the respective color, or pigmented the first color (e.g., if they are molded plastic parts), or colored using decals, or colored in another suitable manner.

For Step 2, the connecting arm 396, connecting arm retainer 398c, and chase pin guide boss 350d are the second color, yellow, indicating that they correspond to the third marker 508c and the Step 2 motion indicator 512c, which are also the second color. The connecting arm retainer 398c has an extension arm 552a extending proximally from the pin 402 to the tab 400 such that the tab 400 and third marker 508c are located proximally of the tab 400 and fifth marker 508e of the stop retainer 398b. In the illustrated example, the tab 400 and third marker 508c are aligned with the pin 402 of the stop retainer 398b. In this way, the respective pull tabs 400 and markers 508 are in arranged from left to right in the same order as their respective steps.

For Step 3, the stop retainer 398*b* is the third color, green, indicating that it corresponds to the fifth marker 508*e* and the first arrow of the Step 3 motion indicator 512*e*, which are also the third color. Also, the first color of the delivery catheter guide boss 350*a* matches the first color of the second arrow of the Step 3 motion indicator 512*e*. The stop retainer 398*b* has an extension arm 552*b* extending distally from the pin 402 to the tab 400 such that the tab 400 and fifth marker 508*e* are located distally of the tab 400 and third marker 508*c* of the connecting arm retainer 398*c*.

For Step 4, the malecot holding tube guide boss 350*b* and malecot holding tube guide boss retainer 398*d* are the fourth color, blue, indicating that they correspond to the seventh marker 508*g* and the Step 4 motion indicator 512*g*, which are also the fourth color. The seventh marker 508*g* is disposed on the flat tab 400 of the malecot holding tube guide boss retainer 398*d*.

For Step 5, the claw guide boss 350*c* and the claw guide boss retainer 398*e* are the fifth color, purple, indicating that they correspond to the ninth marker 508*i* and the Step 5 motion indicator 512*i*, which are also the fifth color. The ninth marker 508*i* is disposed on the flat tab 400 of the claw guide boss retainer 398*e*.

FIGS. 56A and 56B illustrate yet another embodiment of an instructional graphic 560 having user instructions for operating the endovascular shunt loader 300 is shown. The instructional graphic 560 is substantially the same as the instructional graphic 530, except that the markers 508 and motion indicators 512 are disposed on a single background 506, without a separation, and the markers 508 are numbered to match "Step 1", "Step 2", "Step 3", "Step 4" and "Step 5", as described above for the method of using the shunt loader 300. The instructional graphic 560 may be used with the same guide boss icons 532 and retainer icons 534, as in the instructional graphic 530.

FIGS. 57A and 57B illustrate yet another embodiment of an instructional graphic 570 having user instructions for operating the endovascular shunt loader 300 is shown. The instructional graphic 570 is substantially the same as the instruction graphic 560, except that the markers 508 connect to the motion indicators 512 in an integral arrow with a 90 degree angle between the respective marker 508 and motion indicator 512.

FIGS. 58A and 58B illustrate another embodiment of an instructional graphic 580 having user instructions for operating the endovascular shunt loader 300 is shown. The instructional graphic 580 is substantially the same as the instruction graphic 570, except that it includes a guide line 572 between the markers 508 and motion indicators 512 showing the order of the steps.

FIGS. 59A and 59B illustrate another embodiment of a shunt loader 590 which is substantially the same as the shunt loader 300, except that it has alternative design for the retainers 592 which incorporates instructional graphics/colors. Each of the retainers 592 includes a pin 402 connected to a pull tab 400 which has a long flat panel 594 extending longitudinally from the pull tab 400. Each of the flat panels 594 have inclines so that the respective flat panels stack onto each other in the order of the steps in which each of the retainers 592 are removed in the method of using the shunt loader 592.

Accordingly, for Step 1, the delivery catheter guide boss retainer 592*a* is the first color, orange. The flat panel 594*a* of the delivery catheter guide boss retainer 592*a* extends distally from the pull tab 400 such that it is on top of the stack of retainers 592. The delivery catheter guide boss retainer 592*a* performs the same functions as the delivery catheter guide boss retainer 398*a*, as described herein.

For Step 2, the connector arm retainer 592*b* is the second color, yellow. The flat panel 594*b* of the connector arm retainer 592*b* extends proximally and distally from the pull tab 400 such that it is stacked directly underneath the delivery catheter guide boss retainer 592*a*, and directly on top of the stop retainer 592*c*. The connector arm retainer 592*b* performs the same functions as the connector arm retainer 398*c*, as described herein.

For Step 3, the stop retainer 592*c* is the third color, green. The flat panel 594*c* of the stop retainer 592*c* extends distally from the pull tab 400 such that it is stacked directly underneath the connector arm retainer 592*b*, and directly on top of the malecot holding tube guide boss retainer 592*d*. The stop retainer 592*c* performs the same functions as the stop retainer 398*b*, as described herein.

For Step 4, the malecot holding tube guide boss retainer 592*d* is the fourth color, blue. The flat panel 594*d* of the stop retainer 592*d* extends distally from the pull tab 400 such that it is stacked directly underneath the stop retainer 592*c*, and directly on top of the claw guide boss retainer 592*e*. The malecot holding tube guide boss retainer 592*d* performs the same functions as the malecot holding tube guide boss retainer 398*d*, as described herein.

For Step 5, the claw guide boss retainer 592*e* is the fifth color, purple. The flat panel 594*e* of the claw guide boss retainer 592*e* extends distally from the pull tab 400 such that it is stacked directly underneath the malecot holding tube guide boss retainer 592*d*. The claw guide boss retainer 592*e* performs the same functions as the claw guide boss retainer 398*e*, as described herein.

FIGS. 60A and 60B illustrate another embodiment of a shunt loader 600 which is substantially the same as the shunt loader 590, except that it has another alternative design for the retainers 602 which incorporates instructional graphics/colors. The retainers 602 are similar to the retainers 592, except that the retainers 602 have centrally stacked pull tabs 400. As shown in FIG. 60, the pull tabs 400 for the retainers 602 stack onto each other. Each of the retainers 602 includes a pin 402 connected to a pull tab 400 via an extension arm 604. The retainers 602 are thin panels so that they stack in a relatively thin stack.

Accordingly, for Step 1, the delivery catheter guide boss retainer 602*a* is the first color, orange. The extension arm 604*a* of the delivery catheter guide boss retainer 602*a* extends proximally from the pull tab 400 to the pin 402. The delivery catheter guide boss retainer 602*a* is on top of the stack of retainers 592, directly on top of the connector arm retainer 602*b*. The delivery catheter guide boss retainer 602*a* performs the same functions as the delivery catheter guide boss retainer 398*a*, as described herein.

For Step 2, the connector arm retainer 602*b* is the second color, yellow. The connector arm retainer 602*b* does not require an extension arm because its pin is centrally located. The connector arm retainer 592*b* is stacked directly underneath the delivery catheter guide boss retainer 602*a*, and directly on top of the stop retainer 602*c*. The connector arm retainer 602*b* performs the same functions as the connector arm retainer 398*c*, as described herein.

For Step 3, the stop retainer 602*c* is the third color, green. The connector arm retainer 602*c* also does not require an extension arm because its pin is located within the length of the pull tab 400. The stop retainer 602*c* is stacked directly underneath the connector arm retainer 602*b*, and directly on top of the malecot holding tube guide boss retainer 592*d*.

The stop retainer 602c performs the same functions as the stop retainer 398b, as described herein.

For Step 4, the malecot holding tube guide boss retainer 602d is the fourth color, blue. The extension arm 604d of the malecot holding tube guide boss retainer 602d extends distally from the pull tab 400 to the pin 402. The malecot holding tube guide boss retainer 602d is stacked directly underneath the stop retainer 602c, and directly on top of the claw guide boss retainer 602e. The malecot holding tube guide boss retainer 602d performs the same functions as the malecot holding tube guide boss retainer 398d, as described herein.

For Step 5, the claw guide boss retainer 592e is the fifth color, purple. The extension arm 604e of the claw guide boss retainer 592e extends distally from the pull tab 400 to the pin 402. The claw guide boss retainer 592e is stacked directly underneath the malecot holding tube guide boss retainer 602d. The claw guide boss retainer 602e performs the same functions as the claw guide boss retainer 398e, as described herein.

FIG. 61 illustrates another embodiment of the connector arm retainer 398c for the shunt loader 300 of FIGS. 28-49 and as described herein. The connector arm retainer 398c as shown in FIG. 61 has an alternative design for the pull tab 400 which includes a stop retainer cover 600 connected to the pull tab 400 of the connector arm retainer 398c. The stop retainer cover 610 includes a connecting arm 612 connected to the connector arm retainer 398c, a backstop 614 connected to the connecting arm 612, and a cover 616 connected to the top of the backstop 614. The backstop 614 is positioned at the back of the stop retainer 398b such that it blocks the stop retainer 398b from being removed until after the connector arm retainer 398c is removed during Step 2, thereby moving the stop retainer cover 600 from blocking the stop retainer 398b. This prevents a user from incorrectly removing the stop retainer 398b before performing the third and fourth steps (i.e., removing the connector arm retainer 398c and moving the connecting arm 396, malecot holding tube guide boss 350b, claw guide boss 350c and chase pin guide boss 350d during Step 2). This is a potential problem because the stop retainer 398b is the retainer 398 directly to the right of the delivery catheter guide boss retainer 398a, and user may assume that the next step is to remove the stop retainer 398b. The stop retainer cover 536 prevents this error.

Figure 62:
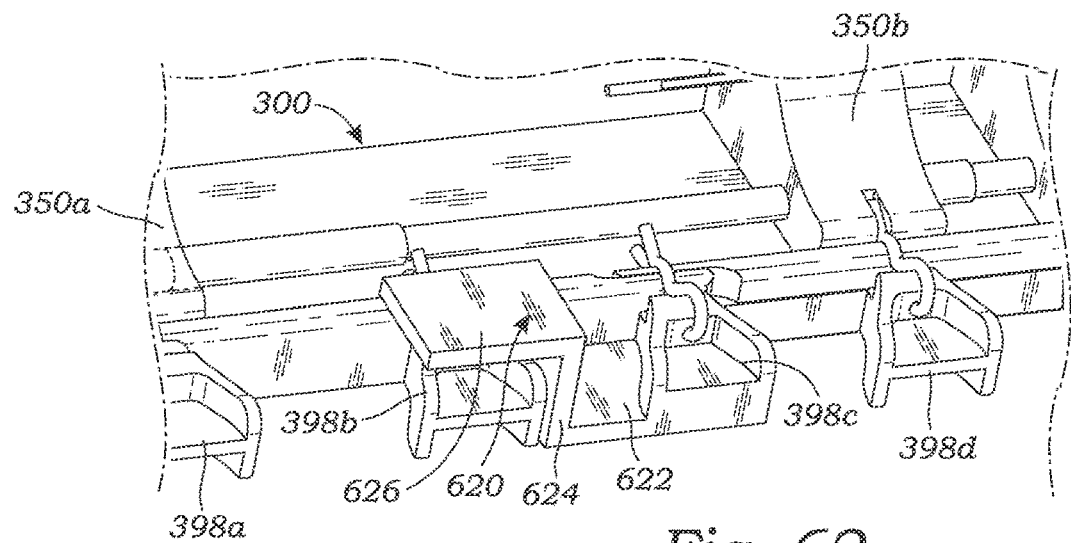
FIG. 62 is a partial perspective view of the shunt loading system of FIG. 28 having an alternative design for a retainer blocking device for preventing incorrect removal of a retainer, according to one embodiment of the disclosed inventions.

FIG. 62 illustrates another embodiment of a stop retainer cover 620 for the shunt loader 300 of FIGS. 28-49 and as described herein. The stop retainer cover 620 is connected to the pull tab 400 of the connector arm retainer 398c. The stop retainer cover 620 comprises a flat connecting arm 622 connected to the bottom of the pull tab 400 of connector arm retainer 398c, a wall 624 extending upward from the connecting arm 622 and a cover 624 connected to the wall 624 which extends over the top of the stop retainer 398b. The stop retainer cover 620 operates in the same manner, and performs the same function as the stop retainer cover 610.

Figure 63:
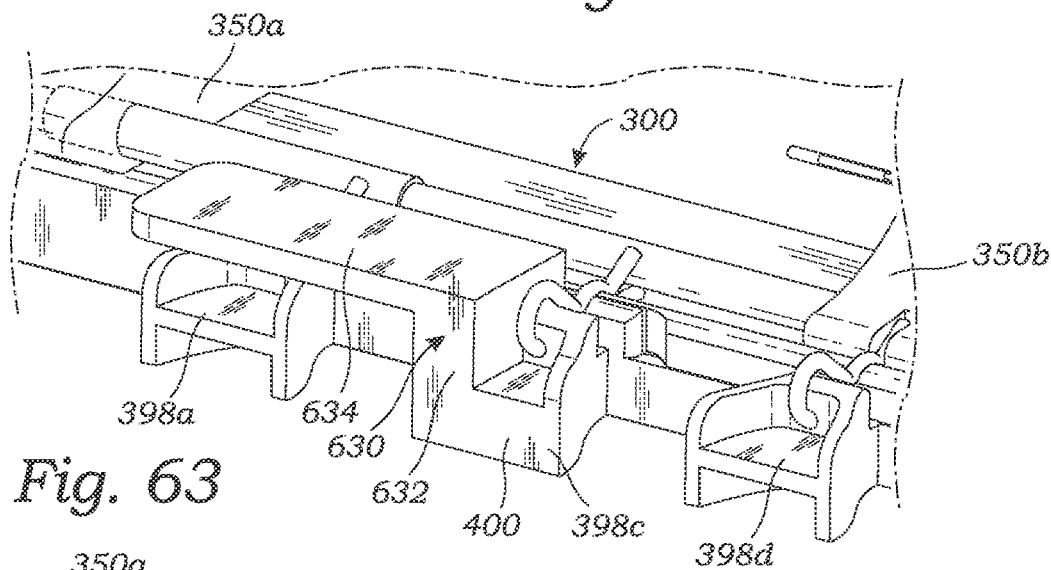
FIG. 63 is a partial perspective view of the shunt loading system of FIG. 28 having an alternative design for a retainer blocking device for preventing incorrect removal of a retainer, according to one embodiment of the disclosed inventions.

FIG. 63 illustrates still another embodiment of a stop retainer cover 630 for the shunt loader 300 of FIGS. 28-49 and as described herein. The stop retainer cover 630 is connected to the pull tab 400 of the connector arm retainer 398c. The stop retainer cover 630 comprises a wall 632 connected to (e.g., integrally formed with) the pull tab 400 and extending upward from the connector arm retainer 398c and a cover 634 connected to the wall 632 which extends over the top of the stop retainer 398b. The stop retainer cover 630 operates in the same manner, and performs the same function as the stop retainer cover 610.

Figure 64:
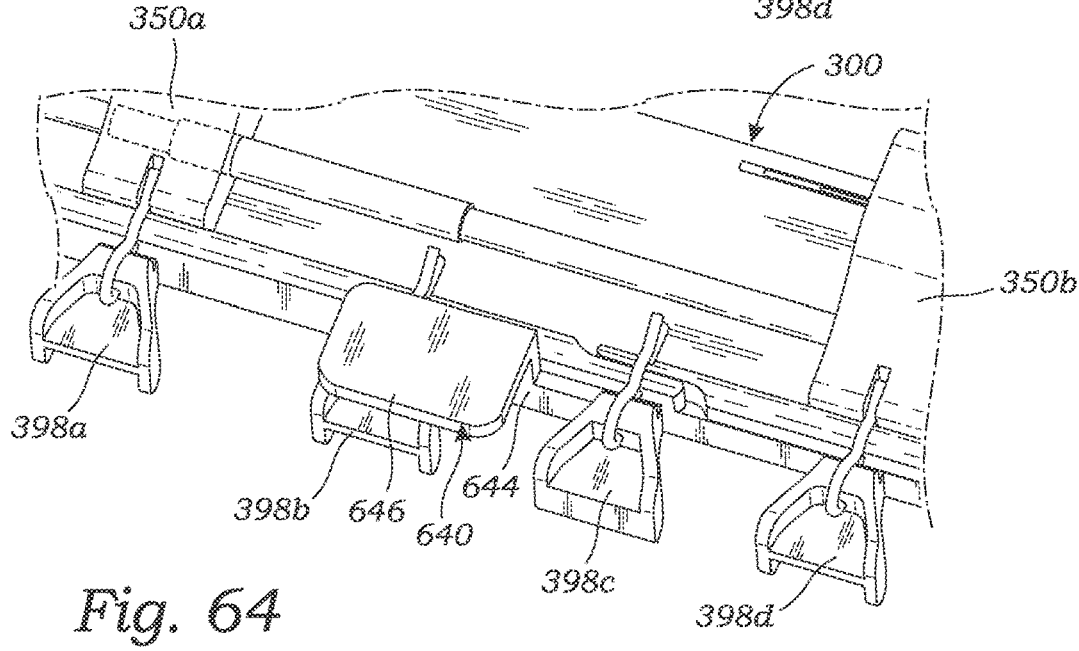
FIG. 64 is a partial perspective view of the shunt loading system of FIG. 28 having an alternative design for a retainer blocking device for preventing incorrect removal of a retainer, according to one embodiment of the disclosed inventions.

FIG. 64 illustrates still another embodiment of a stop retainer cover 640 for the shunt loader 300 of FIGS. 28-49 and as described herein. The stop retainer cover 640 comprises a connector arm 642 connected to the pull tab 400 of the connector arm retainer, a wall 644 extending upward from the connector arm 642, and a cover 646 connected to the wall 644 which extends over the top of the stop retainer 398b. The stop retainer cover 640 operates in the same manner, and performs the same function as the stop retainer cover 610.

Figure 65:
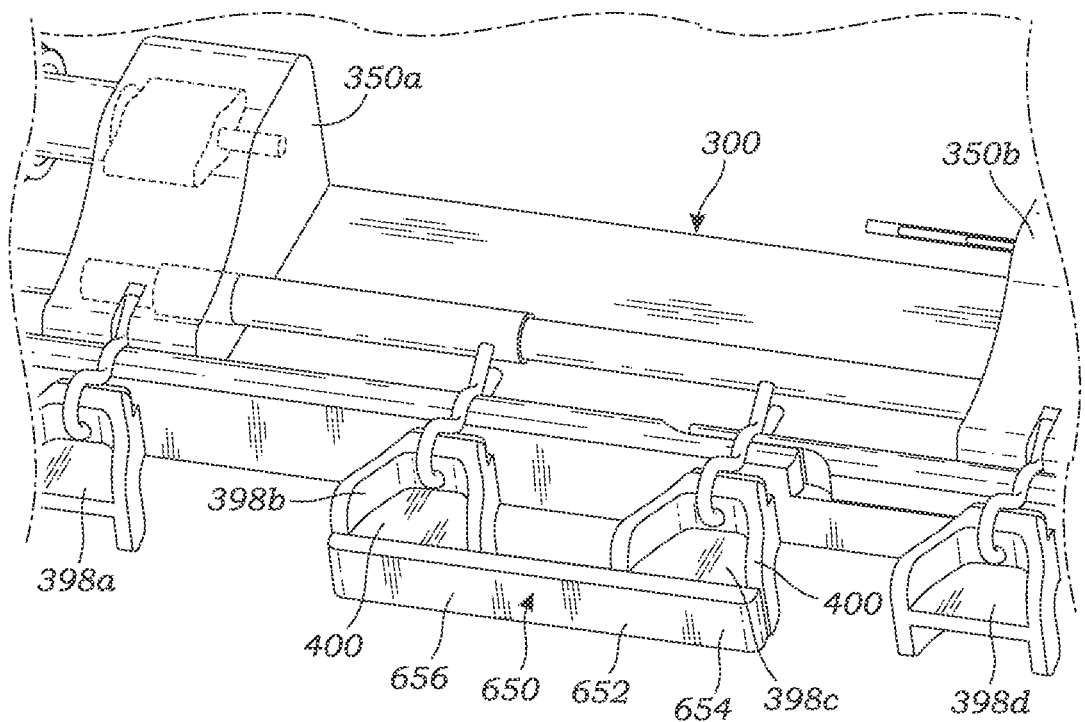
FIG. 65 is a partial perspective view of the shunt loading system of FIG. 28 having an alternative design for a retainer blocking device for preventing incorrect removal of a retainer, according to one embodiment of the disclosed inventions.

FIG. 65 illustrates yet another embodiment of a device for preventing the incorrect removal of the stop retainer for the shunt loader 300 of FIGS. 28-49 and as described herein. The device of FIG. 65 is a stop retainer backstop 650. The stop retainer backstop 650 comprises a flat bar 652 having a first end 654 connected to the back of the pull tab 400 of the connector arm retainer 398c. The flat bar 652 extends proximally to a second end 656 adjacent to the back of the pull tab 400 of the stop retainer 398b such that it blocks the stop retainer 398b from being removed while the connector arm retainer 398c is inserted. The stop retainer backstop 650 operates in the same manner, and performs the same function as the stop retainer cover 610.

Figure 66:
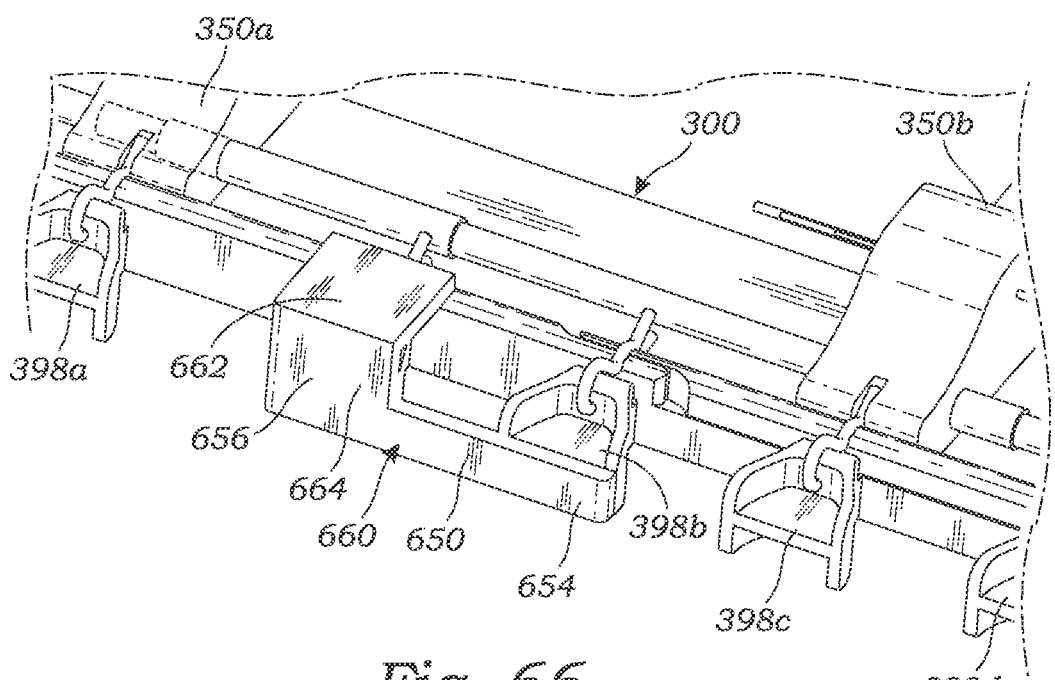
FIG. 66 is a partial perspective view of the shunt loading system of FIG. 28 having an alternative design for a retainer blocking device for preventing incorrect removal of a retainer, according to one embodiment of the disclosed inventions.

FIG. 66 illustrates another embodiment of a device for preventing the incorrect removal of the stop retainer for the shunt loader 300 of FIGS. 28-49 and as described herein. The device of FIG. 66 is a stop retainer backstop 660 similar to the stop retainer backstop 660, except that the stop retainer backstop 660 also has a cover 662. The stop retainer backstop 660 comprises a flat bar 656 having a first end 654 connected to the back of the pull tab 400 of the connector arm retainer 398c. The flat bar 652 extends proximally to a wall 664 extending upward to the cover 662 which extends over the top of the stop retainer 398b. The stop retainer backstop 660 operates in the same manner, and performs the same function as the stop retainer cover 610.

FIG. 67 illustrates yet another embodiment of a device for use with the shunt loader 300 of FIGS. 28-49, to prevent the incorrect removal of the stop retainer 398b. The connector arm retainer 398c in FIG. 66 includes a pull prevention flap 670 connected to the stop retainer 398b. The pull prevention flap 670 extends distally to behind the connector arm retainer 398c such that the connector arm retainer 398c blocks the pull prevention flap 670 from moving laterally away from the shunt loader 300. Since the pull prevention flap 670 is connected to the stop retainer 398b, the pull prevention flap 670 prevents the stop retainer 398b from being removed while the connector arm retainer 398c is installed. After the connector arm retainer 398c has been removed during Step 2, the stop retainer 398c, pull prevention flap 670 is not blocked by the connector arm retainer 398c, and the stop retainer 398c can be removed. Accordingly, the pull prevention flap 670 performs the same function as the stop retainer cover 610.

What is claimed is:

1. An apparatus for loading an endovascular shunt into a delivery catheter, the apparatus comprising:
   a base;
   a boss rod extending longitudinally across the base, the boss rod having a first end fixed to a first side portion of the base, and a second end fixed to a second side portion of the base opposite the first side portion;
   a plurality of guide bosses slidably coupled to the boss rod;

a compression fitting connected to a respective one of the guide bosses and configured for securing the delivery catheter while the shunt is loaded into the delivery catheter.

2. The apparatus of claim 1, wherein the boss rod extends through a respective aperture in each of the guide bosses, such that the guide bosses are translatable along the boss rod.

3. The apparatus of claim 1, further comprising a plurality of guide boss retainers, each guide boss retainer associated with a corresponding one of the guide bosses, wherein the guide boss retainers are configured to selectively secure the corresponding guide boss to prevent the respective guide boss from translating along the boss rod.

4. The apparatus of claim 1, the plurality of guide bosses including a delivery catheter guide boss, wherein the compression fitting is connected to a first lateral side of the delivery catheter guide boss.

5. The apparatus of claim 4, further comprising a first bump tube slideably received on the boss rod and connected to a second lateral side of the delivery catheter guide boss opposite of the first lateral side.

6. The apparatus of claim 5, the plurality of guide bosses further including a malecot holding tube guide boss, wherein a malecot holding tube is connected to a first lateral side of the malecot guide boss extending towards the second lateral side of the delivery catheter guide boss.

7. The apparatus of claim 6, wherein the malecot holding tube is in fluid communication with a flush lumen extending within the malecot holding tube guide boss.

8. The apparatus of claim 6, further comprising a second bump tube slideably received on the boss rod and connected to a second lateral side of the malecot holding tube guide boss opposite of the first lateral side.

9. The apparatus of claim 8, the plurality of guide bosses further including a claw assembly guide boss, where a claw assembly is attached to a first lateral side of the claw guide boss.

10. The apparatus of claim 9, wherein the claw assembly comprises a shaft inserted into a hole in the claw guide boss, the shaft having a lumen for receiving a chase pin there through, wherein an end of the shaft extends toward the second lateral side of the malecot holding tube guide boss and is formed into a plurality of gripping prongs.

11. The apparatus of claim 10, wherein the plurality of guide bosses further includes a chase pin guide boss, and wherein the chase pin is connected to a first lateral side of the chase pin guide boss extending towards the second lateral side of the claw assembly guide boss.

12. The apparatus of claim 11, wherein the respective chase pin guide boss, claw assembly guide boss, and malecot holding tube guide boss are attached to a sled, the sled being translatable relative to the boss rod, such that translation of the sled relative to the boss rod simultaneously translates each of the chase pin guide boss, claw assembly guide boss, and malecot holding tube guide boss a same distance along the guide rod.

13. The apparatus of claim 11, further comprising a spring-loaded locking pin extending towards the base from a bottom of the chase pin guide boss, the base including a locking pin slot configured to receive the locking pin when the chase pin guide boss is translated laterally along the boss rod over the locking pin slot to thereby prevent further translation of the chase pin guide boss.

14. The apparatus of claim 13, the base comprising a groove through which the locking pin translates as the chase pin guide boss translates along the boss rod, the groove having a bottom surface comprising a ramp that moves the locking pin vertically relative to the base as the locking pin translates along the groove, wherein the locking pin slot is located proximate to an end of the ramp.

* * * * *